US010487308B2

(12) United States Patent
Hayashi et al.

(10) Patent No.: US 10,487,308 B2
(45) Date of Patent: Nov. 26, 2019

(54) CULTURE MEDIUM COMPOSITION

(71) Applicant: NISSAN CHEMICAL CORPORATION, Tokyo (JP)

(72) Inventors: Hisato Hayashi, Funabashi (JP); Misayo Otani, Funabashi (JP); Koichiro Saruhashi, Funabashi (JP); Taito Nishino, Shiraoka (JP); Takehisa Iwama, Funabashi (JP); Tatsuro Kanaki, Shiraoka (JP); Ayako Aihara, Shiraoka (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 50 days.

(21) Appl. No.: 15/113,762

(22) PCT Filed: Jan. 23, 2015

(86) PCT No.: PCT/JP2015/051787
§ 371 (c)(1),
(2) Date: Jul. 22, 2016

(87) PCT Pub. No.: WO2015/111686
PCT Pub. Date: Jul. 30, 2015

(65) Prior Publication Data
US 2017/0009201 A1 Jan. 12, 2017

(30) Foreign Application Priority Data

Jan. 23, 2014 (JP) ................................ 2014-010842
Jun. 16, 2014 (JP) ................................ 2014-123772
Aug. 28, 2014 (JP) ................................ 2014-174574
Oct. 24, 2014 (JP) ................................ 2014-217761

(51) Int. Cl.
*C12N 5/00* (2006.01)

(52) U.S. Cl.
CPC ........ *C12N 5/0068* (2013.01); *C12N 2533/70* (2013.01); *C12N 2533/72* (2013.01); *C12N 2533/78* (2013.01); *C12N 2535/00* (2013.01)

(58) Field of Classification Search
CPC .... A61K 2300/00; A61K 35/30; A61K 35/12; A61K 35/51; A61K 35/28; A61K 35/48; A61K 38/13; A61K 38/18; A61K 38/19; A61K 38/363; A61K 38/47; A61K 38/4833; A61K 47/42; A61K 35/44; A61K 35/50; A61K 47/36; A61K 35/15; A61K 38/1825; A61K 38/1841; A61K 45/06; A61K 31/195; A61K 35/00; A61K 35/34; A61K 35/545; A61K 38/193; A61K 45/00; A61K 9/0063; A61K 9/06; C08F 2220/325; C08F 212/08; C08F 8/06; C08F 220/58; C08F 8/34; C08F 220/32; C08F 2800/10; A61L 27/18; A61L 27/56; A61L 27/3604; A61L 27/48; A61L 27/227; A61L 27/52; A61L 2430/02; A61L 27/38; A61L 27/44; A61L 27/3852; A61L 27/3895; A61L 27/54; A61L 27/26; A61L 27/58; A61L 27/3834; A61L 27/50; A61L 2400/12; A61L 27/34; A61L 2300/414; A61L 2300/606; A61L 2400/18; A61L 2430/06; A61L 27/16; A61L 27/22; A61L 27/3817; A61L 29/085; A61L 29/14; A61L 31/10; A61L 31/14; A61L 2300/252; A61L 2300/30; A61L 2430/38; A61L 27/3654; A61L 27/3839; A61L 27/3847; A61L 27/3856; A61L 27/3886; A61L 15/40; A61L 2300/64; A61L 2420/02; A61L 2430/34; A61L 2430/40; A61L 26/0057; A61L 26/0076; A61L 27/12; A61L 27/3608; A61L 27/3683; A61L 27/3821; A61L 15/28; A61L 27/20; A61L 15/425; A61L 15/64; A61L 27/60; C08L 71/02; C08L 89/00; C08L 67/04; C08L 5/08; C12N 5/0605; C12N 2509/00; C12N 2533/50; C12N 5/0068; C12N 2500/32; C12N 2500/34; C12N 2500/44; C12N 2500/95; C12N 2501/12; C12N 2501/21; C12N 2501/23; C12N 2506/02; C12N 2506/03; C12N 2502/02; C12N 2510/00;

(Continued)

(56) References Cited

U.S. PATENT DOCUMENTS 6,872,311 B2 * 3/2005 Koslow ................. A61L 2/0017
  210/500.1
2007/0207540 A1    9/2007  Akashi et al.
2013/0344036 A1   12/2013  Yliperttula et al.

FOREIGN PATENT DOCUMENTS

JP      2007-319074 A    12/2007
JP      2012-231743 A    11/2012
WO   WO 2006/109367 A1   10/2006

OTHER PUBLICATIONS

Chen et al., *Journal of Membrane Science*, 450: 224-234 (2014).

(Continued)

*Primary Examiner* — Deborah K Ware
(74) *Attorney, Agent, or Firm* — Leydig, Voit & Mayer, Ltd.

(57) ABSTRACT

The present invention provides a culture method of cells and/or tissues including culturing cells and/or tissues in a suspended state by using a medium composition having an effect of preventing sedimentation of cells and/or tissues, which is afforded by substantially retaining the cells and/or tissues without substantially increasing the viscosity of the solution by nanofibers which have been added to the solution and uniformly dispersed in the liquid medium, and the like.

1 Claim, 22 Drawing Sheets

(58) Field of Classification Search
CPC .............. C12N 5/0607; C12N 2501/11; C12N 2501/115; C12N 2501/119; C12N 2533/90; C12N 15/63; C12N 2506/45; C12N 2533/30; C12N 2533/54; C12N 5/0619; C12N 5/0655; C12N 5/0662; C12N 5/0668; C12N 5/10; C12N 2501/113; C12N 2501/305; C12N 2501/31; C12N 2533/52; C12N 2533/70; C12N 2533/72; C12N 2533/74; C12N 2533/78; C12N 2533/92; C12N 2535/00; C12N 5/0656; D01F 4/02; D01F 1/02; D01F 6/94; D01D 5/0007; D01D 5/0038; D01D 5/00; D01D 5/003; D01D 5/0092; B29C 39/003; B29C 39/203; B29C 55/005; B29D 7/01; B29K 2089/00; B29L 2007/00; B29L 2009/00; C07K 14/43536; C07K 14/43586; C08J 2201/0444; C08J 2201/0504; C08J 2205/022; C08J 2389/00; C08J 3/07; C08J 3/075; C08J 5/18; C08J 9/0061; C08J 9/26; C08J 9/28; D06M 13/17; D06M 15/03; D06M 15/11; Y10T 428/249921; Y10T 442/10; Y10T 442/60; Y10T 428/29; A61F 2210/0004; A61F 2002/30062; A61F 2002/444; A61F 2002/4445; A61F 2002/445; A61F 2002/4495; A61F 2/30756; A61F 2/441; A61F 2/442; A61F 2002/0086; A61F 2240/001; A61F 2/0063; A61F 2/0077; A61F 2/02; A61F 90/00; A61F 13/00008; A61F 13/00012; A61F 13/00063; B01L 2300/161; B01L 3/502707; B01L 3/56; C12M 23/20; C12M 39/00; C12M 25/14; C12M 35/04; G01N 33/4833; G01N 33/15; G01N 33/5044; C08B 37/0072; D04H 1/4242; D04H 1/728; D10B 2509/00; C12P 21/00; C12P 21/02
See application file for complete search history.

(56) References Cited

OTHER PUBLICATIONS

De Silva et al., *Journal of Applied Polymer Science*, 130: 3374-3383 (2013).
Hassanzadeh et al., *Journal of Materials Chemistry B*, 1: 4217-4224 (2013).
Hussain et al., *Biotechnology and Bioengineering*, 110(2): 637-647 (2013).
Liu et al., *Biomaterials*, 34(18): 4404-4417 (2013).
Muller et al., *Journal of Biomaterials Science, Polymer Edition*, 24(11): 1368-1377 (2013).
Japan Patent Office, International Search Report in International Patent Application No. PCT/JP2015/051787 (dated Apr. 21, 2015).
Lee et al., "Control of Osteogenic Differentiation and Mineralization of Human Mesenchymal Stem Cells on Composite Nanofibers Containing Poly[lactic-co-(glycolic acid)] and Hydroxyapatite,"*Macromol. Biosci.*, 10(2): 173-182 (2010).
Shin et al., "Efficient formation of cell spheroids using polymer nanofibers," *Biotechnol. Lett.*, 34(5): 795-803 (2012).
Sims-Mourtada et al., "Enrichment of breast cancer stem-like cells by growth on electrospun polycaprolactone-chitosan nanofiber scaffolds," *Int. J. Nanomedicine.*, 9: 995-1003 (2014).
European Patent Office, Extended European Search Report in European Patent Application No. 15740159.7 (dated Jun. 12, 2017).

* cited by examiner with deacylated gellan gum　　without deacylated gellan gum xanthan gum
(0.15%)

κ-carageenan + locust bean gum
(0.05%)   +    (0.05%)

HepG2 cell sphere laminin-coated GEM alginic acid beads collagen gel capsule suspension culture of
rice-derived callus

DAG

Car dried at room temperature

Car dried at 110°C

Xan

DU

MNC

DAG

Car

Xan

DU

Alg

Fig. 38

| negative control (0 w/v%) | | | | |
|---|---|---|---|---|
| concentration | 0.01 w/v% | 0.03 w/v% | 0.06 w/v% | 0.1 w/v% |
| Example 1' MC | | | | |
| Example 2' PC | | | | |
| Example 3' CT | | | | |
| Example 4' DAG | | | | |
| Example 5' Car | | | | |
| Comparative Example 3' Xan | | | | |
| Comparative Example 4' DU | | | | |
| Comparative Example 5' Alg | | | | |

| | | | | |
|---|---|---|---|---|
| negative control (0 w/v%) |  | | | |
| concentration | 0.01 w/v% | 0.03 w/v% | 0.06 w/v% | 0.1 w/v% |
| Example 1' MC |  |  |  |  |
| Example 2' PC |  |  |  |  |
| Example 3' CT |  |  |  |  |
| Example 4' DAG |  |  |  |  |
| Example 5' Car |  |  |  |  |
| Comparative Example 3' Xan |  |  |  |  |
| Comparative Example 4' DU |  |  |  |  |
| Comparative Example 5' Alg |  |  |  |  |

CULTURE MEDIUM COMPOSITION

CROSS-REFERENCE TO RELATED APPLICATIONS

This patent application is the U.S. national phase of International Patent Application No. PCT/JP2015/051787, filed on Jan. 23, 2015, which claims the benefit of Japanese Patent Application No. 2014-010842, filed Jan. 23, 2014, Japanese Patent Application No. 2014-123772, filed Jun. 16, 2014, Japanese Patent Application No. 2014-174574, filed Aug. 28, 2014, and Japanese Patent Application No. 2014-217761, filed Oct. 24, 2014, the disclosures of which are incorporated herein by reference in their entireties for all purposes.

TECHNICAL FIELD

The present invention relates to a medium composition for culturing animal and plant cells and/or tissues particularly in a three dimensional or suspended state by using a nanofiber such as polysaccharides and the like having enhanced dispersibility in water, and use thereof.

BACKGROUND ART

In recent years, techniques for proliferating or maintaining in vitro various organs, tissues and cells that play distinct roles in the body of animals and plants have been developed. Proliferation or maintenance of the organs and tissues in vitro is called organ culture and tissue culture, respectively, and proliferating, differentiating or maintaining in vitro the cells separated from an organ or tissue is called cell culture. Cell culture is a technique for proliferating, differentiating or maintaining separated cells in vitro in a medium, and is indispensable for detailed analyses of the in vivo function and structure of various organs, tissues and cells. In addition, the cells and/or tissues cultured by the technique are utilized in various fields for efficacy and toxicity evaluation of chemical substances, pharmaceutical products and the like, large-scale production of useful substances such as enzymes, cell growth factors, antibodies and the like, regenerative medicine supplementing organ, tissue and cell that were lost by disease and deficiency, improvement of plant brand, production of genetically modified products, and the like.

Animal-derived cells are broadly divided into non-adherent cells and adherent cells based on the properties thereof. Non-adherent cells are cells that do not require a scaffold for growth and proliferation, and adherent cells are cells that require a scaffold for growth and proliferation. Most of the cells constituting the living body are the latter, adherent cells. As culture methods of adherent cells, single layer culture, dispersion culture, embedded culture, microcarrier culture, sphere culture and the like are known.

Single layer culture is a method of cultivating the object cell as a single layer by using, as a scaffold, a culture container made of glass or a synthetic polymer material that underwent various surface treatments, or supportive cells called feeder cells, and is most generally prevalent. For example, culture methods using culture containers of various shapes or properties such as polystyrene applied with various surface treatments (plasma treatment, corona treatment etc.), coated with cell adhesion factors such as collagen, fibronectin, polylysine and the like, or plated with feeder cells in advance and the like have been developed. However, the single layer culture is problematic in that cells cannot maintain the specific functions they have in vivo for a long term, since the two-dimensional culture environment thereof is completely different from the in vivo environment, the cells cannot reconstruct a tissue similar to that in vivo, it is not suitable for a mass culture of cells since the cell number per a constant area is limited, and the like (patent document 1). In addition, a method of cultivating the object cell on feeder cells sometimes faces a problem in separation of the object cells from the feeder cells (non-patent document 1).

Dispersion culture is a method of cultivating adherent cells in a suspended state, which includes seeding the cells in a medium, and stirring the culture medium in a culture container applied with a surface treatment for inhibiting cell adhesion, to inhibit attachment of the cells to the culture container. However, the adherent cells cultured by the method cannot adhere to a scaffold, and therefore, the method cannot be applied to a cell that essentially requires adhesion to a scaffold for cell proliferation. In addition, being constantly disrupted by a shear force, the cell cannot exhibit its inherent cell function, and therefore, functional cells sometimes cannot be cultivated in a large amount (non-patent document 2).

Embedded culture is a method of cultivating cells by embedding and fixing the cells in a solid or semisolid gel substrate such as agar, methylcellulose, collagen gel, gelatin, fibrin, agarose, alginates and the like. Since the method enables three-dimensional cultivation of the cells in a state closer to in vivo and the gel substrate itself sometimes promotes proliferation and differentiation of the cells, the cells can be cultivated at high density while maintaining the function of the cell, as compared to single layer culture and dispersion culture (patent documents 2, 3). Furthermore, a method of cultivating cells, including forming a microcapsule with a size of 100-300 μm by embedding the cells in the gel substrate, and cultivating the cells in an aqueous solution medium while dispersing the microcapsule has also been developed (non-patent document 3). However, these methods have problems in that successive observation of cultured cells is not possible unless a visible light permeates the gel substrate, recovery of cells from the medium requires a complicated operation that damages the cells such as an enzyme treatment (e.g., collagenase treatment in the case of collagen gel) and the like, since the medium and microcapsule containing a gel substrate have high viscosity, medium exchange necessary for long-term cultivation is difficult and the like. In recent years, techniques enabling cell recovery from a gel substrate by a treatment with heat, shear force and the like have been developed. However, the heat, shear force and the like may exert an adverse effect on the cell function, and the safety of the gel substrate for the living body has not been clarified yet (patent documents 4, 5, non-patent documents 4, 5, 6, 7). In addition, a sol food for preventing precipitation and floating of a particulate food such as fruit, vegetable and the like cut small to keep the food uniformly dispersed and suspended has been developed in the food field. However, the sol food does not consider recovery of the dispersed particulate food, and whether the cells and tissues can be subjected to suspension culture has not been examined (patent document 6). It is known that gellan in an aqueous solution is gelated by the action of a calcium ion and forms a fine structure (non-patent document 8).

Microcarrier culture is a method of cultivating cells in a suspended state by proliferating cells in a single layer on the surface of a fine particle slightly heavier than water (hereinafter to be also referred to as a microcarrier), and stirring the fine particles in a culture container such as a flask and the like. Generally, the microcarrier used for the method is a spherical particle having diameter 100-300 μm, surface area 3000-6000 cm$^2$/g, specific gravity 1.03-1.05, and is composed of a material such as dextran, gelatin, alginic acid, polystyrene and the like. Collagen, gelatin, or a charged group such as dimethylaminoethyl and the like may also be provided to the surface of a microcarrier to facilitate attachment of the cell. This method is applied to a mass culture of a cell since it can markedly increase the culture area (patent documents 7, 8). However, it is difficult to attach the object cell almost uniformly to all microcarriers, and problems occur such as detachment of the cells from the microcarrier due to a shear force during stirring, damage on the cells and the like (non-patent document 9).

Sphere culture is a culture method including forming an aggregate composed of several dozen—several hundred object cells (hereinafter to be also referred to as a sphere), and culturing the aggregates with standing or shaking in a medium. It is known that a sphere has a high cell density, reconstructs cell-cell interactions and cell structure close to those in the in vivo environment, and can be cultured while maintaining the cell function for a longer term as compared to a single layer culture and a dispersion culture method (non-patent documents 10, 11). However, the sphere culture cannot form a large sphere, since supply of nutrition inside the sphere and discharge of wastes are difficult when the size of the sphere is too large. In addition, since the formed sphere needs to be cultivated in a dispersed state on the bottom of a culture container, the number of spheres per a given volume cannot be increased with ease, and it is not suitable for a mass culture. Furthermore, as a method of forming a sphere, hanging drop culture, culture on cell non-adhesive surface, culture inside microwell, rotation culture, culture utilizing cell scaffold, coagulation by centrifugal force, ultrasonication, electric field or magnetic field and the like are known. However, these methods are problematic in that the operation is complicated, recovery of sphere is difficult, size control and large-scale production are difficult, influence on the cell is unknown, special exclusive container and apparatus are necessary and the like (patent document 9).

On the other hand, as for plants, cell, protoplast without a cell wall or organ, tissue, callus of plant such as leaf, stalk, root, growing point, seed, embryo, pollen and the like can also be grown by culture in an aseptic state. Using a culture technique for such plant tissues and cells, brand improvement of plant and production of useful substances have been made possible. As a method for proliferating plant cells and tissues in a large amount in a short time, a method of suspension cultivation of plant cells and tissues in a liquid medium is known (non-patent document 12). To achieve good proliferation thereof, supply of sufficient oxygen, maintenance of a uniform mixing state, prevention of cell damage and the like are important. The oxygen supply to a culture medium and suspending of cells and tissues may be performed by combining aeration and mechanical stirring, or aeration alone. The former may result in defective proliferation due to a damage on the cells and tissues by stirring, and the latter is problematic in that, even though shearing of cells and tissues is less, since a uniform mixing state may be difficult to maintain in high density culture, the cells and tissues form sediment to lower the proliferation efficiency and the like.

Document List

Patent Document patent document 1: JP-A-2001-128660
patent document 2: JP-A-S62-171680
patent document 3: JP-A-S63-209581
patent document 4: JP-A-2009-29967
patent document 5: JP-A-2005-60570
patent document 6: JP-A-8-23893
patent document 7: JP-A-2004-236553
patent document 8: WO 2010/059775
patent document 9: JP-A-2012-65555

Non-Patent Document non-patent document 1:Klimanskaya et al., Lancet 2005, 365:1636-1641
non-patent document 2: King et al., Curr Opin Chem Biol. 2007, 11:394-398
non-patent document 3: Murua et al., J. of Controlled Release 2008, 132:76-83
non-patent document 4: Mendes, Chemical Society Reviews 2008, 37:2512-2529
non-patent document 5: Moon et al., Chemical Society Reviews 2012, 41:4860-4883
non-patent document 6: Pek et al., Nature Nanotechnol. 2008, 3:671-675
non-patent document 7: Liu et al., Soft Matter 2011, 7:5430-5436
non-patent document 8: Perez-Campos et al., Food Hydrocolloids 2012, 28:291-300
non-patent document 9: Leung et al., Tissue Engineering 2011, 17:165-172
non-patent document 10: Stahl et al., Biochem. Biophys. Res. Comm. 2004, 322:684-692
non-patent document 11: Lin et al., Biotechnol J. 2008, 3:1172-1184
non-patent document 12: Weathers et al., Appl Microbiol Biotechnol 2010, 85:1339-1351

SUMMARY OF THE INVENTION

Problems to be Solved by the Invention

An object of the present invention is to solve the above-mentioned problems of the prior art, and provides a medium composition for cultivating cells and/or tissues of an animal or plant particularly in a three-dimensional or suspended state, and a method of culturing cells and/or tissues of an animal or plant by using the medium composition.

Means of Solving the Problems

The present inventors have conducted intensive studies and found that suspension culture of animal and plant cells and/or tissues can be performed while keeping them still by mixing a nanofiber composed of polysaccharides such as cellulose, chitin and the like in a liquid medium, without substantially increasing the viscosity of the liquid medium, and that the proliferation activity of the cell is promoted by culture using this medium composition. In addition, they have found that not only non-water-soluble polysaccharides such as cellulose and the like but also water-soluble polysaccharides such as deacylated gellan gum and the like form a fiber-like structure in a liquid medium that enables suspension culture of animal and plant cells and/or tissues while keeping them still, without substantially increasing the viscosity of the liquid medium. They have further found that cultured cells and/or tissues can be easily recovered from such medium composition. Based on the above findings, they have conducted further studies and completed the present invention.

That is, the present invention is as follows:

[1] A medium composition capable of culturing cells or tissues in a suspended state, which comprises a nanofiber.
[2] The medium composition of [1], permitting an exchange treatment of the medium composition during culture, and recovery of the cells or tissues after completion of the culture.
[3] The medium composition of [1], which allows for recovery of the cells or tissues without any of a temperature change, a chemical treatment, an enzyme treatment and a shear force.
[4] The medium composition of [1], having a viscosity of not more than 8 mPa·s.
[5] The medium composition of [1], wherein the aforementioned nanofiber has an average fiber diameter of 0.001-1.00 μm, and a ratio of an average fiber length (L) to the average fiber diameter (D) (L/D) is 2-500.
[6] The medium composition of [1], wherein the aforementioned nanofiber is constituted of a polymer compound.
[7] The medium composition of [6], wherein the aforementioned polymer compound is a polysaccharide.
[8] The medium composition of [7], wherein the aforementioned polysaccharide comprises
a non-water-soluble polysaccharide selected from the group consisting of cellulose, chitin and chitosan; or
a water-soluble polysaccharide selected from the group consisting of hyaluronic acid, gellan gum, deacylated gellan gum, rhamsan gum, diutan gum, xanthan gum, carageenan, xanthan gum, hexuronic acid, fucoidan, pectin, pectic acid, pectinic acid, heparan sulfate, heparin, heparitin sulfate, keratosulfate, chondroitin sulfate, dermatan sulfate, rhamnan sulfate, alginic acid, and a salt thereof.
[9] The medium composition of [8], wherein the aforementioned polysaccharide comprises cellulose or chitin.
[10] The medium composition of [9], wherein the aforementioned nanofiber is obtained by pulverization.
[11] The medium composition of any of [1] to [10], which is for cell culture.
[12] The medium composition of [11], wherein the aforementioned cell is an adherent cell or a non-adherent cell.
[13] The medium composition of [12], wherein the aforementioned adherent cell is a sphere.
[14] A cell or tissue culture comprising the medium composition of any of [1] to [13] and cells or tissues.
[15] A method of culturing a cell or tissue, comprising cultivating the cell or tissue in the medium composition of any of [1] to [13].
[16] A method of recovering a cell or tissue, comprising separating the cell or tissue from the culture of [14].
[17] The method of [16], wherein the aforementioned separation is performed by centrifugation.
[18] A production method of a sphere, comprising cultivating an adherent cell in the medium composition of any of [1] to [13].
[19] A medium additive for preparing the medium composition of any of [1] to [13], which comprises the nanofiber or a water-soluble polymer compound constituting the nanofiber.
[20] A production method of a medium composition, comprising mixing the medium additive of [19] and a medium.
[21] A production method of the medium composition of any of [1] to [13], comprising mixing the nanofiber or a water-soluble polymer compound constituting the nanofiber and a medium.
[22] A preservation method of a cell or tissue, comprising preserving the cell or tissue in the medium composition of any of [1] to [13].
[23] A transportation method of a cell or tissue, comprising transporting the cell or tissue in the medium composition of any of [1] to [13].
[24] A method of proliferating a cell or tissue, comprising cultivating the cell or tissue in the medium composition of any of [1] to [13].
[25] A method of passage culture of an adherent cell, comprising the following steps:
(1) suspension culturing an adherent cell in the medium composition of any of [1] to [13]; and
(2) (i) adding a fresh medium composition of any of [1] to [13] to a culture containing the adherent cell obtained by the suspension culture of step (1), or (ii) adding a culture containing the adherent cell obtained by the suspension culture of step (1) entirely or partly to a fresh medium composition of any of [1] to [13], without a detaching operation of the cell from a culture container.
[26] A method of proliferating an adherent cell, comprising suspension culturing a adherent cell in a medium composition comprising a chitin nanofiber wherein the adherent cell is attached to the chitin nanofiber.
[27] The method of [26], wherein the medium composition has a chitin nanofiber content of not less than 0.0001% (weight/volume) and not more than 0.1% (weight/volume).

Effect of the Invention

The present invention provides a medium composition containing a nanofiber, particularly a nanofiber composed of a polysaccharide. Using the medium composition, cells and/or tissues can be cultivated in a suspended state without an operation such as shaking, rotation and the like having a risk of causing injury and loss of functions of cells and tissues. Furthermore, using the medium composition, the medium can be exchanged easily during culture, and the cultured cells and/or tissues can also be recovered easily. The present invention applies the culture method to the cells and/or tissues collected from an animal body or a plant body, and can prepare the object cells and/or tissues in a large amount without impairing the functions thereof. The cells and/or tissues obtained by the culture method can be utilized when performing efficacy and toxicity evaluation of chemical substances, pharmaceutical products and the like, large-scale production of useful substances such as enzymes, cell growth factors, antibodies and the like, regenerative medicine for supplementing organ, tissue and cell that were lost by disease and deficiency, and the like.

Since the medium composition of the present invention can maintain cells or tissues in an environment close to the biological environment, it is useful for the preservation and transport of cells and tissues. For example, when adhesion culture of cells is performed on a plate, and the plate is directly transported, the cells may be detached from the plate due to trembling during transport, thus degrading the inherent function of the cells. However, nanofibers form a three dimensional network and support the cells in the medium composition of the present invention, thereby maintaining the cells in a suspended state. Accordingly, damage on the cells resulting from trembling during transport that detaches the cells from the plate and the like can be avoided, and the cells can be preserved and transported while maintaining the inherent functions thereof.

DESCRIPTION OF EMBODIMENTS

Figure 13:
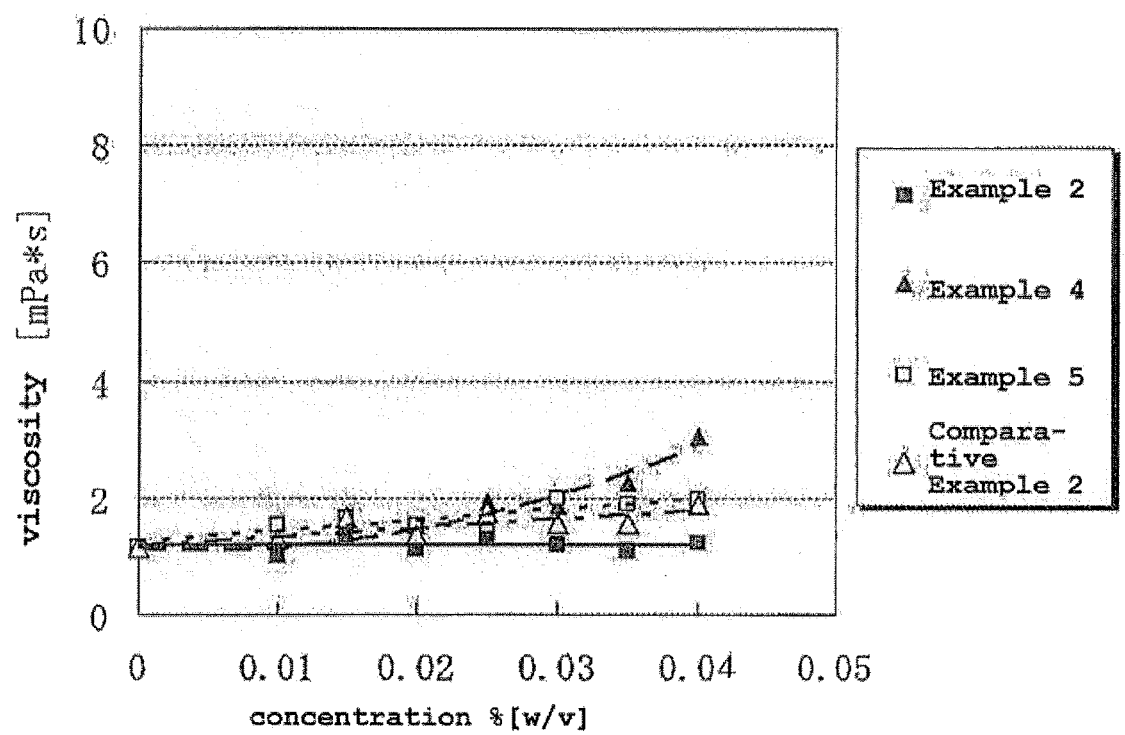

FIG. 13 shows viscosity of each medium composition at 25° C.

Figure 14:
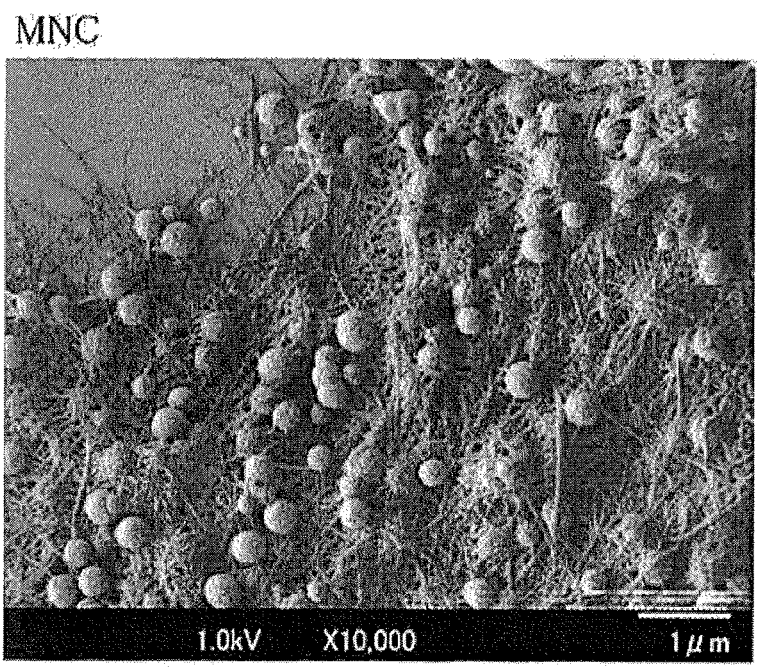

FIG. 14 shows a scanning electron microscope photograph of the MNC-containing medium composition of Example 1.

Figure 15:
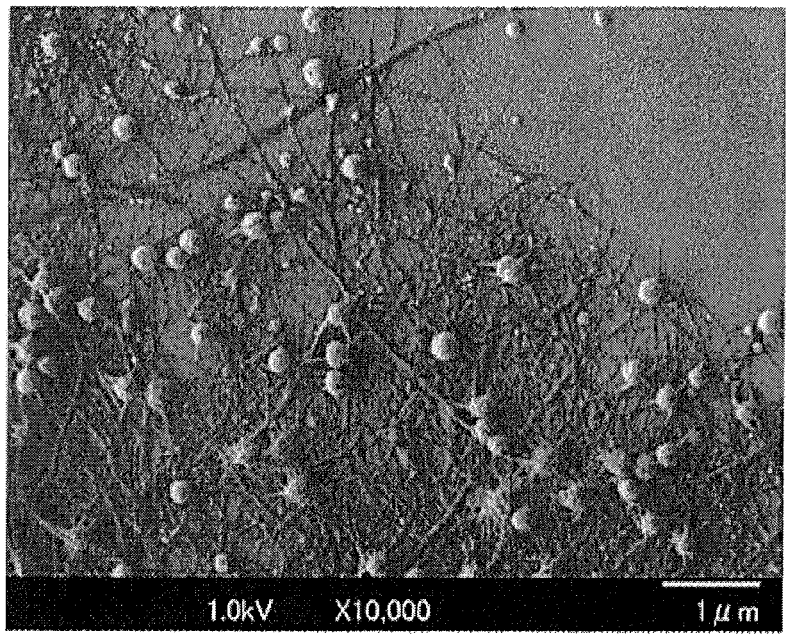

FIG. 15 shows a scanning electron microscope photograph of the PNC-containing medium composition of Example 2.

Figure 16:
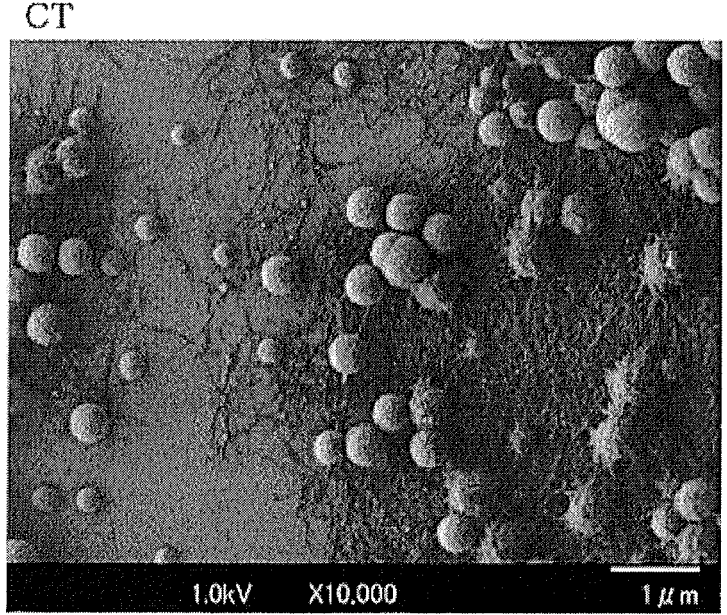

FIG. 16 shows a scanning electron microscope photograph of the CT-containing medium composition of Example 3.

Figure 17:
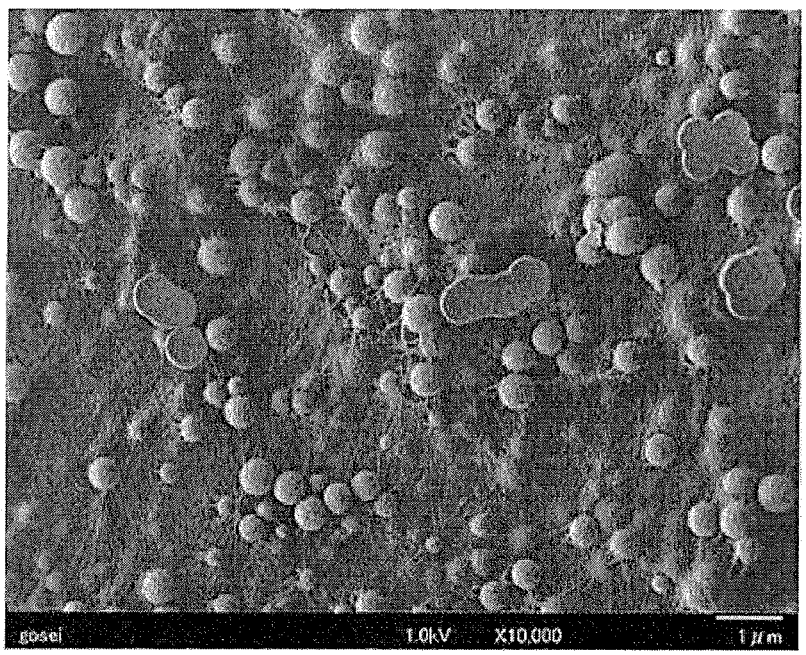

FIG. 17 shows a scanning electron microscope photograph of the DAG-containing medium composition of Example 4.

Figure 18:
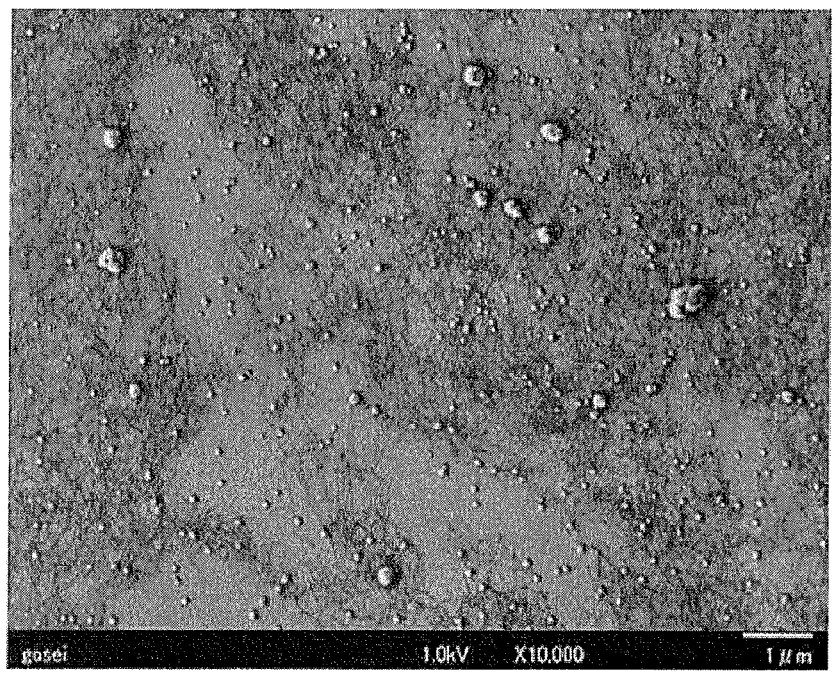

FIG. 18 shows a scanning electron microscope photograph of the Car-containing medium composition of Example 5. Dried at room temperature.

Figure 19:
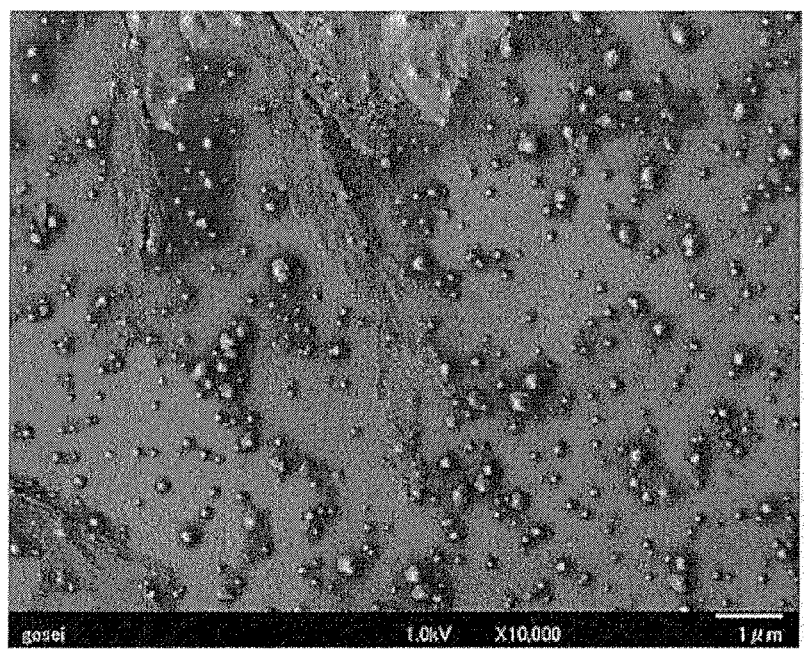

FIG. 19 shows a scanning electron microscope photograph of the Car-containing medium composition of Example 5. Dried at 110° C.

Figure 20:
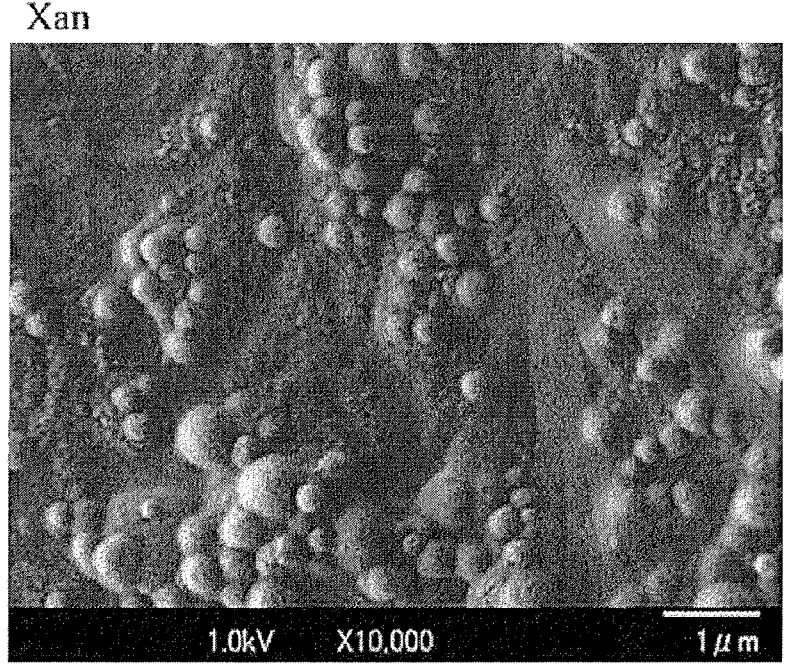

FIG. 20 shows a scanning electron microscope photograph of the Xan-containing medium composition of Comparative Example 3.

Figure 21:
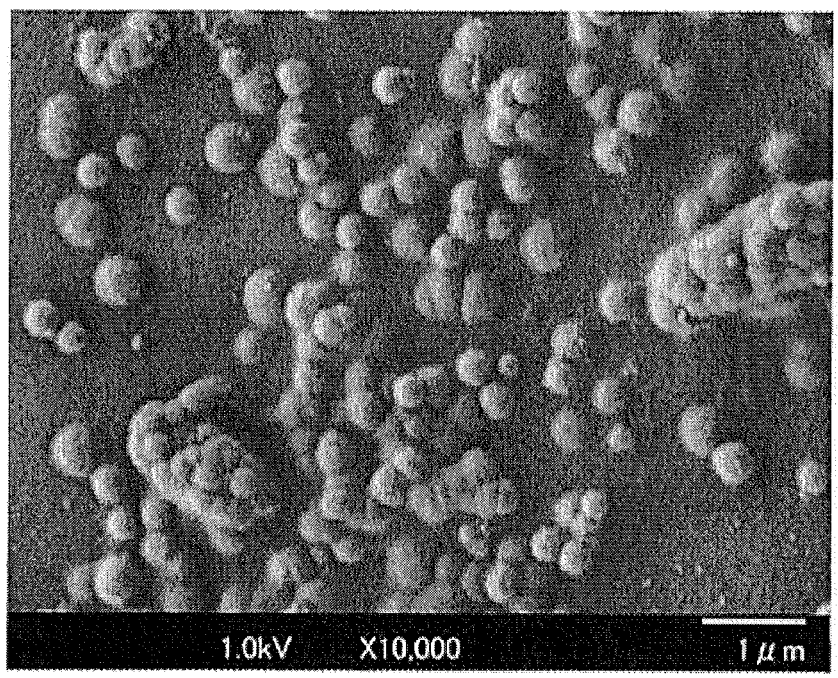

FIG. 21 shows a scanning electron microscope photograph of the DU-containing medium composition of Comparative Example 4.

Figure 22:
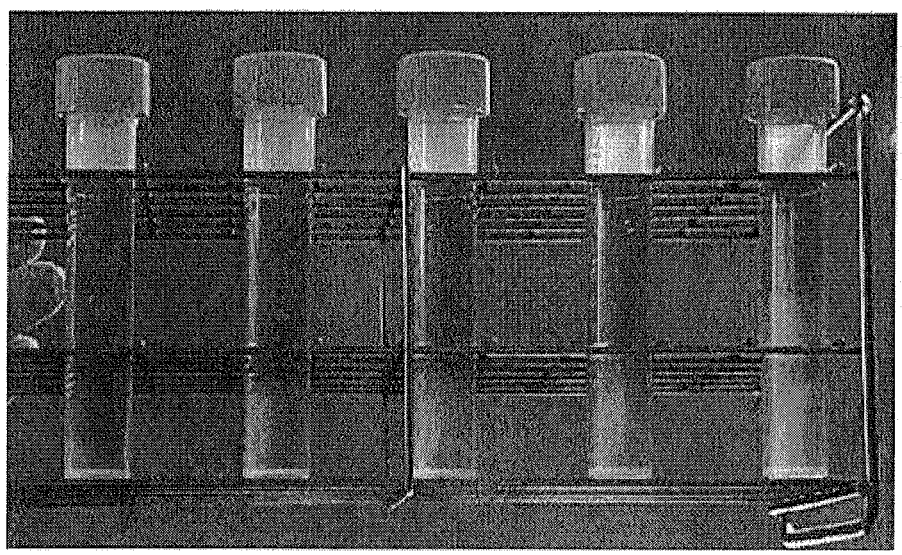

FIG. 22 shows observation results of the dispersion state of HepG2 cell sphere after suspension culture of the cell sphere for 6 days in the MNC-containing medium composition of Example 1. The MNC concentration is 0.01, 0.03, 0.05, 0.07 and 0.1 w/v % from the left.

Figure 23:
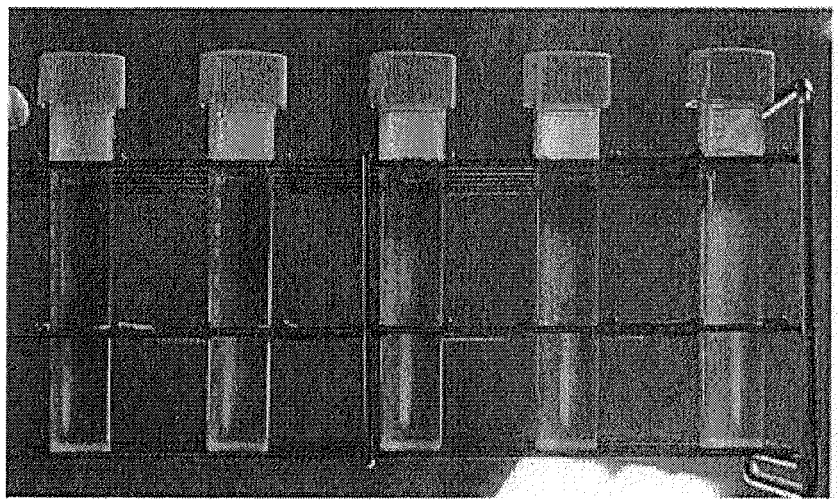

FIG. 23 shows observation results of the dispersion state of HepG2 cell sphere after suspension culture of the cell sphere for 6 days in the PNC-containing medium composition of Example 2. The PNC concentration is 0.01, 0.03, 0.05, 0.07 and 0.1 w/v % from the left.

Figure 24:
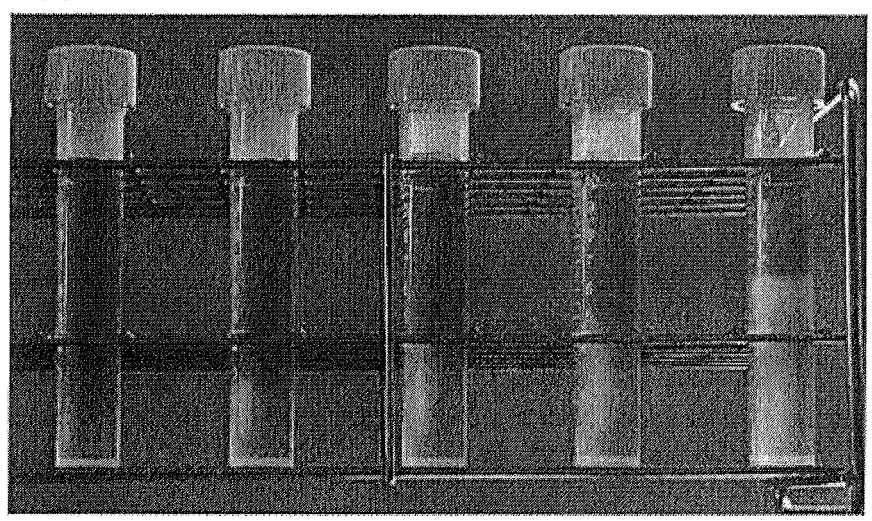

FIG. 24 shows observation results of the dispersion state of HepG2 cell sphere after suspension culture of the cell sphere for 6 days in the CT-containing medium composition of Example 3. The CT concentration is 0.01, 0.03, 0.05, 0.07 and 0.1 w/v % from the left.

Figure 25:
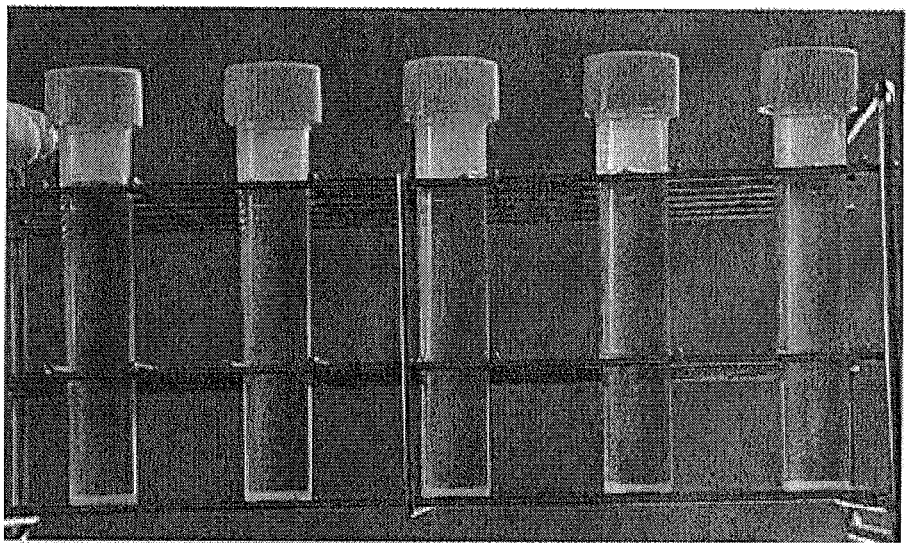

FIG. 25 shows observation results of the dispersion state of HepG2 cell sphere after suspension culture of the cell sphere for 6 days in the DAG-containing medium composition of Example 4. The DAG concentration is 0.01, 0.03, 0.05, 0.07 and 0.1 w/v % from the left.

Figure 26:
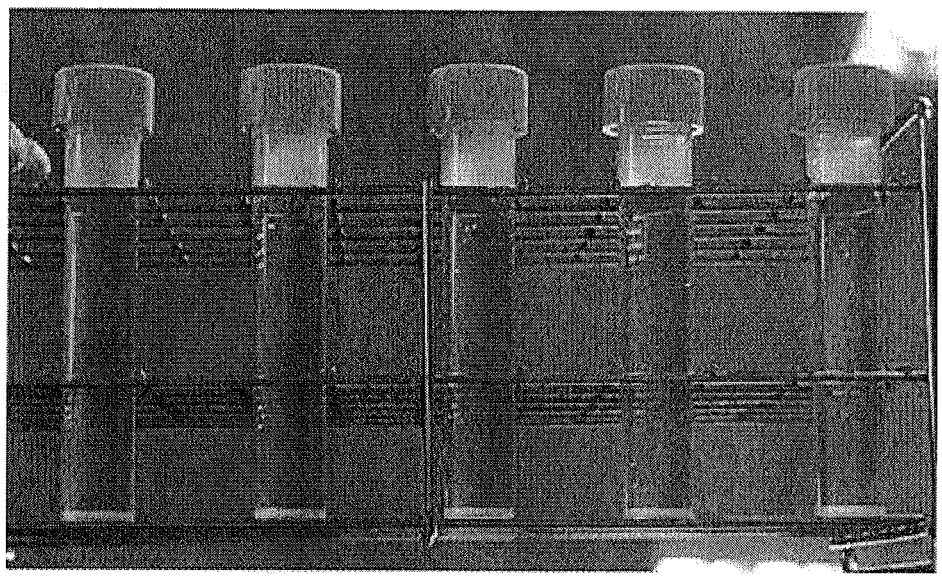

FIG. 26 shows observation results of the dispersion state of HepG2 cell sphere after suspension culture of the cell sphere for 6 days in the Car-containing medium composition of Example 5. The Car concentration is 0.01, 0.03, 0.05, 0.07 and 0.1 w/v % from the left.

Figure 27:
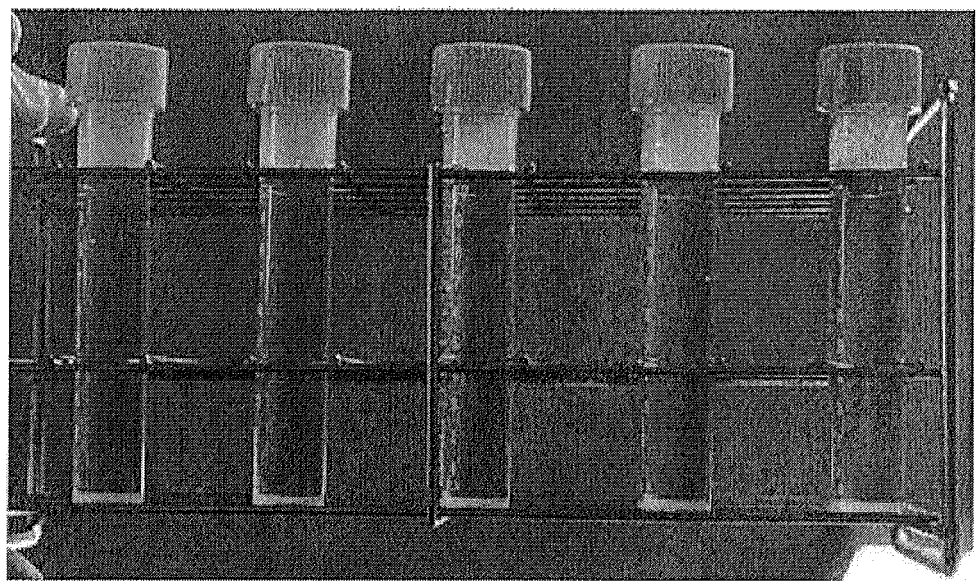

FIG. 27 shows observation results of the dispersion state of HepG2 cell sphere after suspension culture of the cell sphere for 6 days in the Xan-containing medium composition of Example 5. The Xan concentration is 0.01, 0.03, 0.05, 0.07 and 0.1 w/v % from the left.

Figure 28:
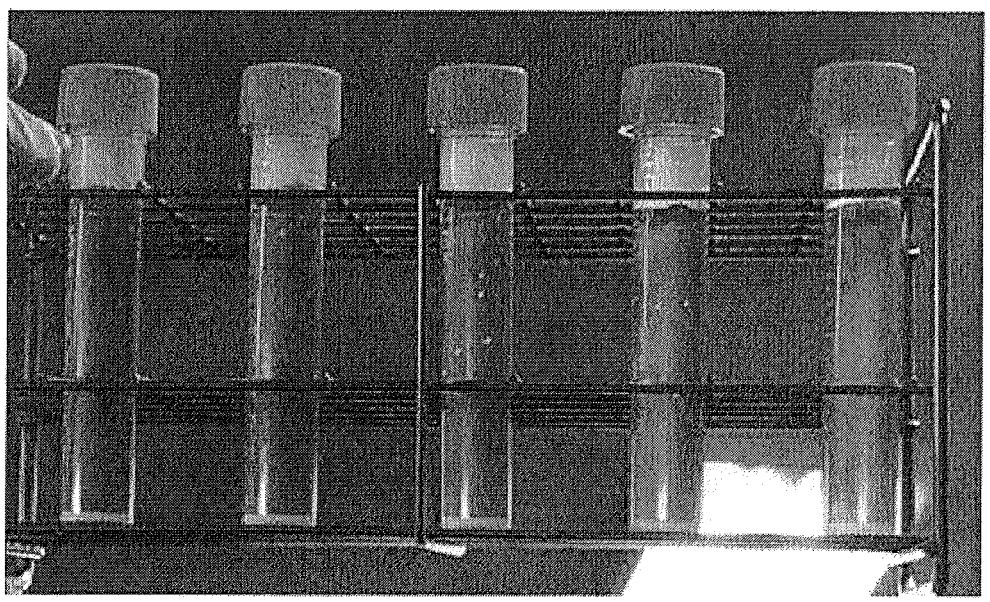

FIG. 28 shows observation results of the dispersion state of HepG2 cell sphere after suspension culture of the cell sphere for 6 days in the DU-containing medium composition of Comparative Example 4. The DU concentration is 0.01, 0.03, 0.05, 0.07 and 0.1 w/v % from the left.

Figure 29:
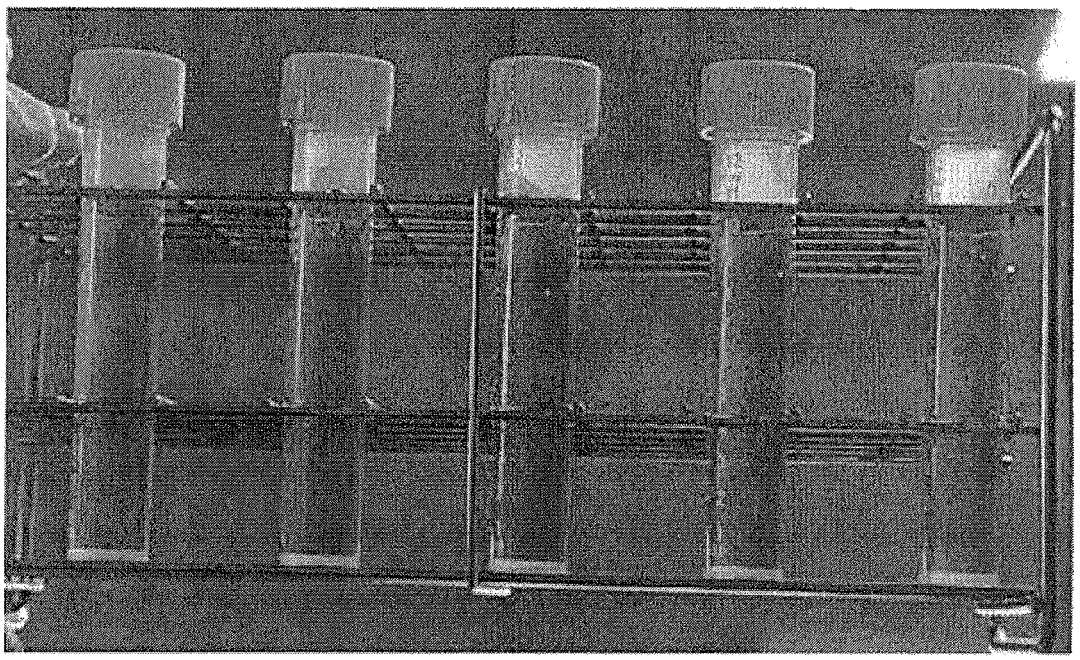

FIG. 29 shows observation results of the dispersion state of HepG2 cell sphere after suspension culture of the cell sphere for 6 days in the Alg-containing medium composition of Comparative Example 5. The Alg concentration is 0.01, 0.03, 0.05, 0.07 and 0.1 w/v % from the left.

Figure 30:
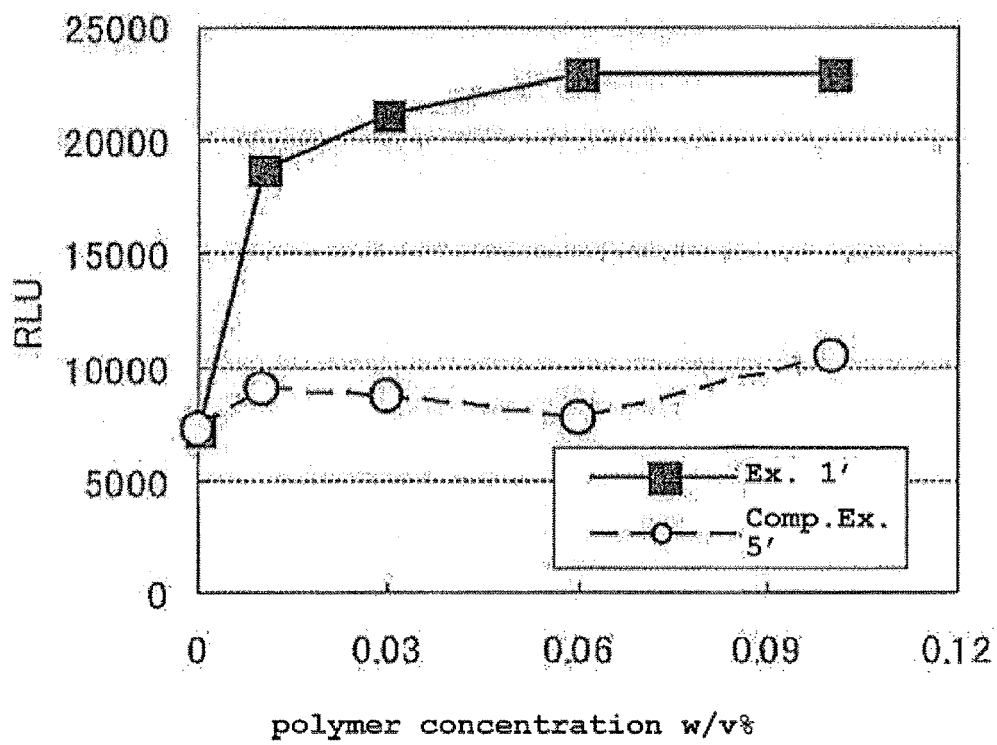

FIG. 30 shows RLU value on day 6 from the start of the suspension culture of MCF7 cells in the medium compositions of Example 1' and Comparative Example 5'.

Figure 31:
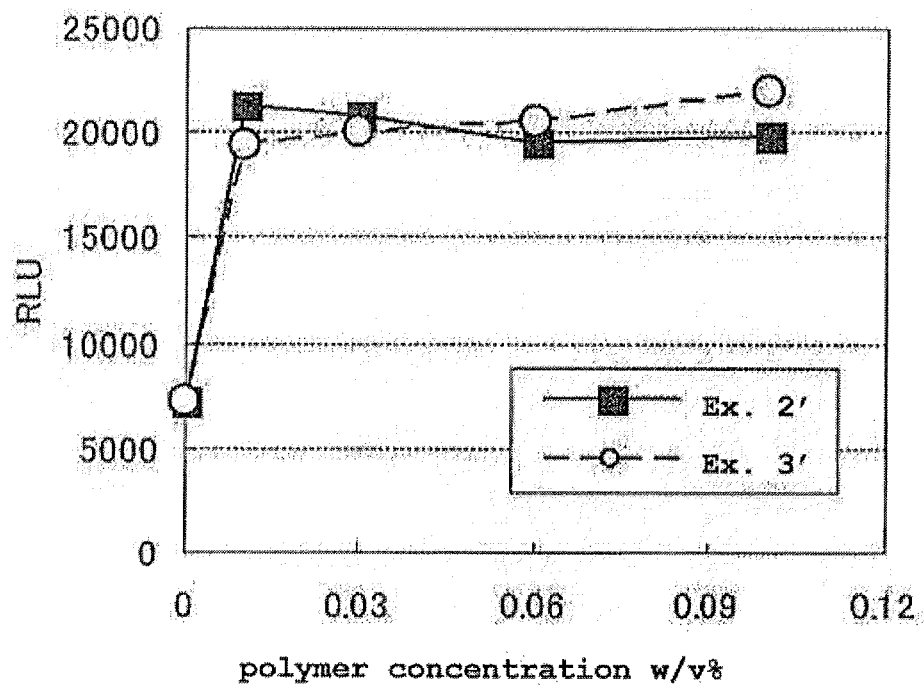

FIG. 31 shows RLU value on day 6 from the start of the suspension culture of MCF7 cells in the medium compositions of Examples 2' and 3'.

Figure 32:
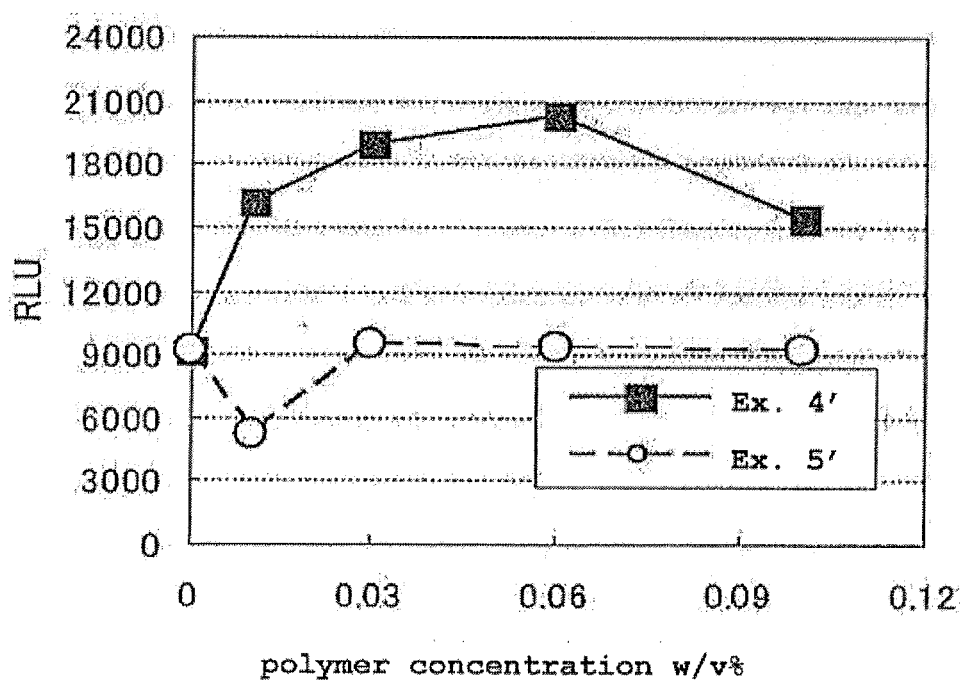

FIG. 32 shows RLU value on day 6 from the start of the suspension culture of MCF7 cells in the medium compositions of Examples 4' and 5'.

Figure 33:
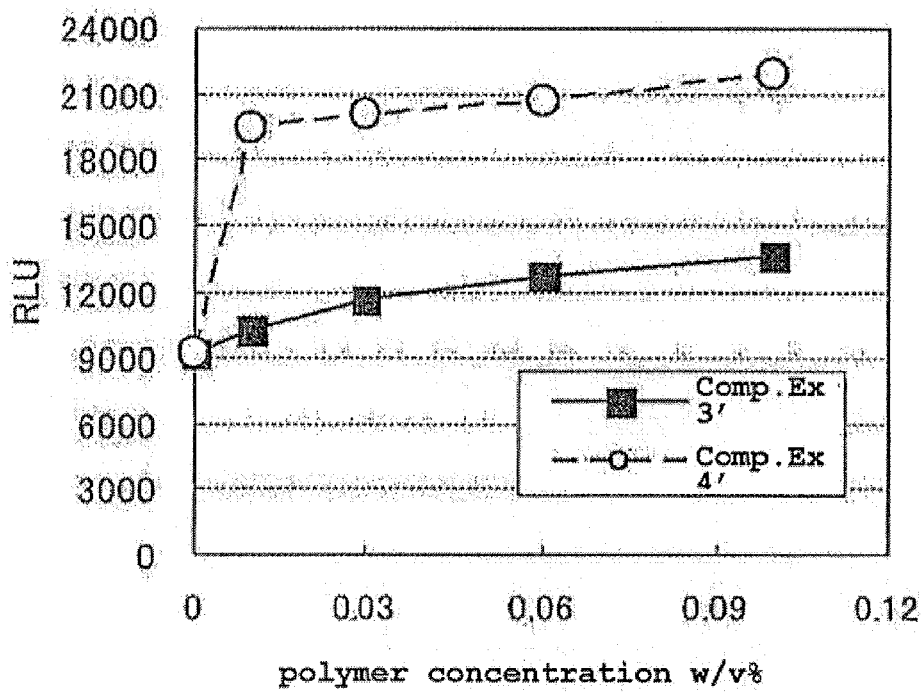

FIG. 33 shows RLU value on day 6 from the start of the suspension culture of MCF7 cells in the medium compositions of Comparative Examples 3' and 4'.

Figure 34:
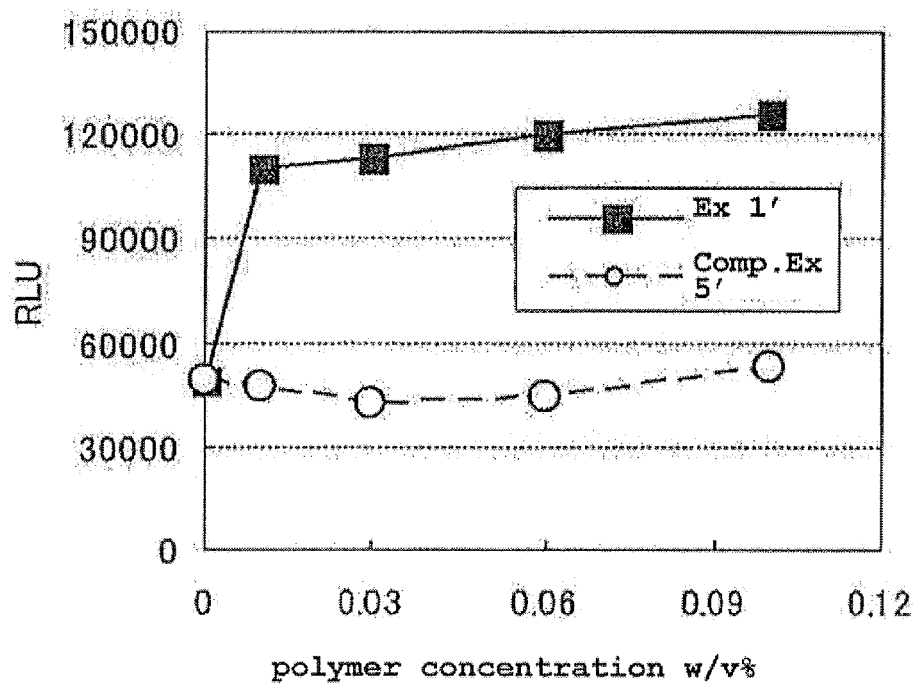

FIG. 34 shows RLU value on day 6 from the start of the suspension culture of A375 cells in the medium compositions of Example 1' and Comparative Example 5'.

Figure 35:
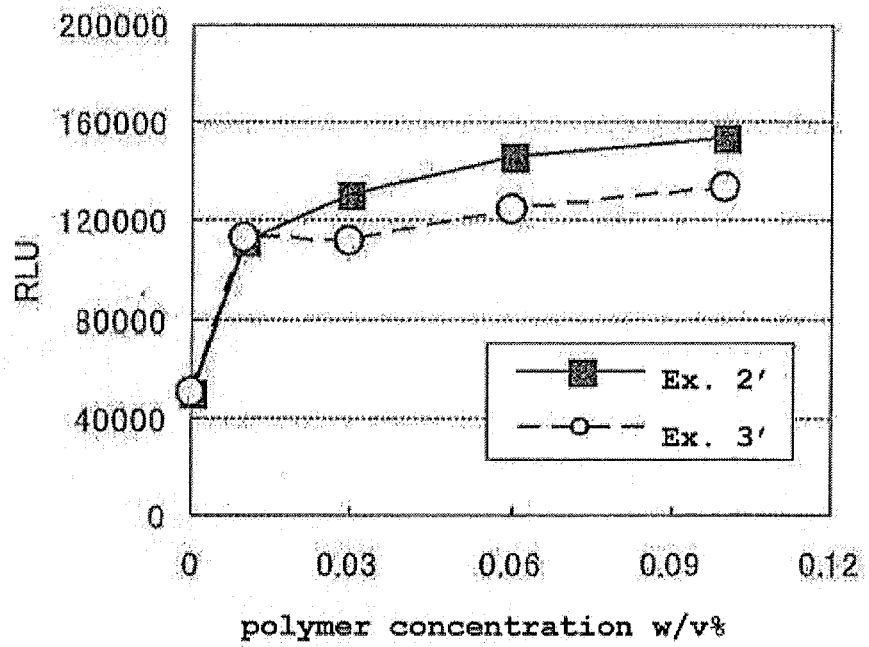

FIG. 35 shows RLU value on day 6 from the start of the suspension culture of A375 cells in the medium compositions of Examples 2' and 3'.

Figure 36:
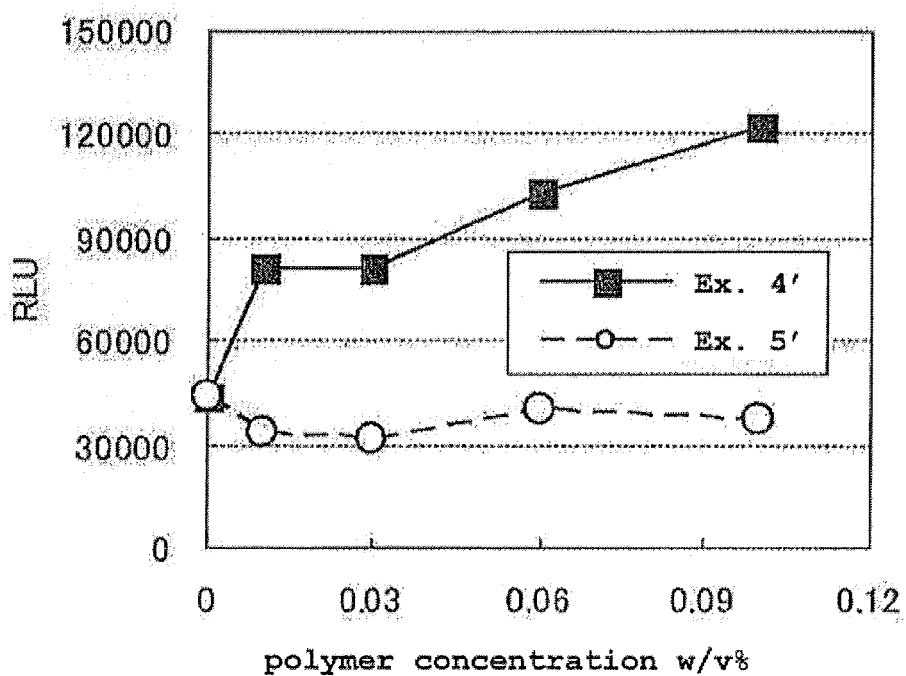

FIG. 36 shows RLU value on day 6 from the start of the suspension culture of A375 cells in the medium compositions of Examples 4' and 5'.

Figure 37:
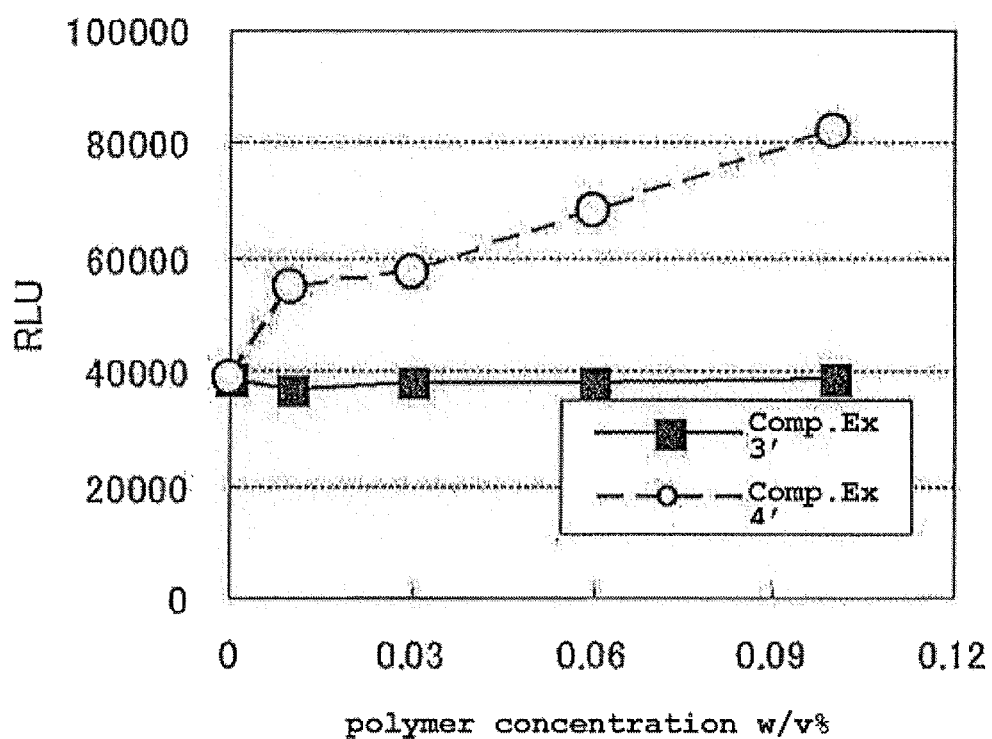

FIG. 37 shows RLU value on day 6 from the start of the suspension culture of A375 cells in the medium compositions of Comparative Examples 3' and 4'.

FIG. 38 shows the results of microscopic observation of the dispersion state of MCF7 cells on day 2 from the start of the suspension culture in each medium composition.

Figure 39:
Figure 39:
Figure 39:
Figure 39:
Figure 39:
Figure 39:
Figure 39:
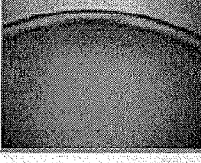
Figure 39:
Figure 39:
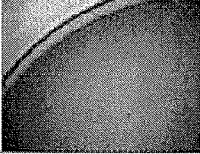
Figure 39:
Figure 39:
Figure 39:
Figure 39:
Figure 39:
Figure 39:
Figure 39:
Figure 39:
Figure 39:
Figure 39:
Figure 39:
Figure 39:
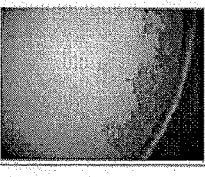
Figure 39:
Figure 39:
Figure 39:
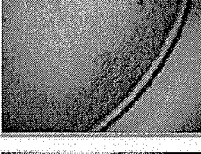
Figure 39:
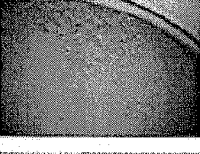
Figure 39:
Figure 39:
Figure 39:
Figure 39:
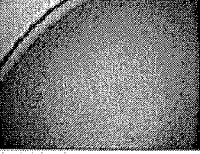
Figure 39:
Figure 39:
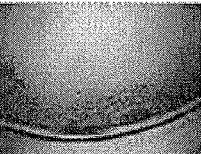
Figure 39:
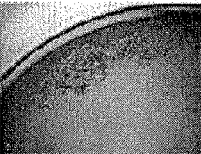
Figure 39:

FIG. 39 shows the results of microscopic observation of the dispersion state of A375 cells on day 2 from the start of the suspension culture in each medium composition.

Figure 40:
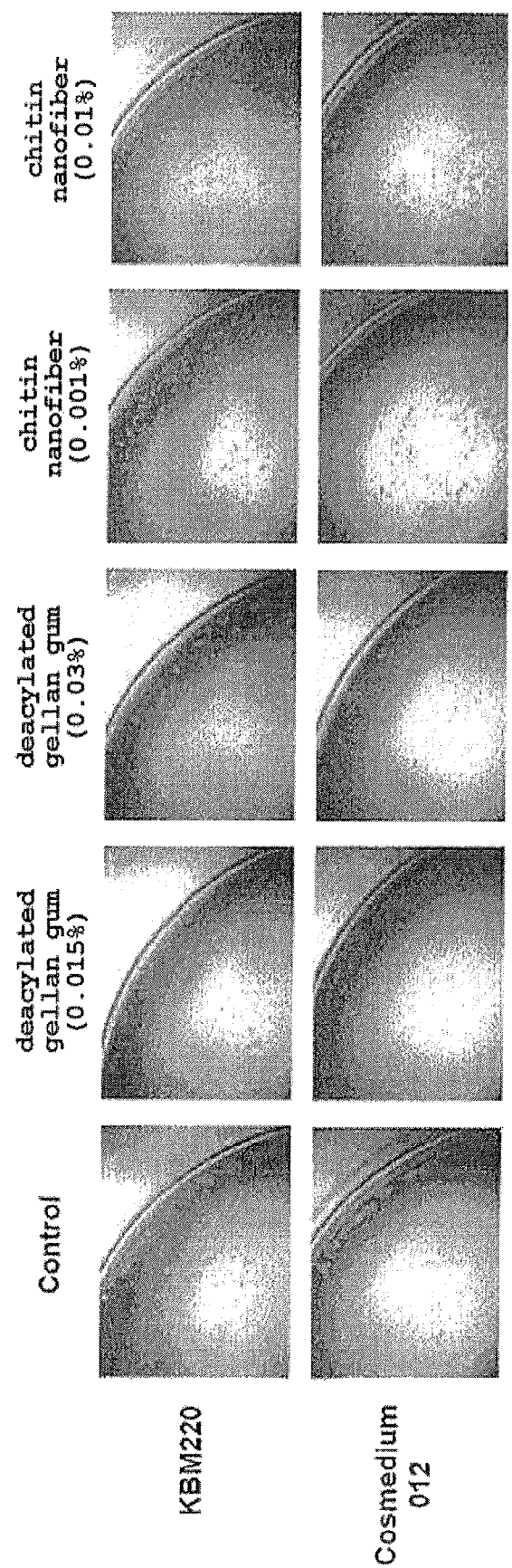

FIG. 40 shows the results of microscopic observation of the dispersion state of MDCK cells on day 4 from the start of the suspension culture in each medium composition.

DESCRIPTION OF EMBODIMENTS

The present invention is explained in more detail in the following.

The terms used in the present specification are defined as follows.

The cell in the present invention is a most basic unit constituting animals and plants, which has, as its elements, cytoplasm and various organelles inside the cellular membrane. In this case, the nucleus encapsulating the DNA may or may not be contained intracellularly. For example, the animal-derived cells in the present invention include reproductive cells such as spermatozoon, oocyte and the like, somatic cells constituting the living body, stem cells, progenitor cells, cancer cells separated from the living body, cells separated from the living body, which acquired immortalizing ability and is maintained stably in vitro (cell line), cells separated from the living body and applied with artificial genetic modification, cells separated from the living body wherein the nucleus is artificially exchanged, and the like. Examples of the somatic cells constituting the living body include, but are not limited to, fibroblast, bone marrow cells, B lymphocytes, T lymphocytes, neutrophils, red blood cells, platelets, macrophages, monocytes, osteocytes, bone marrow cells, pericytes, dendritic cells, keratinocytes, adipocytes, mesenchymal cells, epithelial cells, epidermal cells, endothelial cells, vascular endothelial cells, hepatocytes, chondrocytes, cumulus cells, nerve system cells, glial cells, neurons, oligodendrocytes, microglial, astrocytes, heart cells, esophagus cells, myocytes (e.g., smooth muscle cells or skeletal muscle cells), pancreatic beta cells, melanin cells, hematopoietic progenitor cells, mononuclear cells and the like. The somatic cells include cells collected from any tissue, for example, skin, kidney, spleen, adrenal gland, liver, lung, ovary, pancreas, uterus, stomach, colon, small intestine, large intestine, spleen, bladder, prostate, testis, thymus, muscle, connective tissue, bone, cartilage, blood vessel tissue, blood, heart, eye, brain, nerve tissue and the like. Stem cells are cells concurrently having an ability to replicate itself, and an ability to differentiate into other plural lineages. Examples thereof include, but are not limited to, embryonic stem cells (ES cell), embryonic tumor cells, embryonic reproductive stem cells, artificial pluripotent stem cells (iPS cell), neural stem cells, hematopoietic stem cells, mesenchymal stem cells, liver stem cells, pancreas stem cells, muscle stem cells, reproductive stem cells, intestinal stem cells, cancer stem cells, hair follicle stem cells and the like. Progenitor cells are cells on the way to differentiate from the aforementioned stem cell into a particular somatic cell or reproductive cell. Cancer cells are cells that are derived from a somatic cell and have acquired infinite proliferative capacity. Cell lines are cells that have acquired infinite proliferative capacity by an artificial operation in vitro, and examples thereof include, but are not limited to, CHO (Chinese hamster ovary cell line), HCT116, Huh7, HEK293 (human embryonic kidney cell), HeLa (human uterine cancer cell line), HepG2 (human liver cancer cell line), UT7/TPO (human leukemia cell line), MDCK, MDBK, BHK, C-33A, HT-29, AE-1, 3D9, Ns0/1, Jurkat, NIH3T3, PC12, S2, Sf9, Sf21, High Five (registered trade mark), Vero and the like.

The plant-derived cell in the present invention also includes cells separated from each tissue of a plant body, as well as a protoplast obtained by artificially removing the cell wall from the cell.

The tissue in the present invention is a unit of a structure which is an assembly in a certain manner of cells having some kinds of different properties and functions, and examples of the animal tissue include epithelial tissue, connective tissue, muscular tissue, nerve tissue and the like. Examples of the plant tissue include meristem, epidermis tissue, assimilation tissue, mesophyll tissue, conductive tissue, mechanical tissue, parenchyma tissue, dedifferentiated cell cluster (callus) and the like.

When cells and/or tissues are cultivated, the cells and/or tissues to be cultivated can be selected freely from the cells and/or tissues described above and cultivated. The cells and/or tissues can be directly recovered from an animal or plant body. The cells and/or tissues may be induced, grown or transformed from an animal or plant body by applying a particular treatment and then collected. In this case, the treatment may be in vivo or in vitro. Examples of the animal include fish, amphibian, reptiles, birds, pancrustacea, hexapoda, mammals and the like. Examples of the mammal include, but are not limited to, rat, mouse, rabbit, guinea pig, squirrel, hamster, vole, platypus, dolphin, whale, dog, cat, goat, bovine, horse, sheep, swine, elephant, common marmoset, squirrel monkey, Macaca mulatta, chimpanzee and human. The plant is not particularly limited as long as the collected cells and/or tissues can be applied to liquid culture. Examples thereof include, but are not limited to, plants (e.g., ginseng, periwinkle, henbane, coptis, belladonna etc.) producing crude drugs (e.g., saponin, alkaloids, berberine, scopolin, phytosterol etc.), plants (e.g., blueberry, safflower, madder, saffron etc.) producing dye or polysaccharide (e.g., anthocyanin, safflower dye, madder dye, saffron dye, flavones etc.) to be a starting material for cosmetic or food, or plants producing a pharmaceutical drug substance and the like.

Suspending of cells and/or tissues in the present invention refers to a state where cells and/or tissues do not adhere to a culture container (non-adhesive). Furthermore, in the present invention, when the cells and/or tissues are proliferated, differentiated or maintained, the state where the cells and/or tissues are uniformly dispersed and suspended in the liquid medium composition in the absence of a pressure on or vibration of the liquid medium composition from the outside or shaking, rotating operation and the like in the composition is referred to as "suspension standing", and cultivation of the cells and/or tissues in such condition is referred to as "suspension standing culture". In the "suspension standing", the period of suspending includes at least 5 min, preferably, not less than 1 hr, not less than 24 hr, not less than 48 hr, not less than 6 days, not less than 21 days, though the period is not limited thereto as long as the suspended state is maintained.

In a preferable embodiment, the medium composition of the present invention permits suspension standing of cells and/or tissues at least on one point in the temperature range (e.g., 0-40° C.) capable of maintaining or culturing cells and tissues. The medium composition of the present invention permits suspension standing of cells and/or tissues at least on one point in the temperature range of preferably 25-37° C., most preferably 37° C.

Whether or not suspension standing is possible can be evaluated by, for example, uniformly dispersing polystyrene beads (Size 500-600 μm, manufactured by Polysciences Inc.) in a medium composition to be the evaluation target, standing same at 25° C., and observing whether the suspended state of the cell can be maintained for at least 5 min (preferably, not less than 24 hr, not less than 48 hr).

The medium composition of the present invention is a composition containing a nanofiber capable of culturing cells or tissues in a suspended state (preferably capable of suspension standing culture) and a medium.

The medium composition is preferably a composition permitting an exchange treatment of the medium composition during culture, and recovery of the cells or tissues after completion of the culture. More preferably, it is a medium composition that allows for recovery of the cells or tissues without any of a temperature change, a chemical treatment, an enzyme treatment and a shear force.

[Nanofiber]

The nanofiber to be contained in the medium composition of the present invention shows an effect of uniformly suspending cells and/or tissues in a liquid medium. More particularly, a nanofiber formed in a liquid medium by low-molecular-weight compounds or polymer compounds that were assembled and self-organized via a covalent bond or ionic bond, electrostatic interaction, hydrophobic interaction, Van der Waals' force and the like, a nanofiber obtained by subdividing a comparatively large fiber structure composed of a polymer compound by a high-pressure treatment and the like, and the like can be recited as the nanofiber to be contained in the medium composition of the present invention. While not bound by theory, nanofibers form a three dimensional network and support cells and tissues in the medium composition of the present invention, thereby maintaining the cells and tissues in a suspended state.

In the present specification, nanofiber refers to a fiber having an average fiber diameter (D) of 0.001 to 1.00 μm. The average fiber diameter of the nanofiber to be used in the present invention is preferably 0.005 to 0.50 μm, more preferably 0.01 to 0.05 μm, further preferably 0.01 to 0.02 μm. When the average fiber diameter is less than 0.001 μm, the nanofiber becomes too fine and the suspending effect may not be achieved, and the property of the medium composition containing same may not be improved.

The aspect ratio (L/D) of the nanofiber to be used in the present invention is obtained from average fiber length/average fiber diameter, and is generally 2-500, preferably 5-300, more preferably 10-250. When the aspect ratio is less than 2, dispersibility in the medium composition may be absent and a sufficient suspending action may not be obtained. When it exceeds 500, it means that the fiber length becomes extremely large, in which case an increased viscosity of the composition may prevent passage operations such as medium exchange and the like. In addition, since the medium composition does not allow easy permeation of visible light, the transparency becomes low, time-course observation of the cultured cells becomes difficult, and cell evaluation using light absorption, fluorescence, luminescence and the like may be impaired.

In the present specification, the average fiber diameter (D) of the nanofiber was determined as follows. First, a hydrophilizing treatment of a collodion support film manufactured by Okenshoji Co., Ltd. was performed for 3 min by an ion creaner (JIC-410) manufactured by JEOL Ltd., several drops of a nanofiber dispersion (diluted with ultrapure water) to be the evaluation target was added dropwise, and dried at room temperature. This was observed under a transmission electron microscope (TEM, H-8000) (10,000-fold) manufactured by Hitachi, Ltd. at an accelerating voltage 200 kV. Using the obtained image, the fiber diameter of each one of the nanofibers (specimen number: 200-250) was measured, and the mean thereof was taken as the average fiber diameter (D).

In addition, the average fiber length (L) was determined as follows. A nanofiber dispersion to be the evaluation target was diluted to 100 ppm with pure water, and nanofibers were uniformly dispersed using an ultrasonic cleaner. The nanofiber dispersion was cast on a silicon wafer subjected in advance to a hydrophilizing treatment of the surface with concentrated sulfuric acid, dried at 110° C. for 1 hr and used as a sample. Using an image obtained by observing the obtained sample under a scanning electron microscope (SEM, JSM-7400F) (2,000-fold), the fiber length of each one of the nanofibers (specimen number: 150-250) was measured, and the mean thereof was taken as the average fiber length (L).

The nanofiber to be used in the present invention is, upon mixing with a liquid medium, uniformly dispersed in the liquid while maintaining the primary fiber diameter, substantially retains the cells and/or tissues without substantially increasing the viscosity of the liquid, and shows an effect of preventing sediment thereof. The "without substantially increasing the viscosity of the liquid" means that the viscosity of the liquid does not exceed 8 mPa·s. In this case, the viscosity of the liquid (that is, the viscosity of the medium composition to be produced by the production method of the present invention) is not more than 8 mPa·s, preferably not more than 4 mPa·s, more preferably not more than 2 mPa·s. Furthermore, the chemical structure, molecular weight, property etc. of the nanofiber are not limited as long as, when dispersed in a liquid medium, it shows an effect of uniformly suspending (preferably suspension standing) the cells and/or tissues without substantially increasing the viscosity of the liquid.

The viscosity of the liquid containing the nanofiber can be measured, for example, by the method described in the below-mentioned Examples. Specifically, it can be evaluated using a tuning fork vibration type viscometer (SV-1A, A&D Company Ltd.) under 25° C. conditions.

While the starting material constituting the nanofiber is not particularly limited, low-molecular-weight compounds and polymer compounds can be mentioned.

Specific preferable examples of the low-molecular-weight compound to be used in the present invention include, but are not limited to, amino acid derivatives such as L-isoleucine derivative, L-valine derivative, L-lysine derivative and the like, cyclohexanediamine derivatives such as trans-1,2-diaminocyclohexanediamide derivative and the like, and low molecule gellants such as 5-aminoisophthalic acid derivative, R-12-hydroxystearic acid, 1,3,5-benzenetricarboxamide, cis-1,3,5-cyclohexanetricarboxamide, 2,4-dibenzylidene-D-sorbitol, N-lauroyl-L-glutamic acid-α,γ-bis-n-butylamide, calcium dehydroabietate and the like.

Specific preferable examples of the polymer compound to be used in the present invention include, but are not limited to, polysaccharides, polypeptides and the like.

Polysaccharides mean glycopolymers wherein not less than 10 single saccharides (e.g., triose, tetrose, pentose, hexsauce, heptose etc.) are polymerized. Polysaccharides encompass non-water-soluble polysaccharides and water-soluble polysaccharides.

Examples of the 非 water-soluble polysaccharides include, but are not limited to, celluloses such as cellulose, hemicellulose and the like; chitinous substances such as chitin, chitosan and the like, and the like.

Examples of the water-soluble polysaccharides include acidic polysaccharides having an anionic functional group.

The acidic polysaccharides having an anionic functional group are not particularly limited and include, for example, polysaccharides having a uronic acid (e.g., glucuronic acid, iduronic acid, galacturonic acid, mannuronic acid) in the structure, polysaccharides having sulfuric acid or phosphate in the structure, and polysaccharides having the both structures and the like. More specifically, examples thereof include polymer compounds composed of one or more kinds selected from the group consisting of hyaluronic acid, gellan gum, deacylated gellan gum (DAG), rhamsan gum, diutan gum, xanthan gum, carageenan, xanthan gum, hexuronic acid, fucoidan, pectin, pectic acid, pectinic acid, heparan sulfate, heparin, heparitin sulfate, keratosulfate, chondroitin sulfate, dermatan sulfate, rhamnan sulfate, alginic acid and a salt thereof.

Examples of the salt here include alkali metal salts such as lithium, sodium, potassium; alkaline earth metal salts such as calcium, barium, magnesium; salts such as aluminum, zinc, copper, iron and the like; ammonium salt; quaternary ammonium salts such as tetraethylammonium, tetrabutylammonium, methyltributylammonium, cetyl trimethylammonium, benzylmethylhexyldecylammonium, choline and the like; salts with organic amines such as pyridine, triethylamine, diisopropylamine, ethanolamine, diolamine, tromethamine, meglumine, procaine, chloroprocaine and the like; salts with amino acid such as glycine, alanine, valine and the like; and the like.

As polypeptide, polypeptide constituting fiber in living organisms can be mentioned. Specific examples thereof include, but are not limited to, collagen, elastin, myosin, keratin, amyloid, fibroin, actin, tubulin and the like.

The starting material constituting the nanofiber to be used in the present invention includes not only naturally-derived substances but also substances produced by microorganisms, genetically-engineered substances, and substances artificially synthesized using enzymes and chemical reactions. The starting material constituting the nanofiber to be used in the present invention is preferably a naturally-derived substance (i.e., naturally-extracted substance), or a substance obtained by modifying same by chemical reaction or enzyme reaction.

In one embodiment, polysaccharides are non-water-soluble polysaccharides. Preferable non-water-soluble polysaccharide includes cellulose; and chitinous substances such as chitin, chitosan and the like. Cellulose and chitin are most preferable, since the viscosity of the medium composition can be made low and the cells or tissues can be recovered easily.

Cellulose is a natural polymer compound wherein D-glucopyranoses which are a 6-membered ring of glucose, are β-1,4 glucoside bonded. As the starting material, for example, plant-derived cellulose such as lumber, bamboo, hemp, jute, kenaf, cotton, agricultural crops•food residue and the like, or cellulose of microorganism production or animal production such as bacterial cellulose, Cladophora, Glaucocystis, Valonia, Tunicate cellulose and the like can be used. In the plant-derived celluloses, very fine fibers called microfibrils are bundled to form higher structures in stages such as fibril, lamella and fibre cell. In addition, in bacterial cellulose, cellulose microfibrils secreted from bacterial cells and having the unchanged thickness form a fine net structure.

In the present invention, cellulose starting material having high purity such as cotton, bacterial cellulose and the like can be directly used. However, other plant-derived cellulose and the like are preferably used after isolation and purification. Cellulose preferably used in the present invention includes cotton cellulose, bacterial cellulose, kraft pulp cellulose, microcrystalline cellulose and the like. Kraft pulp cellulose is particularly preferably used, since it has a high suspending action.

The chitinous substance refers to one or more carbohydrates selected from the group consisting of chitin and chitosan. Major sugar units constituting chitin and chitosan are N-acetylglucosamine and glucosamine, respectively. Generally, chitin has a high N-acetylglucosamine content and is poorly soluble in acidic aqueous solution, and chitosan has a high glucosamine content and is soluble in acidic aqueous solution. For convenience, chitin contains not less than 50% of N-acetylglucosamine in the constituent sugar, and chitosan contains less than 50% of N-acetylglucosamine in the present specification. To achieve a high suspending action, a higher ratio of N-acetylglucosamine in the sugar unit constituting chitin is more preferable. The ratio of N-acetylglucosamine in the sugar unit constituting chitin is preferably not less than 80%, more preferably not less than 90%, further preferably not less than 98%, most preferably 100%.

As the starting material of chitin, many biological resources such as shrimps, crabs, insect, shells, mushrooms and the like can be used. The chitin to be used in the present invention may be one having α-formcrystal structure such as chitin derived from crab shell, shrimp shell and the like, or one having β-form crystal structure such as chitin derived from cuttlebones and the like. The test of crabs and shrimps is often regarded as industrial waste and preferable as a starting material since it is easily available and effectively used. On the other hand, it requires a protein removing step and a decalcification step to remove protein, minerals and the like contained as impurities. In the present invention, therefore, purified chitin that underwent a matrix removal treatment is preferably used. Purified chitin is commercially available.

In one embodiment, polysaccharide is a water-soluble polysaccharide. Preferable examples of the water-soluble polysaccharide include deacylated gellan gum, carageenan and the like. To achieve a high suspending action, deacylated gellan gum is most preferable.

The deacylated gellan gum is a linear polymer polysaccharide containing 4 molecules of sugars of 1-3 bonded glucose, 1-4 bonded glucuronic acid, 1-4 bonded glucose and 1-4 bonded rhamnose as the constituent unit, which is a polysaccharide of the following formula (I) wherein R1, R2 are each a hydrogen atom, and n is an integer of two or more. R1 may contain a glyceryl group, R2 may contain an acetyl group, and the content of the acetyl group and glyceryl group is preferably not more than 10%, more preferably not more than 1%.

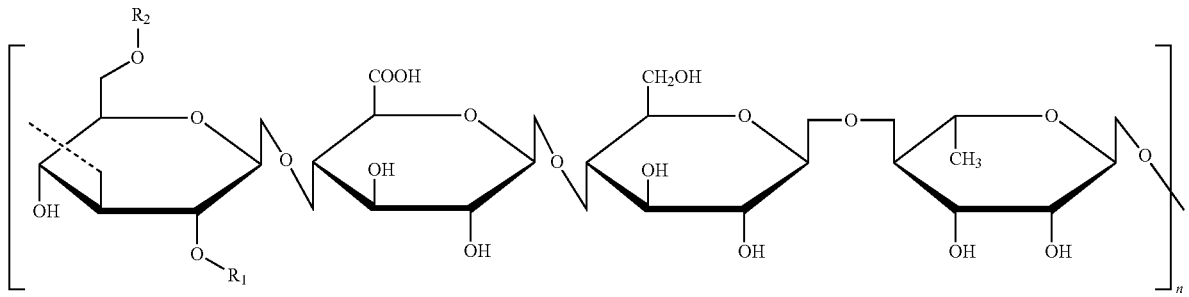

(I)

As a production method of gellan gum, a producing microorganism is cultured in a fermentation medium, a mucosal substance produced outside fungus is recovered by a general purification method and, after the steps of drying, pulverizing and the like, powderized. Deacylated gellan gum is obtained by culturing a microorganism that produces gellan gum in a fermentation medium, and recovering mucosa secretion produced outside fungus. In this case, an alkali treatment is applied when a mucous substance is recovered, the glyceryl group and the acetyl group bonded to 1-3 bonded glucose residue are deacylated and recovered. Purification of deacylated gellan gum from the recovered mucosa secretion includes, for example, include liquid-liquid extraction, fractional precipitation, crystallization, various kinds of ion exchange chromatography, gel filtration chromatography using Sephadex LH-20 and the like, adsorption chromatography using activated carbon, silica gel and the like, adsorption and desorption treatment of active substance by thin layer chromatography, high performance liquid chromatography using reversed-phase column and the like, which can be performed singly or in combination in any order, or repeatedly. Examples of the gellan gum-producing microorganism include, but are not limited to, *Sphingomonas elodea* and microorganisms obtained by altering the gene of *Sphingomonas elodea*.

When it is deacylated gellan gum, commercially available products, for example, "KELCOGEL (registered trade mark of CP Kelco) CG-LA" manufactured by SANSHO Co., Ltd., "KELCOGEL (registered trade mark of CP Kelco)" manufactured by San-Ei Gen F.F.I., Inc. and the like can be used.

The weight average molecular weight of the polymer compound to be used in the present invention is preferably 1,000 to 50,000,000, more preferably 10,000 to 20,000,000, further preferably 100,000 to 10,000,000. For example, the molecular weight can be estimated from polyethylene glycol by gel penetration chromatography (GPC), pullulan conversion, viscosity of aqueous solution and the like.

In the present invention, plural kinds (preferably two kinds) of the above-mentioned polymer compounds can be used in combination. The kind of the combination of the polymer compound is not particularly limited as long as the nanofiber is formed or dispersed as nanofibers in a liquid medium, and the cells and/or tissues can be suspended (preferably suspension stood) without substantially increasing the viscosity of the liquid medium. Preferably, the combination includes at least cellulose, chitin, collagen, or deacylated gellan gum. That is, a preferable combination of polymer compound includes cellulose, chitin, collagen, or deacylated gellan gum; and other polymer compound (e.g., xanthan gum, alginic acid, carageenan, diutan gum, methylcellulose, locust bean gum or a salt thereof).

[Preparation of Nanofiber]

The medium composition of the present invention contains a nanofiber prepared from the aforementioned starting material. The preparation method of nanofiber varies between when a non-water-soluble polymer compound (e.g., non-water-soluble polysaccharides such as cellulose, chitin and the like) is used as a starting material, and when a water-soluble polymer compound (e.g., water-soluble polysaccharides such as deacylated gellan gum and the like) is used as a starting material.

When the starting material of nanofiber is a non-water-soluble polymer compound (e.g., non-water-soluble polysaccharides such as cellulose, chitin and the like), the nanofiber is generally obtained by pulverizing the starting material. While the pulverization method is not limited, a method affording a strong shear force such as a medium stirring mill, for example, a high-pressure homogenizer, a grinder (stone mill), a beadmill and the like is preferable for subdivision to the below-mentioned fiber diameter and fiber length meeting the object of the present invention.

Of these, subdivision by a high-pressure homogenizer is preferable, and, for example, subdivision (pulverization) by the wet pulverization method disclosed in JP-A-2005-270891 or JP-B-5232976 is desirable. Specifically, the starting material is pulverized by spraying a dispersion of a starting material from a pair of nozzles at a high-pressure and bombarding each other, and, for example, Star Burst-system (high-pressure pulverization device manufactured by Sugino Machine Limited) or NanoVater (high-pressure pulverization device of yoshida kikai co., ltd) is used therefor.

In the subdivision (pulverization) of a starting material by the aforementioned high-pressure homogenizer, the degree of subdivision and homogenization depends on the pressure in pumping into an ultrahigh-pressure chamber in a high-pressure homogenizer, and the number (treatment number) of passage through the ultrahigh-pressure chamber, and the concentration of the starting material in the water dispersion. The pumping pressure (treatment pressure) is generally, 50-250 MPa, preferably 150-245 MPa. When the pumping pressure is less than 50 MPa, subdivision of nanofiber is insufficient, and the effect expected from subdivision may not be achieved.

The concentration of the starting material in a water dispersion during the subdividing treatment is 0.1 mass %-30 mass %, preferably 1 mass %-10 mass %. When the concentration of the starting material in the water dispersion is less than 0.1 mass %, the producibility becomes low and, when the concentration is higher than 30 mass %, pulverization efficiency becomes low and the desired nanofiber cannot be achieved. While the treatment number of the subdivision (pulverization) is not particularly limited, it varies depending on the concentration of the starting material in the aforementioned water dispersion. When the concentration of the starting material is 0.1-1 mass %, the treatment number of 10-100 is sufficient for pulverization, but 1-10 mass % requires about 10-1000 times of treatment. A high concentration exceeding 30 mass % requires several thousand times of treatment, and increases the viscosity too high to perform normal handling, it is industrially impractical.

When the starting material of nanofiber includes a water-soluble polymer compound (e.g., water-soluble polysaccharides such as deacylated gellan gum and the like), addition of the substance to the medium results in the assembly of the substance via a metal cation in the medium to form a nanofiber in the medium, which in turn constructs a three dimensional network. As a result, nanofibers capable of culturing cells or tissues in a suspended state can be formed.

The concentration of the nanofiber in the medium composition of the present invention can be appropriately determined so that the cells and/or tissues can be suspended (preferably suspension stood) without substantially increasing the viscosity of the medium. It is generally 0.0001% to 1.0% (weight/volume), for example, 0.0005% to 1.0% (weight/volume), preferably 0.001% to 0.5% (weight/volume), more preferably 0.005% to 0.1% (weight/volume), further preferably 0.005% to 0.05% (weight/volume).

For example, in the case of a cellulose nanofiber, it is generally added to a medium at 0.0001% to 1.0% (weight/volume), for example, 0.0005% to 1.0% (weight/volume), preferably 0.001% to 0.5% (weight/volume), more preferably 0.01% to 0.1% (weight/volume), further preferably, 0.01% to 0.05% (weight/volume).

In the case of a pulp cellulose nanofiber from the cellulose nanofibers, the lower limit of the concentration in the medium is preferably not less than 0.01% (weight/volume), not less than 0.015% (weight/volume), not less than 0.02% (weight/volume), not less than 0.025% (weight/volume), or not less than 0.03% (weight/volume), from the aspects of expression of suspending action and enablement of suspension stand culture. In the case of a pulp cellulose nanofiber, the upper limit of the concentration in the medium is preferably not more than 0.1% (weight/volume) or not more than 0.04% (weight/volume) to prevent substantial increase in the medium viscosity.

In the case of a microcrystalline cellulose nanofiber, the lower limit of the concentration in the medium is preferably not less than 0.01% (weight/volume), not less than 0.03% (weight/volume), or not less than 0.05% (weight/volume) from the aspects of expression of the suspending action. To enable suspension stand culture, the lower limit of the concentration of microcrystalline cellulose nanofiber in the medium is preferably not less than 0.03% (weight/volume), or not less than 0.05% (weight/volume). In the case of a microcrystalline cellulose nanofiber, the upper limit of the concentration in the medium is preferably not more than 0.1% (weight/volume).

In the case of a chitin nanofiber, it is added to the medium generally at 0.0001% to 1.0% (weight/volume), for example, 0.0005% to 1.0% (weight/volume), preferably 0.001% to 0.5% (weight/volume), more preferably 0.01% to 0.1% (weight/volume), most preferably, 0.03% to 0.07% (weight/volume). From the aspects of expression of a suspending action, the lower limit of the concentration of chitin nanofiber in the medium is preferably not less than 0.0001% (weight/volume), not less than 0.0003% (weight/volume), not less than 0.0005% (weight/volume), or not less than 0.001% (weight/volume). To enable suspension stand culture, the lower limit of chitin nanofiber in the medium is preferably not less than 0.03% (weight/volume). The upper limit of chitin nanofiber in the medium is preferably not more than 0.1% (weight/volume).

In the case of a non-water-soluble nanofiber such as cellulose nanofiber, chitin nanofiber and the like, a concentration not more than 0.1% (weight/volume) generally does not substantially increase the viscosity of the medium composition.

In the case of carageenan, it is added to the medium at 0.0005% to 1.0% (weight/volume), preferably 0.001% to 0.5% (weight/volume), more preferably 0.01% to 0.1% (weight/volume), most preferably, 0.02% to 0.1% (weight/volume). The lower limit of carageenan concentration in medium is preferably not less than 0.01%. The upper limit of the carageenan concentration in the medium is preferably not more than 0.1% (weight/volume) from the aspects of expression of the suspending action and enablement of suspension standing culture. The upper limit of carageenan is also preferably set to not more than 0.04% (weight/volume) to prevent substantial increase in the medium viscosity.

In the case of deacylated gellan gum, it is generally added to the medium at 0.001% to 1.0% (weight/volume), for example, 0.005% to 1.0% (weight/volume), preferably 0.003% to 0.5% (weight/volume), more preferably 0.01% to 0.1% (weight/volume), further preferably 0.01 to 0.05% (weight/volume), most preferably 0.01% to 0.02% (weight/volume). From the aspects of expression of a suspending action, the lower limit of the concentration of deacylated gellan gum in the medium is preferably not less than 0.005% (weight/volume), or not less than 0.01%. To enable suspension standing culture, the lower limit of the concentration of deacylated gellan gum in the medium is preferably not less than 0.01% (weight/volume). To prevent substantial increase in the medium viscosity, the upper limit of the concentration of deacylated gellan gum in the medium is not more than 0.05% (weight/volume). To prevent substantial increase in the medium viscosity, the upper limit of the concentration of deacylated gellan gum in the medium is also preferably set to not more than 0.04 (weight/volume) %.

[Combined Use of Polysaccharides]

In addition to the above-mentioned nanofiber, plural kinds (preferably two kinds) of polysaccharides can also be used in combination. The concentration of the polysaccharides can be set appropriately as long as the cells and/or tissues can be uniformly suspended (preferably suspension stand) without substantially increasing the viscosity of the liquid medium. For example, when a combination of nanofiber and polysaccharide is used, the concentration of nanofiber is, for example, 0.005-0.1% (weight/volume), preferably 0.01-0.07% (weight/volume), and the concentration of polysaccharide is, for example, 0.005-0.4% (weight/volume), preferably 0.1-0.4% (weight/volume). Specific examples of the combination of the concentration range include the following.

cellulose or chitin nanofiber: 0.005-0.1% (preferably 0.01-0.07%) (weight/volume)

polysaccharides xanthan gum: 0.1-0.4% (weight/volume)

sodium alginate: 0.1-0.4% (weight/volume) (preferably 0.0001-0.4% (weight/volume))

locust bean gum: 0.1-0.4% (weight/volume)

methylcellulose: 0.1-0.4% (weight/volume) (preferably 0.2-0.4% (weight/volume))

carageenan: 0.05-0.1% (weight/volume)
diutan gum: 0.05-0.1% (weight/volume)
native gellan gum: 0.0001-0.4% (weight/volume)

The concentration can be calculated by the following formula.

Concentration (%)=weight (g) of nanofiber/volume (ml) of medium composition×100

[Metal Cation]

In one embodiment, the medium composition of the present invention contains metal cations, for example, divalent metal cation (calcium ion, magnesium ion, zinc ion, iron ion and copper ion etc.), preferably calcium ion. Particularly, when the nanofiber contained in the medium composition of the present invention is constituted of a water-soluble polymer compound (e.g., water-soluble polysaccharides such as deacylated gellan gum and the like), the medium composition of the present invention preferably contains the above-mentioned metal cation. When a metal cation is contained, an assembly of the water-soluble polymer compound (e.g., water-soluble polysaccharides such as deacylated gellan gum and the like) is formed via the metal cation in the medium composition to form a nanofiber, which in turn constructs a three dimensional network. As a result, nanofibers capable of culturing cells or tissues in a suspended state can be formed.

[Medium]

Examples of the medium to be contained in the medium composition of the present invention include Dulbecco's Modified Eagle's Medium (DMEM), hamF12 medium (Ham's Nutrient Mixture F12), DMEM/F12 medium, McCoy's 5A medium, Eagle MEM medium (Eagle's Minimum Essential Medium; EMEM), αMEM medium (alpha Modified Eagle's Minimum Essential Medium; αMEM), MEM medium (Minimum Essential Medium), RPMI1640 medium, Iscove's Modified Dulbecco's Medium (IMDM), MCDB131 medium, William medium E, IPL41 medium, Fischer's medium, StemPro34 (manufactured by Invitrogen), X-VIVO 10 (manufactured by Cambrex Corporation), X-VIVO 15 (manufactured by Cambrex Corporation), HPGM (manufactured by Cambrex Corporation), StemSpan H3000 (manufactured by STEMCELL Technologies), StemSpanSFEM (manufactured by STEMCELL Technologies), StemlineII (manufactured by Sigma Aldrich), QBSF-60 (manufactured by Qualitybiological), StemPro hESC SFM (manufactured by Invitrogen), mTeSR1 or 2 medium (manufactured by STEMCELL Technologies), Sf-900II (manufactured by Invitrogen), Opti-Pro (manufactured by Invitrogen), and the like.

When the cells and/or tissues are derived from a plant, a medium obtained by adding auxins and, where necessary, a plant growth control substance (plant hormone) such as cytokinins and the like at a suitable concentration to a basic medium such as Murashige Skoog (MS) medium, Linsmaier Skoog (LS) medium, White medium, Gamborg's B5 medium, niche medium, hela medium, Morel medium and the like generally used for culture of plant tissues, or a modified medium wherein these medium components are modified to an optimal concentration (e.g., ammonia nitrogen at a half concentration etc.) can be mentioned as the medium. These media can be further supplemented, where necessary, with casein degrading enzyme, corn steep liquor, vitamins and the like. Examples of the auxins include, but are not limited to, 3-indoleacetic acid (IAA), 3-indolebutyric acid (IBA), 1-naphthaleneacetic acid (NAA), 2,4-dichlorophenoxyacetic acid (2,4-D) and the like. For example, auxins can be added to a medium at a concentration of about 0.1-about 10 ppm. Examples of the cytokinins include, but are not limited to, kinetin, benzyladenine (BA), zeatin and the like. For example, cytokinins can be added to a medium at a concentration of about 0.1-about 10 ppm.

Those of ordinary skill in the art can freely add, according to the object, sodium, potassium, calcium, magnesium, phosphorus, chlorine, various amino acids, various vitamins, antibiotic, serum, fatty acid, sugar and the like to the above-mentioned medium. For culture of animal-derived cells and/or tissues, those of ordinary skill in the art can also add, according to the object, one or more kinds of other chemical components and biogenic substances in combination. Examples of the components to be added to a medium for animal-derived cells and/or tissues include fetal bovine serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various hormones, various proliferation factors, various extracellular matrices, various cell adhesion molecules and the like. Examples of the cytokine to be added to a medium include, but are not limited to, interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (IFN-α), interferon-β (IFN-β), interferon-γ (IFN-γ), granulocyte colony stimulating factor (G-CSF), monocyte colony stimulating agent (M-CSF), granulocyte-macrophage colony stimulating agent (GM-CSF), stem cell factor (SCF), flk2/flt3 ligand (FL), leukemia cell inhibitory factor (LIF), oncostatin M (OM), erythropoietin (EPO), thrombopoietin (TPO) and the like.

Examples of the hormone to be added to a medium include, but are not limited to, melatonin, serotonin, thyroxine, triiodothyronine, epinephrine, norepinephrine, dopamine, anti-Mullerian hormone, adiponectin, adrenocorticotropic hormone, angiotensinogen and angiotensin, antidiuretic hormone, atrial natriuretic peptide, calcitonin, cholecystokinin, corticotropin release hormone, erythropoietin, follicle stimulating hormone, gastrin, ghrelin, glucagon, gonadotropin release hormone, growth hormone release hormone, human chorionic gonadotropin, human placental lactogen, growth hormone, inhibin, insulin, insulin-like growth factor, leptin, luteinizing hormone, melanocyte stimulating hormone, oxytocin, parathyroid hormone, prolactin, secretin, somatostatin, thrombopoietin, thyroid gland stimulation hormone, thyrotropin releasing hormone, cortisol, aldosterone, testosterone, dehydroepiandrosterone, androstenedione, dihydrotestosterone, estradiol, estrone, estriol, progesterone, calcitriol, calcidiol, prostaglandin, leukotriene, prostacyclin, thromboxane, prolactin releasing hormone, lipotropin, brain natriuretic peptide, neuropeptide Y, histamine, endothelin, pancreas polypeptide, rennin and enkephalin.

Examples of the growth factor to be added to a medium include, but are not limited to, transforming growth factor-α (TGF-α), transforming growth factor-β (TGF-β), macrophage inflammatory protein-1α (MIP-1α), epithelial cell growth factor (EGF), fibroblast growth factor-1, 2, 3, 4, 5, 6, 7, 8 or 9 (FGF-1, 2, 3, 4, 5, 6, 7, 8, 9), nerve cell growth factor (NGF) hepatocyte growth factor (HGF), leukemia inhibitory factor (LIF), protease nexin I, protease nexin II, platelet-derived growth factor (PDGF), choline vasoactive differentiation factor (CDF), chemokine, Notch ligand (Delta1 and the like), Wnt protein, angiopoietin-like protein 2, 3, 5 or 7 (Angpt2, 3, 5, 7), insulin like growth factor (IGF), insulin-like growth factor binding protein-1 (IGFBP), Pleiotrophin and the like.

In addition, these cytokines and growth factors having amino acid sequences artificially altered by gene recombinant techniques can also be added. Examples thereof include IL-6/soluble IL-6 receptor complex, Hyper IL-6 (fusion protein of IL-6 and soluble IL-6 receptor) and the like.

Examples of the various extracellular matrices and various cell adhesion molecules include collagen I to XIX, fibronectin, vitronectin, laminin-1 to 12, nitogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, sepharose, hyaluronic acid, alginate gel, various hydrogels, cleavage fragments thereof and the like.

Examples of the antibiotic to be added to a medium include Sulfonamides and preparations, penicillin, phenethicillin, methicillin, oxacillin, cloxacillin, dicloxacillin, flucloxacillin, nafcillin, ampicillin, penicillin, amoxicillin, ciclacillin, carbenicillin, ticarcillin, piperacillin, azlocillin, mezlocillin, mecillinam, andinocillin, cephalosporin and a derivative thereof, oxolinic acid, amifloxacin, temafloxacin, nalidixic acid, Piromidic acid, ciprofloxacin, cinoxacin, norfloxacin, perfloxacin, Rosaxacin, ofloxacin, enoxacin, pipemidic acid, sulbactam, clavulanic acid, β-bromopenisillanic acid, β-chloropenisillanic acid, 6-acetylmethylene-penisillanic acid, cephoxazole, sultampicillin, adinoshirin and sulbactam formaldehyde hudrate ester, tazobactam, aztreonam, sulfazethin, isosulfazethin, norcardicin, m-carboxyphenyl, phenylacetamidophosphonic acid methyl, Chlortetracycline, oxytetracycline, tetracycline, demeclocycline, doxycycline, methacycline, and minocycline.

[Production Method of Medium Composition]

By mixing the above-mentioned nanofiber with a medium used for culturing cells and/or tissues to a concentration permitting uniform suspending (preferably suspension standing) of the cells and/or tissues without substantially increasing the viscosity of the liquid medium, the above-mentioned medium composition of the present invention can be produced. The present invention also provides a production method of the medium composition of the present invention.

The shape of the nanofiber is a formulated solid such as powder, tablet, pill, capsule, granule, a liquid such as a dispersion in an appropriate physiological aqueous solvent, or it may be bonded to a substrate or a single substance. Examples of the additive used for formulation include preservatives such as p-oxybenzoic acid esters and the like; excipients such as lactose, glucose, sucrose, mannit and the like; lubricants such as magnesium stearate, talc and the like; binders such as poly(vinyl alcohol), hydroxypropylcellulose, gelatin and the like; surfactants such as fatty acid ester and the like; plasticizers such as glycerol and the like; and the like. These additives are not limited to those mentioned above, and can be selected freely as long as they are utilizable for those of ordinary skill in the art. The sterilization method is not particularly limited, and, for example, radiation sterilization, ethylene oxide gas sterilization, autoclave sterilization, filter sterilization and the like can be mentioned.

In a preferable embodiment, the above-mentioned dispersion of nanofiber in a physiological aqueous solvent is mixed with a liquid medium to prepare the medium composition of the present invention. The dispersion may be sterilized (autoclave, gamma sterilization etc.). Alternatively, the dispersion and a liquid medium (aqueous solution as medium) prepared by dissolving the powder medium in water may be mixed, and used after sterilization. The dispersion and the liquid medium may be sterilized separately before mixing. Examples of the aqueous solvent include, but are not limited to, water, dimethyl sulfoxide (DMSO) and the like. As the aqueous solvent, water is preferable. The aqueous solvent may contain appropriate buffering agents and salts. The above-mentioned nanofiber dispersion is useful as a medium additive for preparing the medium composition of the present invention. The present invention also provides such medium additive.

As the mixing ratio, nanofiber dispersion:liquid medium (aqueous solution as medium) is generally 1:99-99:1, preferably 10:90-90:10, more preferably, 20:80-80:20.

When the nanofiber is constituted of a water-soluble polymer compound (e.g., water-soluble polysaccharides such as deacylated gellan gum and the like), the water-soluble polymer compound (e.g., water-soluble polysaccharides such as deacylated gellan gum and the like) and a medium may be mixed to form nanofibers in the medium, instead of mixing the nanofiber and a medium, whereby the medium composition of the present invention is produced. The shape of the polymer compound may be powder, tablet, pill, capsule, granule, or a liquid such as a solution obtained by dissolving in an appropriate solvent using a solubilizer or a suspension, or may be bonded to a substrate or a carrier. Examples of the additive used for formulating include preservatives such as p-oxybenzoic acid esters and the like; excipients such as lactose, glucose, sucrose, mannit and the like; lubricants such as magnesium stearate, talc and the like; binders such as poly(vinyl alcohol), hydroxypropylcellulose, gelatin and the like; surfactants such as fatty acid ester and the like; plasticizers such as glycerol and the like; and the like. These additives are not limited to those mentioned above, and can be selected freely as long as they are utilizable for those of ordinary skill in the art.

The above-mentioned polymer compound may be sterilized as necessary. The sterilization method is not particularly limited, and, for example, radiation sterilization, ethylene oxide gas sterilization, autoclave sterilization, filter sterilization and the like can be mentioned.

In a preferable embodiment, an aqueous solution of a water-soluble polymer compound (e.g., water-soluble polysaccharides such as deacylated gellan gum and the like) (used as medium additive 2) is used for the production method of the present invention. The aqueous solution can be obtained by dissolving a water-soluble polymer compound as a solid (e.g., powder) in a physiological aqueous solvent. Examples of the aqueous solvent include, but are not limited to, water, dimethyl sulfoxide (DMSO) and the like. As the aqueous solvent, water is preferable.

The aqueous solvent may contain an appropriate buffering agent or salt. While the aqueous solvent may or may not contain divalent metal cations, divalent metal cations are not contained in a preferable embodiment. When an aqueous solvent is free of divalent metal cations, a water-soluble polymer compound (e.g., water-soluble polysaccharides such as deacylated gellan gum and the like) does not easily form, in the aqueous solution, a nanofiber structure capable of culturing cells or tissues in a suspended state, and can be stably preserved in a dissolution state in water.

It is also possible to further add an additive to the above-mentioned medium additive to enhance the effect of nanofiber, or lower the concentration when in use, to the above-mentioned medium additive. As an example of such additive, one or more kinds of polysaccharides including guargum, tamarind gum, alginic acid propylene glycol ester, locust bean gum, gum arabic, tara gum, tamarind gum, methylcellulose and the like can be mixed.

Examples of the production method of the medium composition of the present invention are shown below, which are not to be construed as limitative. Nanofiber is added to ion exchange water or ultrapure water. The mixture is stirred until an entirely uniform dispersion is formed at room temperature, and sterilized (e.g., autoclave sterilization at 121° C. for 20 min). The nanofiber dispersion is added with stirring (e.g., homomixer etc.) to a given medium to be used for static culture to uniformly mix the solution with the medium. The mixing method of the aqueous solution and the medium is not particularly limited, and may be manual mixing such as pipetting etc., or mixing with an instrument such as magnetic stirrer, mechanical stirrer, homomixer and homogenizer.

For example, when a medium composition is prepared using a cellulose nanofiber, the cellulose nanofiber is added to ion exchange water or ultrapure water to 0.0001% to 5.0% (weight/volume), preferably 0.001% to 1.0% (weight/volume), more preferably 0.01% to 0.6% (weight/volume). The mixture is stirred until an entirely uniform state is formed at room temperature, and then sterilized (e.g., autoclave sterilization at 121° C. for 20 min). For example, the aqueous solution is added to a liquid medium such as DMEM medium with stirring by a homomixer and the like to a desired final concentration (e.g., when the final concentration is 0.003, the ratio of 0.6% aqueous solution:medium is 1:20), and the mixture is homogeneously mixed. Alternatively, a liquid medium such as DMEM medium and the like is added by pipette to the aqueous solution to a desired final concentration (e.g., when the final concentration is 0.03%, the ratio of 0.6% aqueous solution:medium is 1:20), and uniformly mixed by pipetting. The mixing method of the dispersion and the medium is not particularly limited, and may be manual mixing such as pipetting etc., or mixing with an instrument such as magnetic stirrer, mechanical stirrer, homomixer and homogenizer.

[Culture Method]

The present invention also provides a culture method for proliferating cells or tissues by using the above-mentioned medium composition of the present invention, a method of recovering the obtained cells or tissues by, for example, filtration, centrifugation or magnetic separation, and a production method of a sphere by using the medium composition of the present invention.

When cells and/or tissues are cultured in vitro, a nanofiber to be used in the present invention shows an effect of suspending (preferably effect of suspension standing) the cells and/or tissues in a liquid containing the nanofiber. By the suspending effect, a more increased amount of the cells and/or tissues per a given volume can be cultivated as compared to a single layer culture. When a conventional suspension culture method accompanies rotation or shaking operation, the proliferation rate and recovery rate of the cells and/or tissues may become low, or the function of the cell may be impaired since a shear force acts on the cells and/or tissues. Using the medium composition of the present invention, which contains a nanofiber, can uniformly disperse the cells and/or tissues without an operation such as shaking and the like, and can obtain the object cells and/or tissues easily in a large amount without loss of the cell function. In addition, when cells and/or tissues are suspension cultured in a conventional medium containing a gel substrate, observation and recovery of the cells and/or tissues are sometimes difficult, and the function thereof is sometimes impaired during recovery. However, using the medium composition containing the nanofiber of the present invention, the cells and/or tissues can be subjected to suspension culture, observed without impairment of the function thereof, and can be recovered. In addition, a conventional medium containing a gel substrate sometimes shows high viscosity that makes it difficult to exchange the medium. However, since the medium composition containing the nanofiber of the present invention has low viscosity, it can be exchanged easily with a pipette, pump and the like.

The human-derived cells and/or tissues cultured by the method of the present invention can be transplanted for a treatment object to patients having a disease or disorder. In this case, treatment target disease, the kind of disorder, a pre-treatment method and a cell transplantation method are appropriately selected by those of ordinary skill in the art. The engraftment of the transplanted cells in the recipient, recovery from the disease or disorder, the presence or absence of side effects associated with transplantation, and treatment effect are appropriately examined and judged by general methods for transplantation therapy.

Since cells and/or tissues are proliferated efficiently, moreover, a medium composition of the present invention can be used as a reagent for the study of cells. For example, when a factor controlling the differentiation and proliferation of cells and tissues is to be elucidated, cells and the object factor are cocultured, and the number and kind of the cell, and changes in the cell surface differentiation marker and expressed gene are analyzed. In this case, using the medium composition of the present invention, the number of the analysis target cells can be efficiently amplified, and efficiently recovered as well. When the object factor is elucidated, the culture conditions, culture apparatus, the kind of medium, the kind of the nanofiber of the present invention, the content of the nanofiber, the kind of the additive, the content of the additive, culture period, culture temperature and the like are appropriately selected by those of ordinary skill in the art from the range described in the present specification. The cell that was proliferated or emerged by culture can be observed using a standard microscope in the pertinent field. In this case, cultured cells may be stained with a specific antibody. The expressed gene that has changed due to the object factor can be found by extracting the RNA (ribonucleic acid) from the cultured cells and detecting by Northern Blotting, RT-PCR and the like. In addition, a cell surface differentiation marker is detected by ELISA and flow cytometry using a specific antibody, and the effect of the object factor on the differentiation and proliferation can be observed.

Since the cells and/or tissues are efficiently proliferated using the medium composition of the present invention, the culture method of the present invention is superior as a method of proliferating cells and/or tissues or proliferation-promoting method of cells and/or tissues. When cells and/or tissues are cultured using the medium composition of the present invention, the cells and/or tissues are dispersed while spreading three-dimensionally, without adhering to a culture container or without being locally present only on the bottom surface of the culture container, whereby the proliferation is promoted. Particularly, when chitin nanofiber is used as the nanofiber, the cells attach to the chitin nanofiber, and strongly proliferate therefrom as a scaffold.

As a result, the proliferated cells, cell aggregates (spheres etc.) and/or tissues are connected like cluster of grapes on the nanofiber. This proliferation-promoting effect only requires presence of nanofibers at a concentration sufficient for suspending cells and/or tissues (i.e., avoiding adhesion of cells and tissues to culture container) in the medium composition, and capability of suspension standing (i.e., cells and/or tissues being uniformly dispersed and in a suspended state in liquid medium composition, without the presence of pressure, trembling, shaking, rotating operation and the like from the outside) is not essential. For example, in the case of chitin nanofiber, a proliferation-promoting effect is provided as long as a concentration of not less than 0.0001% (weight/volume), which is sufficient for expression of a suspending action, is achieved, even when the concentration is below 0.03% (weight/volume) which enables stable suspension standing culture (e.g., not more than 0.025% (weight/volume), not more than 0.02% (weight/volume)). In the case of microcrystalline cellulose nanofiber, a proliferation-promoting effect is provided as long as it is not less than 0.01% (weight/volume), which is sufficient for expression of a suspending action, is achieved, even when the concentration is below 0.03% (weight/volume) which enables stable suspension standing culture (e.g., not more than 0.025% (weight/volume), not more than 0.02% (weight/volume)). In the case of deacylated gellan gum, a proliferation-promoting effect is provided as long as it is not less than 0.005% (weight/volume), which is sufficient for expression of a suspending action, is achieved, even when the concentration is below 0.01% (weight/volume) which enables stable suspension standing culture (e.g., not more than 0.009% (weight/volume), not more than 0.008% (weight/volume)).

Of nanofibers, chitin nanofiber is particularly superior in the cell proliferation-promoting effect.

In the culture method of the present invention, both non-adherent cells and adherent cells can be used. Adherent cells require scaffold for the growth and proliferation. Non-adherent cells do not require scaffold for the growth and proliferation. In the culture method of the present invention, adherent cells are preferably used. When adherent cells are used in the method of the present invention, the adherent cells are dispersed while spreading three-dimensionally, without adhering to the bottom surface of a culture container and without being locally present only on the bottom surface of the culture container, and proliferate in the state of being attached to the nanofiber, or in a sphere state. Particularly, when chitin nanofiber is used as the nanofiber, the cells attach to the chitin nanofiber, and strongly proliferate therefrom as a scaffold. As a result, the proliferated cells, cell aggregates (spheres etc.) and/or tissues are connected like cluster of grapes on the nanofiber. Therefore, suspension culture of adherent cells can be performed. In addition, proliferation of adherent cells can be promoted more than when cultured in the state of adhesion to the bottom surface of a culture container. Also, adherent cells can be cultured at higher density than when cultured in the state of adhesion to the bottom surface of a culture container.

In the culture method of the present invention, since suspension culture of adherent cells can be performed, adherent cells can be passaged by just adding, after suspension culture of the adherent cells by the culture method of the present invention, a fresh medium composition of the present invention to a culture after culture, or just adding a culture after culture entirely or partly to a fresh medium composition of the present invention, without a detaching operation of the cells from a culture container. The present invention also provides such passage culture method of adherent cells. Therefore, using the passage culture method of the present invention, adherent cells can be passaged without a detaching operation of the cells from a culture container. Using the passage culture method of the present invention, moreover, the culture scale of adherent cells can be expanded without a detaching operation of the cells from a culture container. As a detaching operation of the cells from a culture container, a treatment with a chelating agent (e.g., EDTA) and/or protease (e.g., trypsin, collagenase) can be mentioned. The passage culture method of the present invention is advantageous for passage culture of adherent cells highly sensitive to a detaching operation of the cells from a culture container (e.g., adherent cell with viability decreased by detaching operation, adherent cell with character susceptible to change by detaching operation). Examples of the adherent cells highly sensitive to a detaching operation of the cells from a culture container include, but are not limited to, human pluripotent stem cell; human progenitor cell; primary cells prepared from tissues such as hepatocyte, kidneycell, chondrocyte, blood vessel cell, adipocyte and the like; biological pharmaceutical products (protein for pharmaceutical products)-producing cells such as MDCK cell, HEK293 cell and CHO cell and the like, and the like.

Using the medium composition of the present invention, adherent cells can be cultured at high density, and cells and/or tissues can be proliferated efficiently. Therefore, the culture method of the present invention is useful for the production of useful substances by in vitro cell culture. The cells that produce useful substances are subjected to suspension culture in the medium composition of the present invention, and useful substances are isolated from the culture, whereby the useful substance(s) can be obtained. Examples of the useful substance include, but are not limited to, antibody, enzyme (urokinase etc.), hormone (insulin etc.), cytokine (interferon, interleukin, tumor necrosis factor, colony stimulating agent, growth factor etc.), vaccine antigen, and other physiologically active substances (protein, peptide etc.). The cells that produce useful substances includes untransformed cells such as skin cell, chondrocyte, hepatocyte, pancreatic cell, kidney cell and the like, and transformed cells into which a gene encoding a useful substance, or a gene involved in the biosynthesis of useful substances has been introduced. The cell that produces useful substances may be an adherent cell or a non-adherent cell, preferably an adherent cell. The cell that produces useful substances preferably secretes a useful substance extracellularly. Specific examples of the cell that produces useful substances include, but are not limited to, HEK293, CHO-K1, BHK-21, MDCK, Vero, HepG2, MCF-7 and the like into which a gene encoding a useful substance or a gene involved in the biosynthesis of a useful substance has been introduced. The cells used for the production of a useful substance such as recombinant protein and the like is well known to those of ordinary skill in the art, such cells can be used for the method of the present invention. The culture scale may be expanded by adding, after suspension culture of the adherent cells by the above-mentioned passage culture method of the present invention, a fresh medium composition of the present invention to a culture after culture, or adding a culture after culture entirely or partly to a fresh medium composition of the present invention, without a detaching operation of the cells from a culture container. To isolate a useful substance from a culture, cells need to be removed from the culture. Since the viscosity of the medium composition of the present invention is not substantially increased by the addition of nanofiber, and the cells are suspended in the medium composition, the cells can be removed by a convenient method such as centrifugation, filtration treatment and the like. In addition, nanofiber in the medium composition can also be removed by a convenient method such as centrifugation, filtration treatment and the like. A method for isolating a useful substance from a culture is well known to those of ordinary skill in the art and, for example, a biochemical separation and purification method of physiologically active substances such as chromatography (e.g., chromatographys such as ion exchange chromatography, hydrophobic chromatography, affinity chromatography, reversed-phase chromatography and the like) and the like can be applied.

When cells and/or tissues are cultivated by the culture method of the present invention, culture tools generally used for cell culture such as schale, flask, plastic bag, Teflon (registered trade mark) bag, dish, schale, dish for tissue culture, multidish, microplate, microwell plate, multiplate, multiwell plate, chamber slide, tube, tray, culture bag, roller bottle and the like can be used for cultivation. While the materials of these culture tools are not particularly limited, for example, plastic and the like such as glass, polyvinyl chloride, cellulose-based polymer, polystyrene, polymethylmethacrylate, polycarbonate, polysulfone, polyurethane, polyester, polyamide, polystyrene, polypropylene and the like can be mentioned. Moreover, these plastics may be applied with various surface treatments (e.g., plasma treatment, corona treatment etc.). Furthermore, these culture tools may be coated in advance with an extracellular matrix, a cell adhesion molecule and the like. Examples of the coating material include collagen I to XIX, fibronectin, vitronectin, laminin-1 to 12, nitogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin, hyaluronic acid, superfamily, Matrigel, poly-D-lysine, poly-L-lysine, chitin, chitosan, sepharose, alginic acid gel, hydrogel, cleavage fragments thereof and the like. These coating materials having an amino acid sequence artificially altered by gene recombination techniques can also be used. A coating material for inhibiting adhesion of the cells and/or tissues to culture tools can also be used. Examples of the coating material include, but are not limited to, silicon, poly(2-hydroxymethylmethacrylate), poly(2-methacryloyloxyethylphosphoryl choline) and the like.

The cells and/or tissues can also be cultured by automatically conducting cell seeding, medium exchange, cell image obtainment, and recovery of cultured cells, under a mechanical control and under a closed environment while controlling pH, temperature, oxygen concentration and the like and using a bioreactor and an automatic incubator capable of high density culture. As a method for supplying a new medium and feeding the required substances to the cells and/or tissues during the culture using such apparatuses, fed-batch culture, continuous culture and perfusion culture are available, and all these methods can be used for the culture method of the present invention.

Those of ordinary skill in the art can freely select the form and state of the cells and/or tissues to be cultured by the method of the present invention. Specific preferable examples thereof include, but are not particularly limited to, a state in which the cells and/or tissues are singly dispersed in the medium composition, a state in which the cells and/or tissues are attached to the surface of a carrier, a state in which the cells and/or tissues are embedded inside a carrier, a state in which plural cells assemble and form cell aggregations (spheres), or a state in which two or more kinds of cells assemble and form cell aggregations (spheres), and the like. More preferred are a state in which the cells and/or tissues are attached to the surface of a carrier, a state in which the cells and/or tissues are embedded inside a carrier, a state in which plural cells assemble and form cell aggregations (spheres), and a state in which two or more kinds of cells assemble and form cell aggregations (spheres). Further preferred are a state in which the cells and/or tissues are attached to the surface of a carrier, a state in which plural cells assemble and form cell aggregations (spheres), and a state in which two or more kinds of cells assemble and form cell aggregations (spheres). Among these states, the state with forming cell aggregations (spheres) can be mentioned as the most preferable state to be cultured by the culture method of the present invention, since cell-cell interactions and cell structures close to those in the in vivo environment are reconstructed, long-term culture can be performed while maintaining the cell function, and also cell recovery is relatively easy.

As a carrier to support the cells and/or tissues on the surface, microcarrier and glass bead composed of various polymers, ceramic bead and the like can be mentioned. As examples of the polymers, vinyl resin, urethane resin, epoxy resin, polystyrene, polymethylmethacrylate polyester, polyamide, polyimide, silicon resin, phenol resin, melamine resin, urea resin, aniline resin, ionomer resin, polycarbonate, collagen, dextran, gelatin, cellulose, alginates, mixtures thereof, and the like can be used. The carrier may be coated with a compound that enhances cell adhesion or release of substance from the cells. As examples of such coating materials, poly(monostearoylglyceride co-succinic acid), poly-D,L-lactid-co-glycolide, sodium hyaluronate, n-isopropylacrylamide, collagen I to XIX, fibronectin, vitronectin, laminin-1 to 12, nitogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, sepharose, alginic acid gel, various hydrogels, further, cleavage fragments thereof, and the like can be mentioned. Here, two or more kinds of the coating materials may be combined. Furthermore, one or more kinds of polysaccharides such as guargum, tamarind gum, locust bean gum, gum arabic, tara gum, tamarind gum, methylcellulose and the like can also be mixed with a medium to be used for culture of a carrier supporting the cells and/or tissues on the surface. The carrier may also contain a magnetic material, for example, ferrite. The diameter of the carrier is several tens of micrometers to several hundreds of micrometers, more preferably 100 μm to 200 μm, and its specific gravity is preferably close to 1, more preferably 0.9-1.2, particularly preferably about 1.0. Examples of the carrier include, but are not limited to, Cytodex 1 (registered trade mark), Cytodex 3 (registered trade mark), Cytoline 1 (registered trade mark), Cytoline 2 (registered trade mark), Cytopore 1 (registered trade mark), Cytopore 2 (registered trade mark), (above, GE Healthcare Life Sciences), Biosilon (registered trade mark) (NUNC), Cultispher-G (registered trade mark), Cultispher-S (registered trade mark) (above, Thermo SCIENTIFIC), HILLEXCT (registered trade mark), ProNectinF-COATED (registered trade mark), and HILLEXII (registered trade mark) (Solo Hill Engineering) and the like. The carrier may be sterilized as necessary. The sterilization method is not particularly limited and, for example, radiation sterilization, ethylene oxide gas sterilization, autoclave sterilization, dry heat sterilization, and the like can be mentioned. The method for culturing animal cells using the carrier is not particularly limited, and a culture method using a general flow layer-type culture vessel or filling layer-type culture vessel, and the like can be used. Here, a carrier supporting cells and/or tissues on the surface and using a medium composition comprising the nanofiber of the present invention allows for uniform dispersion even without an operation of shaking and the like. As a result, the object cells and/or tissues can be cultured without losing cell function. The cells and/or tissues cultured by this method can be collected by performing centrifugation and filtration treatment while the cells and/or tissues are supported by the carrier after the culture. In this case, centrifugation and filtration treatment may be performed after adding the liquid medium used. For example, unlimitatively, the gravitational acceleration (G) of centrifugation is 100G to 400G, and the size of the pore of the filter used for the filtration treatment is 10 μm to 100 μm. Furthermore, cultured carriers can be recovered with a magnetic force by encapsulating a material having magnetism, such as ferrite, in the carrier. The cells and/or tissues cultured by this method can be collected by releasing the carrier by using various chelating agents, a heat treatment, or an enzyme.

When cells and/or tissues are embedded inside a carrier, materials composed of various polymers can be selected as the carrier. As examples of such polymers, collagen, gelatin, alginates, chitosan, agarose, poly glycolic acid, polylactic acid, fibrin adhesive, polylactic acid-polyglycolic acid copolymer, proteoglycan, glycosaminoglycan, sponge such as polyurethane foam, DseA-3D (registered trade mark), poly N-substituted acrylamide derivative, poly N-substituted methacrylamide derivative, and copolymers thereof, polyvinyl methylether, polypropylene oxide, polyethylene oxide, temperature sensitive polymers such as partially acetified poly(vinyl alcohol), polyacrylamide, poly(vinyl alcohol), methylcellulose, nitrocellulose, cellulose butyrate, polyethylene oxide, and hydrogels such as poly(2-hydroxyethylmethacrylate)/polycaprolactone and the like can be mentioned. In addition, it is possible to prepare a carrier for embedding cells by using two or more kinds of these polymers. Furthermore, the carrier may have a physiologically active substance besides these polymers. As examples of the physiologically active substance, cell growth factors, differentiation inducing factors, cell adhesion factors, antibodies, enzymes, cytokines, hormones, lectins, extracellular matrices and the like can be mentioned, and a plurality of these can also be contained. Furthermore, one or more kinds of thickeners such as guargum, tamarind gum, alginic acid propylene glycol ester, locust bean gum, gum arabic, tara gum, methylcellulose and the like can also be mixed with a medium used for culture of a carrier embedding cells and/or tissues.

The method for embedding the cells and/or tissues in these carriers is not particularly limited and, for example, a method including aspirating a mixture of the cells and the aforementioned polymers with a syringe and dropwise adding them to a medium from around 25G-19G injection needle, or dropwise adding to a medium using a micropipette, and the like can be used. The size of the bead-like carrier formed here is determined by the shape of the tip of a tool used for the dropwise addition of a mixture of the cell and the aforementioned polymers, which is preferably several tens of micrometers to several thousands of micrometers, more preferably 100 μm to 2000 μm. The number of cells that can be cultured on a bead-like carrier is not particularly limited, and can be freely selected according to the bead size. For example, 5 million cells can be embedded in a bead-like carrier with a diameter of about 2000 μm. Within the carrier, the cells may be singly dispersed or plural cells may assemble to form a cell aggregate. Here, using a medium composition comprising the nanofiber of the present invention allows a carrier having the cells and/or tissues embedded therein to uniformly disperse even without an operation of stirring and the like. As a result, the object cells and/or tissues can be cultured without losing cell function. The cells and/or tissues cultured by this method can be collected by performing centrifugation and filtration treatment while the cells and/or tissues are embedded in the carrier after the culture. In this case, centrifugation and filtration treatment may be performed after adding the liquid medium used. For example, unlimitatively, the gravitational acceleration (G) of centrifugation is 100G to 400G, and the size of the pore of the filter used for the filtration treatment is 10 μm to 100 μm. The cells and/or tissues cultured by this method can be collected by dispersing them by decomposing the carrier by a treatment using various chelating agents, heat, an enzyme and the like.

A method for forming a cell aggregate (sphere) is not particularly limited, and can be appropriately selected by those of ordinary skill in the art. Examples thereof include a method using a container having a cell non-adhesive surface, hanging drop method, gyratory culture method, three-dimensional scaffold method, centrifugation method, a method using coagulation by an electric field or magnetic field and the like. For example, using a method using a container having a cell non-adhesive surface, the object cells are cultured in a culture container applied with a surface treatment to inhibit cell adhesion, whereby a sphere can be formed. When such cell non-adhesive culture container is used, the object cells are first collected, a cell suspension thereof is prepared and plated in the culture container to perform culture. When culture is continued for about 1 week, the cells spontaneously form a sphere. As a cell non-adhesive surface used here, a surface of a culture container generally used such as schale and the like, which is coated with a substance inhibiting cell adhesion and the like can be used. Examples of such substance include agarose, agar, copolymer of poly-HEMA(poly-(2-hydroxlethylmethacrylate)2-methacryloyloxyethylphosphoryl choline and other monomer (e.g., butylmethacrylate etc.) and the like. When cytotoxicity is absent, the substance is not limited thereto.

As a method for forming a cell aggregate (sphere), the methods described in NATURE BIOTECHNOLOGY, VOL. 28, NO. 4, APRIL 2010, 361-366, NATURE PROTOCOLS, VOL. 6, NO. 5, 2011, 689-700, NATURE PROTOCOLS, VOL. 6, NO. 5, 2011, 572-579, Stem Cell Research, 7, 2011, 97-111, Stem Cell Rev and Rep, 6, 2010, 248-259 and the like can also be used.

In addition, a medium used for culture forming a sphere can also contain a component that promotes formation of a sphere or promotes maintenance thereof. Examples of the component having such effect include ROCK inhibitors such as dimethyl sulfoxide, superoxide dismutase, caeruloplasmin, catalase, peroxidase, L-ascorbic acid, L-ascorbic acid phosphate ester, tocopherol, flavonoid, uric acid, bilirubin, selenium-containing compound, transferrin, unsaturated fatty acid, albumin, theophylline, forskolin, glucagon, dibutyryl cAMP, Y27632, Fasudil (HA1077), H-1152, Wf-536 and the like, and the like. As the selenium-containing compound, sodium selenite, sodium selenate, dimethyl selenide, hydrogen selenide, Selenomethionine, Se-Methylselenocysteine, Selenocystathionine, Selenocysteine, Selenohomocysteine, adenosine-5′-triphosphoric acid, Se-Adenosylselenomethionine can be mentioned. To obtain the object cell aggregate having a uniform size, plural concaves having the same diameter as the object cell aggregate can also be introduced onto a cell non-adhesive culture container to be used. When these concaves are in contact with each other or within the range of the diameter of the object cell aggregate, and cells are plated, the plated cells do not form a cell aggregate between concaves but certainly form a cell aggregate with a size corresponding to the volume thereof in the concave, thus affording a cell aggregate population having a uniform size. As the shape of the concave in this case is preferably a hemisphere or cone.

Alternatively, a sphere can also be formed based on a support showing cell adhesiveness. Examples of such support include collagen, polyrotaxane, polylactic acid (PLA), polylactic acid glycolic acid (PLGA) copolymer, hydrogel and the like.

In addition, a sphere can also be formed by co-cultivating with a feeder cell. As a feeder cell to promote sphere formation, any adhesive cell can be used. Preferably, a feeder cell for each kind of cell is desirable. Although not limited, for example, when a sphere of cells derived from the liver or cartilage is formed, examples of the feeder cell include COS-1 cell and vascular endothelial cell as preferable cell types.

Furthermore, a sphere can also be formed using the culture composition containing the nanofiber of the present invention. In this case, the nanofiber only needs to be added to the medium used for formation of sphere such that the concentration of the nanofiber enables suspension culture (preferably suspension stand culture) of cells. For example, the nanofiber only needs to be added to the medium used for formation of sphere such that the concentration of the nanofiber is generally 0.0001% to 1.0% (weight/volume), for example, 0.0005% to 1.0% (weight/volume), preferably 0.001% to 0.3% (weight/volume), more preferably 0.005% to 0.1% (weight/volume), further preferably 0.01% to 0.05% (weight/volume). The sphere is prepared by uniformly dispersing the object cells in a medium containing the nanofiber, and allowing them to culture by standing them still for 3 days to 10 days. The prepared sphere can be recovered by centrifugation and filtration treatment. For example, unlimitatively, the gravitational acceleration (G) of centrifugation is 100G to 400G, and the size of the pore of the filter used for the filtration treatment is 10 μm to 100 μm. In addition, using magnetic fine particles coated, on the surface, with an antibody that specifically binds to the object cell, cultured sphere can be recovered by magnetic force. Examples of such magnetic fine particles include Dynabeads (manufactured by Veritas Ltd.), MACS microbead (manufactured by Miltenyi Biotec), BioMag (manufactured by Techno Chemicals Corporation) and the like.

The size of the sphere varies depending on the cell type and culture period and is not particularly limited. When it has a spherical shape or ellipse spherical shape, the diameter thereof is 20 μm to 1000 μm, preferably 40 μm to 500 μm, more preferably 50 μm to 300 μm.

Such sphere can maintain proliferative capacity for not less than 10 days, preferably not less than 13 days, more preferably not less than 30 days, by continuing the standing culture. By regularly further performing, during the standing culture, mechanical division, or a single cell-forming treatment and coagulation, the proliferative capacity can be maintained substantially infinitely.

The culture container to be used for culturing sphere is not particularly limited as long as it generally permits animal cell culture. For example, flask, dish, schale, tissue culture dish, multidish, microplate, microwell plate, multiplate, multiwell plate, chamber slide, schale, tube, tray, culture bag, roller bottle and the like can be mentioned.

The medium to be used for standing culture of sphere can contain a cell adhesion factor, examples thereof include Matrigel, collagen gel, gelatin, poly-L-lysine, poly-D-lysine, laminin and fibronectin. Two or more kinds of these cell adhesion factors can also be added in combination. Furthermore, the medium to be used for culturing sphere can be mixed with a thickener such as guargum, tamarind gum, alginic acid propylene glycol ester, locust bean gum, gum arabic, tara gum, methylcellulose and the like.

Using a medium composition comprising the nanofiber of the present invention, uniform dispersion in a medium can be afforded even without an operation of shaking and the like. As a result, the object cells and/or tissues can be cultured as a sphere without losing cell function. The sphere standing cultured by this method can be collected by performing centrifugation or filtration treatment after the culture. In this case, centrifugation or filtration treatment may be performed after adding the liquid medium used. For example, unlimitatively, the gravitational acceleration (G) of centrifugation is 100G to 400G, and the size of the pore of the filter used for the filtration treatment is 10 μm to 100 μm. In addition, using magnetic fine particles coated, on the surface, with an antibody that specifically binds to the object cell, cultured sphere can be recovered by magnetic force. Examples of such magnetic fine particles include Dynabeads (manufactured by Veritas Ltd.), MACS microbead (manufactured by Miltenyi Biotec), BioMag (manufactured by Techno Chemicals Corporation) and the like. The recovered sphere can be dispersed as a single cell by further decomposing by a treatment with various chelating agents, heat, filter, enzyme and the like.

As a method for standing culture of plant-derived cells and/or tissues, callus, which is an undifferentiated plant cell aggregate, can be cultivated. Callus can be induced by a method known for each plant species to be used. For example, a surface of a part of a tissue of a differentiated plant body (e.g., root, stalk, leaf section, seed, growing point, embryo, pollen etc.) is sterilized, where necessary, with 70% alcohol, 1% sodium hypochlorite solution and the like, a tissue section with a suitable size (e.g., about 1-about 5 mm square root section) is cut out with a knife and the like, the tissue section is plated on a callus induction medium sterilized in advance by an aseptic operation using a clean bench and the like, and aseptically cultivated under suitable conditions. The callus induced here may be subjected to liquid culture for mass proliferation, or may also be maintained as a seed strain by passaging in a passage medium. The passage culture may be performed using any of liquid medium and solid medium.

The amount of the plant cell aggregate inoculated when starting the standing culture using the medium composition of the present invention varies depending on the proliferation rate of the object cell, culture manner (batch culture, fed-batch culture, continuous culture etc.), culture period and the like. For example, when a plant cell aggregate such as callus and the like is to be cultivated, it is inoculated to the medium composition of the present invention such that the wet weight of the cell aggregate relative to the medium composition of the present invention is 4-8 (weight/volume (w/v))%, preferably 5-7 (w/v) %. The particle size of the plant cell aggregate during culture is 3 mm to 40 mm, preferably 3 mm to 20 mm, more preferably 5 mm to 15 mm. As used herein, the "particle size" means a diameter when, for example, the plant cell aggregate has a spherical shape, a major axis when it has an ellipse spherical shape, and the maximum length possible when it has other shape.

The temperature when cells and/or tissues are cultivated is generally 25 to 39° C., preferably 33 to 39° C., for animal cells. The $CO_2$ concentration is generally 4 to 10% by volume in the culture atmosphere, and 4 to 6% volume is preferable. The culture period is generally 3 to 35 days, which may be freely set according to the object of the culture. The culture temperature for plant cells is generally 20 to 30° C. and, when light is necessary, they can be cultured under illuminance conditions of illuminance 2000-8000 lux. While the culture period is generally 3 to 70 days, which may be freely set according to the object of the culture.

When cells and/or tissues are cultivated by the method of the present invention, cells and/or tissues prepared separately are added to the culture composition of the present invention and mixed to give a uniform dispersion. In this case, the mixing method is not particularly limited and, for example, manual mixing using pipetting and the like, mixing using instrument such as stirrer, vortex mixer, microplate mixer, shaking machine and the like can be mentioned. After mixing, the culture medium may be stood still, or the culture medium may be rotated, shaken or stirred as necessary. The rotation number and frequency can be appropriately set according to the object of those of ordinary skill in the art. When the medium composition needs to be exchanged during the standing culture period, the cells and/or tissues and the medium composition are separated by centrifugation or filtration treatment, and a new medium composition can be added of the cells and/or tissues. Alternatively, the cells and/or tissues are appropriately concentrated by centrifugation or filtration treatment, and a new medium composition can be added to the concentrated liquid. For example, unlimitatively, the gravitational acceleration (G) of centrifugation is 100G to 400G, and the size of the pore of the filter used for the filtration treatment is 10 μm to 100 μm. In addition, using magnetic fine particles coated, on the surface, with an antibody that specifically binds to the object cell, the cultured cells and/or tissues can be separated by magnetic force. Examples of such magnetic fine particles include Dynabeads (manufactured by Veritas Ltd.), MACS microbead (manufactured by Miltenyi Biotec), BioMag (manufactured by Techno Chemicals Corporation) and the like. Exchange of the medium composition can also be performed by using a bioreactor and an automatic incubator capable of conducting under a mechanical control and under a closed environment.

[Preservation or Transportation Method of Cell or Tissue]

In addition, the present invention provides a preservation method for preserving cell or tissue and a transport method, which uses the above-mentioned medium composition of the present invention. In the preservation or transport method of the present invention, the cells and tissues can be preserved or transported in a suspended state (preferably, suspension stand state) by using the medium composition of the present invention.

The cells and tissues to be the target of preservation or transport may be those mentioned above as the cells and tissues that can be used for culture using the medium composition of the present invention.

The medium composition of the present invention to be used for preservation or transport may contain, in addition to the aforementioned composition, various components having a cell life-prolonging effect, during preservation of cells and tissues in a non-frozen state. Examples of the component include saccharides (excluding polysaccharides) (e.g., monosaccharides, disaccharides), antioxidants (e.g., SOD, vitamin E or glutathione), hydrophilic polymers (e.g., polyvinylpyrrolidone), chelating agents (e.g., EDTA), sugar alcohols (e.g., mannitol, sorbitol), glycerol and the like.

In the preservation or transport method of the present invention, a desired cell or tissue is dispersed in the medium composition of the present invention, and placed in a tightly-sealed container. Examples of the container include, but are not limited to, flask, plastic bag, Teflon (registered trade mark) bag, tube, culture bag and the like. To avoid leakage of the contents and contamination with bacterium and the like from the outside world during preservation or transport, a container containing the dispersed materials of cells and tissues in the medium composition of the present invention is preferably tightly sealed.

While the temperature during preservation or transport is not particularly limited as long as the survival of the cell or tissue is maintained, it is generally not more than 37° C. A decrease in the viability of cell or tissue during preservation or transport can be avoided when the temperature is low. However, to prevent freezing of cells or tissues, they are generally preserved or transported at a temperature exceeding the melting point of the medium composition of the present invention. Therefore, the temperature during preservation or transport is generally maintained at −5-42° C., preferably 1-37° C., more preferably 4-32° C., further preferably 18-30° C.

To enable preservation or transport of cell or tissue in a suspension standing state, the temperature during preservation or transport is preferably a temperature permitting suspension stand of cell or tissue in the medium composition of the present invention. A temperature permitting suspension stand of cell or tissue can be appropriately determined according to the kind of a starting material constituting the nanofiber.

In one embodiment, carageenan (preferably, κ-carageenan) is used as a starting material constituting the nanofiber contained in the medium composition of the present invention to be used in the preservation or transportation method of the present invention. The medium composition of the present invention containing a nanofiber composed of carageenan has a suspending action at 25° C. or below, and loses the suspending action at 37° C. Therefore, desired cells or tissues are preserved or transported in a suspension stand at 25° C. or below (preferably 0-25° C.) and, after completion of the preservation or transport, the temperature is set to not less than 37° C. (e.g., 37-40° C., preferably 37° C.) to cause sedimentation of the suspended cells or tissues, whereby cells or tissues can be recovered with ease.

The period of preservation or transport is not particularly limited as long as the cells or tissues can be maintained in a viable state in the medium composition of the present invention. It is generally not less than 1 hr, within 10 days, preferably 1-8 days, more preferably 1-3 days. During the preservation or transport period, the cells or tissues are preferably maintained in a suspension stand state in the medium composition of the present invention.

Using the preservation or transportation method of the present invention, cells and tissues can be maintained in a suspended state. Accordingly, damage on the cells and tissues resulting from trembling during transport that detaches them from the plate, or aggregation of cells and tissues that came in contact with each other due to sedimentation can be avoided, and the cells and tissues can be preserved and transported while maintaining the inherent functions thereof.

EXAMPLES

The present invention is explained in more detail in the following by specifically describing an Example of the medium composition of the present invention. The materials, amount of use, ratio, contents of treatment and treatment procedures shown in the following Examples can be appropriately changed without departing from the gist of the present invention. Therefore, the scope of the present invention should not be interpreted to be the specific examples shown below.

Reference Example 1 Viscosity Measurement of Medium Containing Deacylated Gellan Gum Heat-Treated at High Temperature and Cell Suspension Test Preparation and Viscosity Measurement of Deacylated Gellan Gum-Containing Medium Deacylated gellan gum (KELCOGEL CG-LA, manufactured by SANSHO Co., Ltd.) was suspended in pure water to 0.4% (w/v), and dissolved by stirring with heating at 90° C. This aqueous solution was allowed to cool to room temperature with stirring, and sterilized at 121° C. for 20 min in an autoclave. A 2-fold concentration of DMEM/F-12 medium (manufactured by Aldrich, 50 mL) and sterilization water (47.5 mL) were placed in a 300 mL tall beaker with stirring by a homomixer (3000 rpm) at room temperature, aqueous deacylated gellan gum solution (2.5 mL) was added, and the mixture was continuously stirred for 1 min to prepare a deacylated gellan gum medium composition with a final concentration of 0.01%. Medium compositions added with aqueous deacylated gellan gum solution with final concentrations of 0.02, 0.03 and 0.05% (w/v) were similarly prepared. The viscosity of the medium compositions was measured using an E type viscometer (manufactured by Toki Sangyo Co., Ltd., Viscometer TVE-22 L, standard roter 1° 34'×R24) under 37° C. condition at 100 rpm for 5 min.

Cell Suspension Test of Deacylated Gellan Gum-Containing Medium

Human cervical cancer, cell line HeLa (manufactured by DS PHARMA BIOMEDICAL CO., LTD.) was suspended in EMEM medium containing 10% (v/v) fetal bovine serum (manufactured by WAKO) at 250000 cells/mL, the suspension (10 mL) was plated on EZ SPHERE (manufactured by ASAHI GLASS CO., LTD.), and cultured in a $CO_2$ incubator (5% $CO_2$) for 3 days. The obtained suspension (10 mL) of spheres (diameter 100-200 μm) was centrifuged (200G, for 5 min) to allow for sphere sedimentation, and the supernatant was removed to give a sphere suspension (1.0 mL). Successively, the deacylated gellan gum-containing medium prepared above was placed in a 1.5 mL Eppendorf tube by 1.0 mL, and a HeLa cell sphere suspension (10 μL) was further added. The cell aggregate was dispersed by tapping, incubated at 37° C., and the dispersion state of the cells for 1 hr later was visually observed.

TABLE 1

| deacylated gellan gum concentration % (w/v) | state | viscosity (mPa · s) | HeLa cell suspension/ sedimentation |
|---|---|---|---|
| 0.01 | liquid | 1.31 | suspension |
| 0.02 | liquid | 1.92 | suspension |
| 0.03 | liquid | 2.38 | suspension |
| 0.05 | liquid | 3.34 | suspension |

Reference Comparative Example Preparation of Methylcellulose and Collagen-Containing Medium Preparation of Methylcellulose-Containing Medium DMEM/F-12 medium (manufactured by Aldrich, 100 mL) was placed in a 200 mL recovery flask, and methylcellulose (M0387, manufactured by Aldrich, 0.1 g) was added. The mixture was stirred while cooling in an ice bath to dissolve methylcellulose. Using this solution, medium compositions added with the aqueous methylcellulose solution at a final concentration of 0.1, 0.3, 0.6 or 1.0% (w/v) were prepared.

Preparation of Collagen-Containing Medium

A 10-fold concentration of DMEM/F-12 medium (manufactured by Aldrich, 1 mL), a buffer for reconstitution (manufactured by Nitta Gelatin Inc., 1 mL) and pure water (1.5 mL) were added to 0.3% cell matrix type I-A (manufactured by Nitta Gelatin Inc., 6.5 mL), and the mixture was stirred in an ice to give a 0.2% collagen-containing medium. Similarly, medium compositions added with collagen at a final concentration of 0.01, 0.05, 0.1 or 0.2% (w/v) were prepared.

The medium compositions prepared above were subjected to a suspension test of HeLa cell spheres and a viscosity measurement, in the same manner as with the deacylated gellan gum-containing medium. The viscosity of 1.0% (w/v) methylcellulose was measured at 50 rpm due to the measurement range of the apparatus.

TABLE 2

| methylcellulose concentration % (w/v) | state | viscosity (mPa · s) | HeLa cell suspension/ sedimentation |
|---|---|---|---|
| 0.1 | liquid | 2.31 | sedimentation |
| 0.3 | liquid | 8.15 | sedimentation |
| 0.6 | liquid | 13.0 | sedimentation |
| 1.0 | liquid | 48.2 | sedimentation |

TABLE 3

| collagen concentration % (w/v) | state | viscosity (mPa · s) | HeLa cell suspension/ sedimentation |
|---|---|---|---|
| 0.01 | liquid | 1.18 | sedimentation |
| 0.05 | liquid/solid (gel) | unmeasurable | suspension |
| 0.1 | solid (gel) | unmeasurable | suspension |
| 0.2 | solid (gel) | unmeasurable | suspension |

Reference Experimental Example

In the following Reference Experimental Examples, the $CO_2$ concentration (%) in a $CO_2$ incubator was shown by % volume of $CO_2$ in the atmosphere. PBS means phosphate buffered saline (manufactured by Sigma Aldrich Japan), and FBS means fetal bovine serum (manufactured by Biological Industries). In addition, (w/v) shows weight per volume.

Reference Experimental Example 1: Cell Proliferation Test by Dispersing Single Cell Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to IMDM medium (manufactured by Gibco) containing 10% (v/v) fetal bovine serum and 10 ng/mL thrombopoietin (manufactured by WAKO). Successively, human leukemia cell line UT7/TPO was plated on a medium composition added with the above-mentioned deacylated gellan gum to 20000 cells/mL, and dispensed to a 6-well flat bottom microplate (manufactured by Corning Incorporated) at 5 mL/well. Similarly, human cervical cancer, cell line HeLa (manufactured by DS PHARMA BIOMEDICAL CO., LTD.) was plated at 20000 cell/mL on a medium composition obtained by adding 0.015% (w/v) deacylated gellan gum (KELCOGEL CG-LA, manufactured by SANSHO Co., Ltd.) to EMEM medium containing 10% (v/v) fetal bovine serum (manufactured by WAKO), and the composition was dispensed to a 6-well flat bottom microplate (manufactured by Corning Incorporated) at 5 mL/well. The cell suspensions were cultured while being stood still in a $CO_2$ incubator (5% $CO_2$) for 3 days. Thereafter, a part of the culture medium was recovered, the same amount of Trypan Blue staining solution (manufactured by Invitrogen Corporation) was added, and the number of viable cells was measured by blood cell meter (manufactured by ERMA INC.)

As a result, it was confirmed that, using the above-mentioned medium composition, UT7/TPO cells and HeLa cells can be uniformly cultivated in a suspended state, and efficiently proliferate in the medium composition. The cell numbers of UT7/TPO cells and HeLa cells after static suspension culture for 3 days are shown in Table 4.

TABLE 4

|  | UT7/TPO cells | HeLa cells |
| --- | --- | --- |
| cell number (×10000/mL) | 38 | 40 |

Reference Experimental Example 2: Cell Proliferation Test by Culturing Cell Line-Derived Sphere Human liver cancer cell line HepG2 (manufactured by DS PHARMA BIOMEDICAL CO., LTD.) was suspended in DMEM medium containing 10% (v/v) fetal bovine serum (manufactured by WAKO) at 250000 cells/mL, and this suspension (10 mL) was plated on EZ SPHERE (manufactured by ASAHI GLASS CO., LTD.) and cultured for 7 days in a $CO_2$ incubator (5% $CO_2$). Similarly, human cervical cancer, cell line HeLa (manufactured by DS PHARMA BIOMEDICAL CO., LTD.) was suspended in EMEM medium containing 10% (v/v) fetal bovine serum (manufactured by WAKO) at 250000 cells/mL, and this suspension (10 mL) was plated on EZ SPHERE (manufactured by ASAHI GLASS CO., LTD.) and cultured for 7 days in a $CO_2$ incubator (5% $CO_2$). The suspension (2.5 mL) of the sphere (diameter 100-200 μm) of each cell line obtained here was centrifuged (200G, for 5 min) to allow for sphere sedimentation, and the supernatant was removed. Successively, the above-mentioned medium (10 ml) was added to the spheres (about 800 spheres) to suspend them and the suspension was transferred to a flat bottom tube (manufactured by BM Equipment Co., Ltd.). Similarly, using a medium composition obtained by adding 0.015% (w/v) deacylated gellan gum (KELCOGEL CG-LA, manufactured by SANSHO Co., Ltd.) to the above-mentioned medium, a sphere suspension was produced and transferred to a flat bottom tube (manufactured by BM Equipment Co., Ltd.). The medium composition added with 0.015% (w/v) deacylated gellan gum was prepared by first suspending deacylated gellan gum (KELCOGEL CG-LA, manufactured by SANSHO Co., Ltd.) in ultrapure water (Milli-Q water) to 0.3% (w/v), dissolving same by stirring with heating at 90° C., sterilizing this aqueous solution at 121° C. for 20 min in an autoclave, and adding the solution at 1/20 dilution to DMEM medium containing 10% (v/v) fetal bovine serum.

After static culture of the above-mentioned sphere suspension in a $CO_2$ incubator (5% $CO_2$) at 37° C. for 3 days, a two-fold volume of the medium was added. The mixture was centrifuged (200G, for 5 min) to allow for sphere sedimentation, and the supernatant was removed. At this point, a part of the sphere was taken, and the shape thereof was observed with an optical microscope (manufactured by OLYMPUS, CK30-F100). Successively, the recovered sphere was washed once with PBS (10 mL), 1 mL of trypsin-EDTA (ethylenediaminetetraacetic acid) solution (manufactured by WAKO) was added, and the mixture was incubated at 37° C. for 5 min. The above-mentioned medium (9 mL) was added, and the cells were collected by centrifugation (200G, for 5 min). To a part of the obtained cell suspension (2 mL) was added the same amount of a Trypan Blue staining solution (manufactured by Invitrogen Corporation), and the numbers of the viable cells and dead cells were measured by a hemocytometer (manufactured by ERMA INC.).

As a result, it was confirmed that, using the above-mentioned medium composition, the spheres of HepG2 cells and HeLa cells could be cultivated in a suspended state, and the cells efficiently proliferate in the medium composition. Furthermore, the medium composition was confirmed to show a small rate of the dead cells as compared to the existing media when the cells were proliferated, and have a superior cell proliferation promoting effect. The sphere cultured in an existing medium sedimented on the bottom of the culture container. Furthermore, the shape of the cultured sphere was observed by an optical microscope. As a result, the medium composition did not show association of the spheres, whereas association of the spheres was observed in the existing media.

Figure 1:
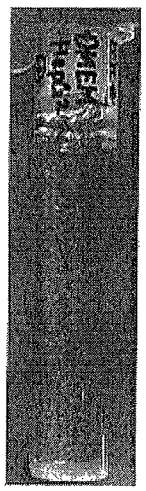
FIG. 1 is a Figure showing that, when spheres of HepG2 cells were cultured in the medium composition, the spheres were uniformly dispersed and could be cultured in a suspended state.
Figure 2:
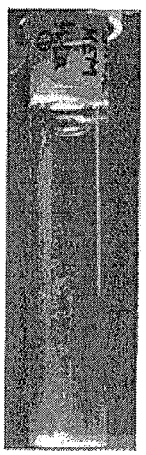
FIG. 2 is a Figure showing that, when spheres of HeLa cells were cultured in the medium composition, the spheres were uniformly dispersed and could be cultured in a suspended state.
Figure 3:
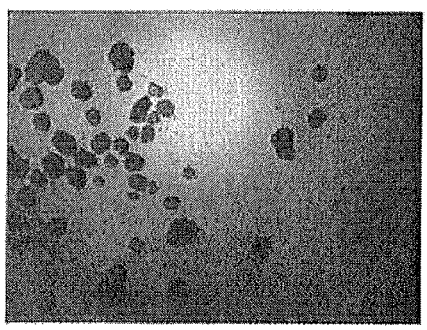
FIG. 3 is a Figure showing that, when spheres of HeLa cells were cultured in the medium composition and observed with a microscope, association of the spheres could be suppressed compared to existing media.
Figure 3:

The relative number of the HepG2 cells and HeLa cells is shown in Table 5, wherein the number of the cells cultured in a medium free of deacylated gellan gum is 1. In addition, the relative rate of the dead cells is shown in Table 6, wherein the rate of the dead cells cultured in a medium free of deacylated gellan gum (dead cell number/viable cell number) is 1. The suspended state of the spheres of HepG2 cells and HeLa cells cultured in the medium composition is shown in FIG. 1 and FIG. 2, respectively. Furthermore, the shape of the sphere of the cultured HeLa cells is shown in FIG. 3.

TABLE 5

| deacylated gellan gum | | HepG2 cells | HeLa cells |
| --- | --- | --- | --- |
| absent | relative cell number | 1.0 | 1.0 |
| present | relative cell number | 1.7 | 1.5 |

TABLE 6

| deacylated gellan gum | | HepG2 cells | HeLa cells |
|---|---|---|---|
| absent | relative mortality rate | 1.0 | 1.0 |
| present | relative mortality rate | 0.5 | 0.5 |

Reference Experimental Example 3: Cell Proliferation Test by Culturing Cell Line Attached onto Microcarrier Microcarrier Cytodex (registered trade mark) 1 (manufactured by GE Healthcare Life Sciences) was suspended in PBS at 0.02 g/mL, and the suspension was stood overnight. The supernatant was discarded, and the microcarrier was washed twice with fresh PBS. Thereafter, it was suspended again in PBS at 0.02 g/mL, and sterilized at 121° C. for 20 min in an autoclave. Successively, this microcarrier was washed twice with 70% ethanol and three times with PBS, and suspended in DMEM medium containing 10% (v/v) fetal bovine serum (manufactured by WAKO) at 0.02 g/mL. Using this microcarrier suspension, DMEM medium (containing 10% (v/v) fetal bovine serum, 20 mL) containing 120 mg of Cytodex (registered trade mark) 1 and 4000000 HepG2 cells was prepared, and the cell suspension was cultured in a beaker treated in advance with a silicon coating agent (manufactured by AGC TECHNO GLASS Co., Ltd.), with stirring (100 rpm) with a stirrer at 37° C. for 6 hr. At this point, adhesion of HepG2 cells to the microcarrier was confirmed with a microscope. Successively, the microcarrier with the cells adhered thereto was washed twice with DMEM medium containing 10% (v/v) fetal bovine serum, and suspended in the same medium (3 mL).

Figure 4:
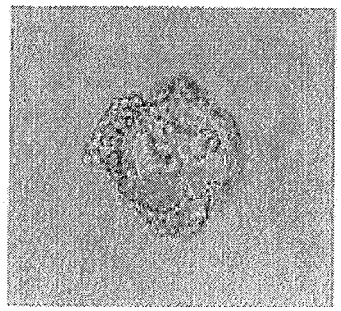
FIG. 4 is a Figure showing that, when microcarriers attached with HepG2 cells was cultured in the medium composition, the HepG2 cells could be proliferated on the microcarrier.

The above-mentioned microcarrier suspension (300 µL) was added to each of DMEM medium (20 mL) containing 10% (v/v) fetal bovine serum and a medium composition obtained by adding, to this medium, 0.015% (w/v) deacylated gellan gum (KELCOGEL CG-LA, manufactured by SANSHO Co., Ltd.), and the mixtures were cultured at 37° C. for 3 days. In the case of the culture medium free of deacylated gellan gum, the mixtures were cultured while stirring (100 rpm) with a stirrer. After culture, the attachment state of the cells on the microcarrier was confirmed with a microscope, and the microcarrier was sedimented by centrifugation (200G, for 5 min). This microcarrier was washed with PBS (10 mL), 1 mL trypsin-EDTA (ethylenediaminetetraacetic acid) solution (manufactured by WAKO) was added, and the mixture was incubated at 37° C. for 5 min. Furthermore, DMEM medium (9 mL) containing 10% (v/v) fetal bovine serum was added, and the microcarrier was removed by Cell Strainer (manufactured by BD Falcon, mesh size 70 µm). The cells were recovered from the obtained filtrate by centrifugation (200G, for 5 min). The cells were suspended in a medium (500 µL), to a part thereof was added the same amount of Trypan Blue staining solution (manufactured by Invitrogen Corporation), and the number of viable cells was measured by a hemocytometer (manufactured by ERMA INC.). As a result, the culture medium free of deacylated gellan gum contained 123,000 cells, but the culture medium containing deacylated gellan gum contained 1,320,000 cells. As mentioned above, it was confirmed that the medium composition containing the structure of the particular compound is superior in the cell proliferation promoting effect as compared to the existing media, even when the cells were cultured using a microcarrier. The attachment state of HepG2 cells after 3 days of microcarrier culture using the medium composition containing the structure of the particular compound is shown in FIG. 4.

Reference Experimental Example 4: Cell Suspension Test Using Cell Line-Derived Sphere Xanthan gum (KELTROL CG, manufactured by SANSHO Co., Ltd.) was suspended in ultrapure water (Milli-Q water) to a concentration of 1% (w/v), and dissolved by stirring with heating at 90° C. Using this aqueous solution, DMEM/F-12 medium compositions having a final xanthan gum concentration of 0.1, 0.15 or 0.2% (w/v) were prepared. In addition, an aqueous solution containing 0.2% (w/v) K-carageenan (GENUGEL WR-80-J, manufactured by SANSHO Co., Ltd.) and 0.2% (w/v) locust bean gum (GENUGUM RL-200-J, manufactured by SANSHO Co., Ltd.) was prepared by heating at 90° C. Using the aqueous solution, DMEM/F-12 medium (manufactured by Sigma Ltd.) compositions containing 0.03, 0.04 or 0.05% (w/v) K-carageenan and locust bean gum were prepared.

Figure 5:
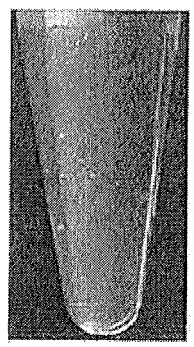
FIG. 5 is a Figure showing that, when spheres of HeLa cells were added to the medium composition, the spheres were uniformly dispersed and were in a suspended state.
Figure 5:

In the same manner as in Reference Experimental Example 2, spheres of HeLa cells were formed, and several tens of the spheres were added to each medium (1 mL) prepared above, the mixture was stood still at 37° C. for 1 hr, and the suspended state of the sphere cells was visually observed. As a result, it was confirmed that the spheres of HeLa cells maintained the suspended state in any of the above-mentioned medium compositions. Furthermore, it was confirmed that addition of an equal amount of the medium to the cell suspension and centrifugation (300 to 400G, for 5 min) thereof result in sedimentation and recovery of the spheres of HeLa cells. The suspended state of the spheres of HeLa cells cultured in the medium composition is each shown in FIG. 5. In addition, the viscosity measured in the same manner as in Analysis Example 1 is shown in Tables 7 and 8.

TABLE 7

| xanthan gum concentration % (w/v) | state | viscosity (mPa · s) | HeLa cell suspension/ sedimentation |
|---|---|---|---|
| 0.1 | liquid | 3.69 | suspension |
| 0.15 | liquid | 5.46 | suspension |
| 0.2 | liquid | 7.26 | suspension |

TABLE 8

| κ-carageenan, locust bean gum concentration % (w/v) | state | viscosity (mPa · s) | HeLa cell suspension/sedimentation |
|---|---|---|---|
| 0.03 | liquid | 1.34 | Suspension |
| 0.04 | liquid | 1.55 | Suspension |
| 0.05 | liquid | 1.95 | Suspension |

Reference Experimental Example 5: Cell Suspension Test Using Medium Composition Filtered with Filter A DMEM/F-12 medium composition containing 0.015% deacylated gellan gum (KELCOGEL CG-LA, manufactured by SANSHO Co., Ltd.) was prepared in the same manner as in Reference Experimental Example 2. Successively, this medium composition (1 mL) was filtered through 70 µm filter or 40 µm filter (manufactured by BD Falcon), 30 µm filter or 20 µm filter (manufactured by AS ONE Corporation), 10 µm filter (manufactured by Partec), or 5 µm filter, 1.2 µm filter, 0.45 µm filter or 0.2 µm filter (manufactured by Sartorius Stedim Japan). Spheres of HepG2 cells prepared in the same manner as in Reference Experimental Example 2 were added by about several tens spheres to the above-mentioned filtrates and stood at 37° C. for 1 hr, and the suspended state of the sphere cells was visually observed. As a result, it was confirmed that the spheres of HepG2 cells are maintained in a suspended state in the medium composition passed through a filter of not less than 10 µm, but sedimented in the medium composition passed through a filter of less than 5 µm. Furthermore, it was confirmed that centrifugation at room temperature, 300G, for 5 min, or addition of an equal amount of the medium and centrifugation at room temperature, 200G, for 5 min, of HepG2 cell spheres in a suspended state result in sedimentation and recovery of the spheres.

Reference Experimental Example 6: Sphere Formation Test

Figure 6:
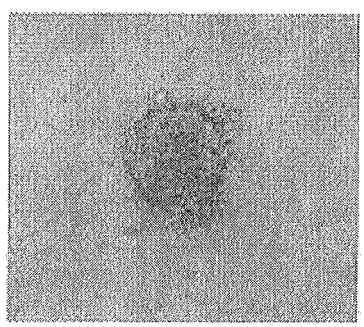
FIG. 6 is a Figure showing that spheres of HeLa cells could be formed in the medium composition.

In the same manner as in Reference Experimental Example 2, a composition of EMEM medium (manufactured by WAKO) containing 0.01% deacylated gellan gum (KELCOGEL CG-LA, manufactured by SANSHO Co., Ltd.) and 10% (v/v) fetal bovine serum was prepared. Successively, HeLa cells were added to a concentration of 1000 cells/mL, and dispensed to a 24-well plate (manufactured by Corning Incorporated). This plate was suspension-cultured by being stood still at 37° C. for 9 days, and formation of sphere was confirmed with a microscope. Furthermore, the sphere cells were sedimented by a centrifugation treatment (300G, for 5 min), and washed once with PBS (5 mL). A 100 µL trypsin-EDTA (ethylenediaminetetraacetic acid) solution (manufactured by WAKO) was added, and the mixture was incubated at 37° C. for 5 min. Here, to the obtained cell suspension (100 µL) was added EMEM medium (100 µL) containing 10% (v/v) fetal bovine serum, to a subset of the cell suspension was added Trypan Blue staining solution (manufactured by Invitrogen Corporation) at same amount, and the number of viable cells was measured by a hemocytometer (manufactured by ERMA INC.). As a result, it was confirmed that HeLa cell increases to 170000 cells/mL. The sphere of HeLa cell formed in the medium composition is shown in FIG. 6.

Reference Experimental Example 7: Optical Microscope Observation of Structure

Figure 7:
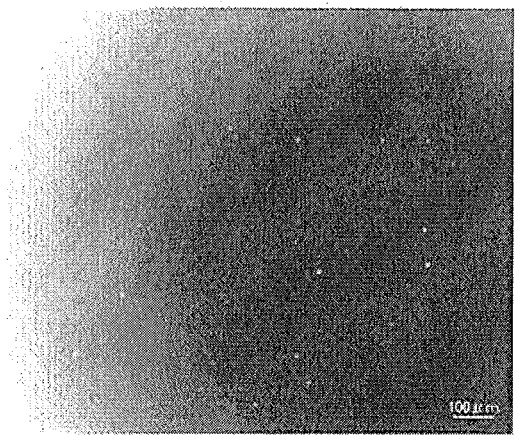
FIG. 7 is a Figure showing a film, which is one embodiment of the structure, wherein the concentration of the deacylated gellan gum in the medium composition was 0.02% (weight/volume).

Deacylated gellan gum (KELCOGEL CG-LA, manufactured by SANSHO Co., Ltd.) was suspended in pure water to 0.4% (w/v), and dissolved by stirring with heating at 90° C. DMEM/F-12 medium (manufactured by Aldrich, 95 mL) at a 2-fold concentration was placed in a 300 mL tall beaker, an aqueous deacylated gellan gum solution (5 mL) was added with stirring with a magnetic stirrer at room temperature, and the mixture was stirred as it was for 5 min to give a medium composition containing deacylated gellan gum at a final concentration of 0.02%. Furthermore, the medium composition was stirred by a homomixer (3000 rpm) for 5 min. The prepared medium composition was observed with an optical microscope (KEYENCE Corporation, BIOREVO BZ-9000). The observed structure is shown in FIG. 7.

Reference Experimental Example 8: Preparation by Mixing Heating Powder Medium and DAG Deacylated gellan gum (KELCOGEL CG-LA, manufactured by SANSHO Co., Ltd., 20 mg) and DMEM/F-12 medium (manufactured by Life Technologies, 1.58 g) were placed in a 200 ml Erlenmeyer flask, and pure water (100 mL) was poured therein. The mixture was sterilized at 121° C. for 20 min in an autoclave to prepare a DMEM/F-12 medium composition with a deacylated gellan gum concentration of 0.02%. To the prepared medium were added dextran beads Cytodex 1 (Size 200 µm, manufactured by GE Healthcare Life Sciences), and the dispersion state of the beads was confirmed by visual observation. For evaluation, a suspended state is ○, partial sedimentation/dispersed state is Δ, and sedimented state is x. The results are shown in Table 9.

TABLE 9

| deacylated gellan gum concentration % (w/v) | state | Cytodex1 dispersion |
| --- | --- | --- |
| 0.05 | liquid | ○ |
| 0.02 | liquid | ○ |
| 0.01 | liquid | ○ |

Reference Experimental Example 9: Preparation of Medium Composition Containing Polysaccharides Xanthan gum (KELTROL CG, manufactured by SANSHO Co., Ltd.) was suspended in pure water to a concentration of 0.5% (w/v), and dissolved by stirring with heating at 90° C. Similarly, 0.5% (w/v) aqueous solutions of sodium alginate (Duck alginic acid NSPM, manufactured by FOOD CHEMIFA Co., Ltd.), locust bean gum (GENUGUM RL-200-J, manufactured by SANSHO Co., Ltd.), K-carageenan (GENUGEL WR-80-J, manufactured by SANSHO Co., Ltd.) or diutan gum (KELCO CRETE DG-F, manufactured by SANSHO Co., Ltd.) were prepared.

Each of the aqueous solutions and 0.2 or 0.1% (w/v) deacylated gellan gum solution and DMEM/F-12 medium at a 10-fold concentration were mixed, and the mixture was heated at 80° C. for 30 min, allowed to cool to room temperature, and 7.5% aqueous sodium hydrogen carbonate solution was added to prepare DMEM/F-12 medium compositions containing deacylated gellan gum at a final concentration of 0.01, 0.02% (w/v) and other polysaccharide at a final concentration of 0.1, 0.2, 0.3, 0.4% (w/v). In addition, a medium containing deacylated gellan gum was prepared as mentioned above, and a powder of methylcellulose (cP400, manufactured by WAKO) was added. The mixture was stirred in an ice bath to dissolve methylcellulose to prepare DMEM/F-12 medium compositions containing deacylated gellan gum at a final concentration of 0.01, 0.02% (w/v) and other methylcellulose at a final concentration of 0.1, 0.2, 0.3, 0.4% (w/v).

Polystyrene beads (Size 500-600 µm, manufactured by Polysciences Inc.) were added to the medium prepared above, and the dispersion state of the beads was confirmed by visual observation. For evaluation, a suspended state is ○, partial sedimentation/dispersed state is Δ, and sedimented state is x. The results are shown in Table 10.

TABLE 10

| deacylated gellan gum concentration % (w/v) | polysaccharide concentration % (w/v) | xanthan gum | alginic acid Na | locust bean gum | methyl-cellulose | κ-carageenan | diutan gum |
|---|---|---|---|---|---|---|---|
| 0.01 | 0.1 | ○ | ○ | ○ | X | ○ | ○ |
|  | 0.2 | ○ | ○ | ○ | Δ/X | solidified | not measured |
|  | 0.3 | ○ | ○ | ○ | Δ/X | solidified | not measured |
|  | 0.4 | ○ | ○ | ○ | Δ/X | solidified | not measured |
| 0.02 | 0.1 | ○ | ○ | ○ | ○/X | ○ | ○ |
|  | 0.2 | ○ | ○ | ○ | ○ | solidified | not measured |
|  | 0.3 | ○ | ○ | ○ | ○ | solidified | not measured |
|  | 0.4 | ○ | ○ | ○ | ○ | solidified | not measured |

Reference Experimental Example 10: Viscosity Measurement of Medium Composition Containing Polysaccharides By a method similar to that for the polysaccharide mixture of Reference Experimental Example 9, DMEM/F-12 media containing deacylated gellan gum at a final concentration of 0.005, 0.01% (w/v) and other polysaccharide were prepared. The final concentration of polysaccharide was set to 0.1% (w/v) for xanthan gum, sodium alginate, locust bean gum, 0.2% (w/v) for methylcellulose, and 0.05% (w/v) for κ-carageenan and diutan gum. The state of each medium composition and the viscosity measured by a method similar to that in Analysis Example 1 are shown in Tables 11-16.

TABLE 11

| xanthan gum concentration % (w/v) | deacylated gellan gum concentration % (w/v) | state | viscosity (mPa·s) |
|---|---|---|---|
| 0.1 | 0.005 | liquid | 4.36 |
| 0.1 | 0.010 | liquid | 4.59 |

TABLE 12

| sodium alginate concentration % (w/v) | deacylated gellan gum concentration % (w/v) | state | viscosity (mPa·s) |
|---|---|---|---|
| 0.1 | 0.005 | liquid | 1.53 |
| 0.1 | 0.010 | liquid | 1.75 |

TABLE 13

| locust bean gum concentration % (w/v) | deacylated gellan gum concentration % (w/v) | state | viscosity (mPa·s) |
|---|---|---|---|
| 0.1 | 0.005 | liquid | 1.92 |
| 0.1 | 0.010 | liquid | 2.36 |

TABLE 14

| methylcellulose concentration % (w/v) | deacylated gellan gum concentration % (w/v) | state | viscosity (mPa·s) |
|---|---|---|---|
| 0.2 | 0.005 | liquid | 3.36 |
| 0.2 | 0.010 | liquid | 3.81 |

TABLE 15

| κ-carageenan concentration % (w/v) | deacylated gellan gum concentration % (w/v) | state | viscosity (mPa·s) |
|---|---|---|---|
| 0.05 | 0.005 | liquid | 1.04 |
| 0.05 | 0.010 | liquid | 1.28 |

TABLE 16

| diutan gum concentration % (w/v) | deacylated gellan gum concentration % (w/v) | state | viscosity (mPa·s) |
|---|---|---|---|
| 0.1 | 0.005 | liquid | 2.76 |
| 0.1 | 0.010 | liquid | 3.04 |

Reference Experimental Example 11: Preparation of Medium Composition with Changed Divalent Metal Ion Concentration Using DMEM/F-12 (D9785, manufactured by Aldrich) free of calcium chloride, magnesium sulfate and magnesium chloride and in the same manner as in the method of Reference Experimental Example 8, DMEM/F-12 medium composition containing 0.02% (w/v) deacylated gellan gum was prepared. DMEM/F-12 medium compositions added with calcium chloride or magnesium sulfate, and magnesium chloride such that the final concentration was set to the defined amount of DMEM/F-12 medium were prepared. In view of the defined composition of DMEM/F-12 medium, each final concentration was set to 0.116 g/L for calcium chloride, 0.049 g/L for magnesium sulfate, and 0.061 g/L for magnesium chloride.

To the prepared medium composition were added dextran beads Cytodex 1 (manufactured by GE Healthcare Life Sciences), and the dispersion state of the beads was confirmed 2 days later by visual observation. For evaluation, a suspended state is ○, partial sedimentation/dispersed state is Δ, and sedimented state is x. The results are shown in Table 17.

TABLE 17

| deacylated gellan gum concentration % (w/v) | calcium chloride | magnesium sulfate magnesium chloride | Cytodex1 dispersion |
|---|---|---|---|
| 0.02 | + | + | ○ |
| 0.02 | + | − | ○ |
| 0.02 | − | + | Δ |
| 0.02 | − | − | X |

Reference Experimental Example 12: Preparation of Medium Composition Later Added with Divalent Metal Cations A salt solution was prepared by dissolving 0.1% (w/v) deacylated gellan gum solution, a 5-fold concentration of DMEM/F-12 medium (not containing calcium chloride, magnesium sulfate and magnesium chloride, D9785, manufactured by Aldrich), calcium chloride (1167 mg), magnesium sulfate (489 mg) and magnesium chloride (287 mg) in pure water (300 mL). An aqueous deacylated gellan gum solution and pure water were placed in a 200 mL tall beaker, and the solution was stirred at 200 rpm using an anchor type stirring blade. Solution A, which is a mixture of the medium solution and water, was added, and the mixture was directly stirred for 10 min. Then, the salt solution was added, and 7.5% aqueous sodium hydrogen carbonate solution (1.6 mL) was further added to prepare DMEM/F-12 medium compositions containing deacylated gellan gum at a final concentration of 0.02%. The mixed amount of each solution is shown in the Table. After for 4 hr from the preparation, 6 medium compositions were subjected to a dispersion evaluation of polystyrene beads and Cytodex1. The results are shown in Tables 18, 19.

TABLE 18

| | 0.1% (w/v) deacylated gellan gum aqueous solution | pure water | solution A 5-fold concentration DMEM/F-12 | pure water | salt solution calcium chloride magnesium chloride magnesium sulfate |
|---|---|---|---|---|---|
| 1 | 20 mL | 10 mL | 20 mL | 50 mL | none |
| 2 | 20 mL | 10 mL | 20 mL | 47 mL | 3 mL |
| 3 | 20 mL | 10 mL | 20 mL | 40 mL | 3 mL/water 7 mL |
| 4 | 20 mL | 30 mL | 20 mL | 30 mL | none |
| 5 | 20 mL | 30 mL | 20 mL | 27 mL | 3 mL |
| 6 | 20 mL | 30 mL | 20 mL | 20 mL | 3 mL/water 7 mL |

TABLE 19

| | deacylated gellan gum concentration % (w/v) | salt solution | polystyrene bead dispersion | Cytodex1 dispersion |
|---|---|---|---|---|
| 1 | 0.02 | − | X | X |
| 2 | 0.02 | + | ○ | ○ |
| 3 | 0.02 | + | ○ | ○ |
| 4 | 0.02 | − | X | X |
| 5 | 0.02 | + | ○ | ○ |
| 6 | 0.02 | + | ○ | ○ |

Reference Experimental Example 13: Preparation of Various Medium Compositions

A 0.1% (w/v) deacylated gellan gum solution and a medium solution having a high concentration were prepared. As a medium solution having a high concentration, MEM having a 10-fold concentration (MO268, manufactured by Aldrich), RPMI-1640 having a 10-fold concentration (R6504, manufactured by Aldrich) and DMEM having a 5-fold concentration (high-pressure sterilization corresponding medium, manufactured by Nissui) were prepared. A 0.1% (w/v) deacylated gellan gum solution, each high concentration medium, and pure water for adjusting concentration were mixed, and the mixture was heated at 80° C. for 30 min. The mixture was allowed to cool to room temperature, and 7.5% aqueous sodium hydrogen carbonate solution was added to prepare medium compositions containing deacylated gellan gum at a final concentration of 0.01, 0.02, 0.03% (w/v). The prepared 6 medium compositions were evaluated for the suspension and dispersion state of polystyrene beads and dextran beads Cytodex1, wherein a suspended state is ○, partial sedimentation/dispersed state is Δ, and sedimented state is x. The results are shown in Tables 20, 21.

TABLE 20

| MEM medium | | | |
|---|---|---|---|
| deacylated gellan gum concentration % (w/v) | state | polystyrene bead dispersion | Cytodex1 dispersion |
| 0.01 | liquid | Δ | Δ |
| 0.02 | liquid | ○ | ○ |
| 0.03 | liquid | ○ | ○ |

TABLE 21

| DMEM medium | | | |
|---|---|---|---|
| deacylated gellan gum concentration % (w/v) | state | polystyrene bead dispersion | Cytodex1 dispersion |
| 0.01 | liquid | Δ | Δ |
| 0.02 | liquid | ○ | ○ |
| 0.03 | liquid | ○ | ○ |

Reference Experimental Example 14: Particle Size Distribution Measurement of Medium Composition Containing Deacylated Gellan Gum)

According to Reference Example 1, DMEM/F-12 medium composition containing 0.038% (w/v) deacylated gellan gum was prepared. The medium was prepared by stirring at 3000 rpm or 6000 rpm for 1 min by a homomixer. The particle size distribution of the medium composition was measured by Beckman Instruments Coulter, Inc. Multisizer 4 (precise particle size distribution measuring apparatus by Coulter principle) and the median size (d50) of the volume standard particle size distribution was determined. The results are shown in Table 22.

TABLE 22

| homomixer rotation number in medium preparation | d50 (μm) |
|---|---|
| 3000 rpm | 1.709 |
| 6000 rpm | 1.499 |

Reference Experimental Example 15: Phosphorylation of Deacylated Gellan Gum

Deacylated gellan gum (1 g) and pure water (40 mL) were measured off in a 100 mL glass test tube, and the mixture was heated at 100° C. for 30 min to prepare a suspension. To this suspension was added aqueous phosphoric acid solution (85%, 1 g), and the mixture was heated under reflux for 5 hr. Thereafter, it was allowed to cool to room temperature while stirring for 12 hr, and the obtained white suspension was poured into 99% ethanol (500 mL). The resulting floc white solid was collected by filtration and dried to give a pale-brown solid (0.4 g) as a phosphorylated substance of deacylated gellan gum. Introduction of a phosphate group was confirmed by Fourier-transform infrared spectroscopic analysis (manufactured by SHIMADZU CORPORATION, IR-Prestage 21) (1700 cm-1; P—OH, 1296 cm-1, 1265 cm-1; P=O). The pale-brown solid was decomposed by a micro wave heating digestion apparatus (ETHOS TC, manufactured by Milestone General), and the content of the phosphorus atom was measured by an inductively coupled plasma emission spectroscopic analyzer (ICP-OES) (SPS 5520, manufactured by SII NanoTechnology). The result was 3.5 wt % (n=2).

Reference Experimental Example 16: Preparation of Medium Composition Containing Phosphorylated Deacylated Gellan Gum An optional amount of phosphorylated deacylated gellan gum (30 mg) and DMEM/F-12 medium (manufactured by Life Technologies, 1.56 g) were placed in a 200 mL Erlenmeyer flask, and pure water (100 mL) was poured therein. The mixture was sterilized at 121° C. for 20 min in an autoclave to prepare a DMEM/F-12 medium composition having a deacylated gellan gum concentration of 0.03%. To the prepared medium were added dextran beads Cytodex 1 (manufactured by GE Healthcare Life Sciences), and the dispersion state of the beads was confirmed by visual observation. A dispersed state of the beads was found at a phosphorylated deacylated gellan gum concentration of 0.03% (w/v).

Reference Experimental Example 17: Preparation of Medium Composition Containing Deacylated Gellan Gum An aqueous deacylated gellan gum solution and a medium solution were mixed at the rates shown in the following Table to prepare a DMEM/F-12 medium composition having a deacylated gellan gum concentration of 0.02%, and the dispersion state of polystyrene beads (Size 500-600 μm, manufactured by Polysciences Inc.) was evaluated. The results are shown in Tables 23 and 24. By standing for 1 day or longer, the styrene beads were dispersed under all conditions.

TABLE 23

| deacylated gellan gum/pure water | DMEM/F12 powder medium/pure water | standing time |
| --- | --- | --- |
| 20 mg/10 mL | 1.56 g/90 mL | for 5 min |
| 20 mg/20 mL | 1.56 g/80 mL | for 5 min |
| 20 mg/30 mL | 1.56 g/70 mL | for 5 min |
| 20 mg/40 mL | 1.56 g/60 mL | 6 h |
| 20 mg/50 mL | 1.56 g/50 mL | 6 h |
| 20 mg/60 mL | 1.56 g/40 mL | 6 h |

TABLE 23-continued

| deacylated gellan gum/pure water | DMEM/F12 powder medium/pure water | standing time |
| --- | --- | --- |
| 20 mg/70 mL | 1.56 g/30 mL | 6 h |
| 20 mg/80 mL | 1.56 g/20 mL | 1 day |
| 20 mg/90 mL | 1.56 g/10 mL | 1 day |

"DMEM/F12 powder medium/pure water" was added to "deacylated gellan gum/pure water"

TABLE 24

| deacylated gellan gum/pure water | DMEM/F12 powder medium/pure water | standing time |
| --- | --- | --- |
| 20 mg/10 mL | 1.56 g/90 mL | for 5 min |
| 20 mg/20 mL | 1.56 g/80 mL | for 5 min |
| 20 mg/30 mL | 1.56 g/70 mL | 1 h |
| 20 mg/40 mL | 1.56 g/60 mL | 6 h |
| 20 mg/50 mL | 1.56 g/50 mL | 6 h |
| 20 mg/60 mL | 1.56 g/40 mL | 6 h |
| 20 mg/70 mL | 1.56 g/30 mL | 1 day |
| 20 mg/80 mL | 1.56 g/20 mL | 1 day |
| 20 mg/90 mL | 1.56 g/10 mL | 1 day |

"Deacylated gellan gum/pure water" was added to "DMEM/F12 powder medium/pure water"

Reference Experimental Example 18: Preparation of Medium Composition Using Filter Deacylated gellan gum (KELCOGEL CG-LA, manufactured by SANSHO Co., Ltd.) was suspended in ultrapure water (Milli-Q water) to a final concentration of 0.02 or 0.04% (w/v), and dissolved by heating at 90° C. for 30 min or at 121° C. for 20 min. Furthermore, this aqueous solution (100 mL) was filtered with a polyethersulfone membrane filter having a pore size of 0.22 μm (manufactured by Corning Incorporated). Successively, this filtrate was mixed with a 2- to 4-fold concentration of DMEM/F-12 medium (manufactured by Sigma Aldrich), and the mixture was shaken by a mild mixer (SI-24, manufactured by TAITEC Co., Ltd.) for 1 hr to prepare medium compositions containing deacylated gellan gum at a final concentration of 0.01 or 0.015% (w/v) (e.g., 25 mL each of 0.02% (w/v) aqueous deacylated gellan gum solution and DMEM/F-12 medium having a 2-fold concentration were mixed to prepare 0.01% (w/v) deacylated gellan gum medium composition (50 mL)). By a method similar to that in Reference Experimental Example 2, spheres of HepG2 cells were formed, and several tens of the spheres were added to the medium (1 mL) prepared above, stood at 37° C., of the suspended state of the sphere cells was visually observed after for 1 hr and one night. As a result, it was confirmed that the spheres of HepG2 cells are maintained in a suspended state in all of the above-mentioned medium composition. Furthermore, two-fold volume of the medium was added, and the cell suspension was centrifuged (500G, for 5 min). It was confirmed that the spheres of HepG2 cells are sedimented, and the cells can be recovered in all medium compositions. The dispersed state of the sphere after one night was confirmed by visual observation and evaluated, wherein a suspended and dispersed state is ○, partial sedimentation/dispersed state is Δ, and sedimented state is x. The evaluation results are shown in Table 25.

TABLE 25

| aqueous deacylated gellan gum solution concentration (%) | temperature (° C.) during dissolution | deacylated gellan gum concentration (%) of medium composition | suspending effect of HepG2 cells |
|---|---|---|---|
| 0.02 | 90 | 0.010 | ○ |
|  |  | 0.015 | ○ |
|  | 120 | 0.010 | ○ |
|  |  | 0.015 | ○ |
| 0.04 | 90 | 0.010 | ○ |
|  |  | 0.015 | ○ |
|  | 120 | 0.010 | ○ |
|  |  | 0.015 | ○ |

Reference Experimental Example 19: Cell Proliferation Test by Culturing Cell Line-Derived Sphere Human embryonic kidney cell line HEK293 (manufactured by DS PHARMA BIOMEDICAL CO., LTD.) was suspended in EMEM medium containing 10% (v/v) fetal bovine serum (manufactured by WAKO) at 250000 cells/mL, and this suspension (10 mL) was plated on EZ SPHERE (manufactured by ASAHI GLASS CO., LTD.) and cultured for 2 days in a $CO_2$ incubator (5% $CO_2$). A suspension (10 mL) of the spheres (diameter 100-200 μm) of HEK293 cells obtained here was centrifuged (200G, for 5 min) to allow for sphere sedimentation, the supernatant was removed and the sphere was suspended in 1 mL. Successively, the medium (10 mL) was added to the sphere suspension (200 μL, cell number about 200000) to suspend them and the suspension was transferred to a flat bottom tube (manufactured by BM Equipment Co., Ltd.). Similarly, using a medium composition obtained by adding 0.015% (w/v) deacylated gellan gum (KELCOGEL CG-LA, manufactured by SANSHO Co., Ltd.) to the above-mentioned medium, a sphere suspension was produced and transferred to a flat bottom tube (manufactured by BM Equipment Co., Ltd.). The medium composition added with 0.015% (w/v) deacylated gellan gum was prepared by first suspending deacylated gellan gum (KELCOGEL CG-LA, manufactured by SANSHO Co., Ltd.) in ultrapure water (Milli-Q water) to 0.3% (w/v), dissolving same by stirring with heating at 90° C., sterilizing this aqueous solution at 121° C. for 20 min in an autoclave, and adding the solution at 1/20 dilution to EMEM medium containing 10% (v/v) fetal bovine serum.

After static culture of the above-mentioned sphere suspension in a $CO_2$ incubator (5% $CO_2$) at 37° C. for 5 days, a two-fold volume of the medium was added. The mixture was centrifuged (500G, for 5 min) to allow for sphere sedimentation, and the supernatant was removed. Successively, the recovered sphere was washed once with PBS (10 mL), 1 mL of trypsin-EDTA (ethylenediaminetetraacetic acid) solution (manufactured by WAKO) was added, and the mixture was incubated at 37° C. for 5 min. The above-mentioned medium (9 mL) was added, and the cells were collected by centrifugation (500G, for 5 min). To a part of the obtained cell suspension (2 mL) was added the same amount of a Trypan Blue staining solution (manufactured by Invitrogen Corporation), and the numbers of the viable cells and dead cells were measured by a hemocytometer (manufactured by ERMA INC.). As a control, a medium composition free of deacylated gellan gum was produced and a similar experiment was performed.

As a result, it was confirmed that, using the medium composition, the spheres of HEK293 cells can be cultivated in a suspended state, and the cells efficiently proliferate in the medium composition. Furthermore, the medium composition was confirmed to show a small rate of the dead cells as compared to a medium composition free of deacylated gellan gum when the cells were proliferated, and have a superior cell proliferation promoting effect. The sphere cultured in an existing medium sedimented on the bottom of the culture container.

The relative number of the HEK293 cells is shown in Table 26, wherein the number of the cells cultured in a medium free of deacylated gellan gum is 1. In addition, the relative rate of the dead cells is shown in Table 27, wherein the rate of the dead cells cultured in a medium free of deacylated gellan gum (dead cell number/viable cell number) is 1.

TABLE 26

| deacylated gellan gum |  | HEK293 cells |
|---|---|---|
| absent | relative cell number | 1.0 |
| present | relative cell number | 1.6 |

TABLE 27

| deacylated gellan gum |  | HEK293 cells |
|---|---|---|
| absent | relative dead cell rate | 1.0 |
| present | relative dead cell rate | 0.3 |

Reference Experimental Example 20: Cell Proliferation Test by Culturing Insect Cell Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v) to Sf-900 (registered trade mark) III SFM medium (manufactured by Gibco). Successively, *Spodoptera frugiperda* derived Sf9 cells (manufactured by Gibco) were inoculated to the above-mentioned medium composition added with deacylated gellan gum at 100000 cells/mL, and dispensed to the wells of a 24-well flat bottom microplate (manufactured by Corning Incorporated) at 1 mL/well. The cell suspensions were cultured by being stood still in an incubator at 25° C. for 5 days. Thereafter, a part of the culture medium was recovered, the same amount of Trypan Blue staining solution (manufactured by Invitrogen Corporation) was added, and the number of viable cells was measured by a hemocytometer (manufactured by ERMA INC.). As a control, a medium composition free of deacylated gellan gum was produced and subjected to a similar experiment.

As a result, it was confirmed that, using the medium composition, Sf9 cell can be uniformly cultivated in a suspended state, and proliferates in the medium composition. Furthermore, it was confirmed that the medium composition is superior in the effect of promoting cell proliferation when the cells is proliferated, as compared to a medium composition free of deacylated gellan gum. The cell number of Sf9 cells after suspension static culture for 5 days is shown in Table 28.

TABLE 28

| deacylated gellan gum | Sf9 cell number (×10000) |
| --- | --- |
| absent | 33.5 |
| present | 47.4 |

Reference Experimental Example 21: Cell Proliferation Test by Culturing CD34 Positive Cells Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.015% (w/v), 20 ng/mL thrombopoietin (manufactured by WAKO) and 100 ng/mL stem cell factor (SCF, manufactured by WAKO) to StemSpan SFEM medium (manufactured by StemCell Technologies). Successively, human cord blood-derived CD34 positive cells (manufactured by Lonza) were inoculated to the above-mentioned medium composition added with deacylated gellan gum to 10000 cells/mL, and dispensed to the wells of a 24-well flat bottom microplate (manufactured by Corning Incorporated) at 1 mL/well. The cell suspensions were subjected to static culture at 37° C. for 7 days in a $CO_2$ incubator (5% $CO_2$). Thereafter, a part of the culture medium was recovered, the same amount of Trypan Blue staining solution (manufactured by Invitrogen Corporation) was added, and the number of viable cells was measured by a hemocytometer (manufactured by ERMA INC.). A 3-fold volume of the medium was added to the culture medium and the mixture was centrifuged (500G, for 5 min) to allow for sedimentation of all cells. As a control, a medium composition free of deacylated gellan gum was produced and subjected to a similar experiment.

As a result, it was confirmed that, using the medium composition, CD34 positive cells can be uniformly cultivated in a suspended state, and proliferates in the medium composition. Furthermore, the medium composition was confirmed to show a cell proliferation promoting effect of the level equal to or more than that of the existing media without deacylated gellan gum. In addition, it was confirmed that centrifugation results in sedimentation of the cells and the cells can be recovered. The relative number of the cells proliferated from the CD34 positive cells after suspension static culture for 7 days, wherein the number of the cells cultured in a medium free of deacylated gellan gum is 1, is shown in Table 29.

TABLE 29

| deacylated gellan gum | relative cell number |
| --- | --- |
| absent | 1.0 |
| present | 1.2 |

Reference Experimental Example 22: Sphere Formation Test

Figure 8:
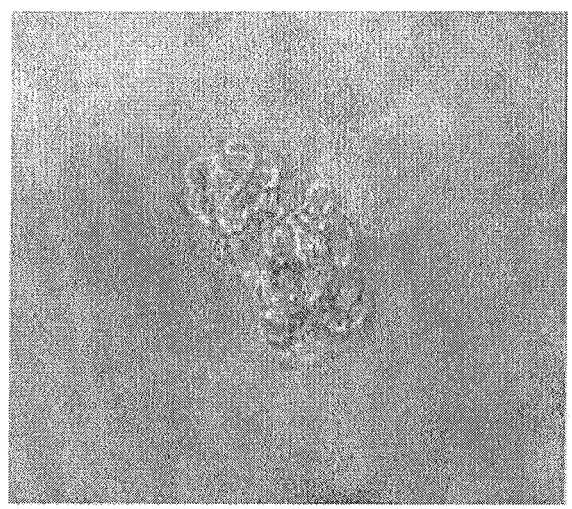
FIG. 8 is a Figure showing that spheres of HepG2 cells could be formed in the medium composition.

In the same manner as in Reference Experimental Example 2, a composition of DMEM medium (manufactured by WAKO) containing 0.015% deacylated gellan gum (KELCOGEL CG-LA, manufactured by SANSHO Co., Ltd.) and 10% (v/v) fetal bovine serum was prepared. Successively, HepG2 cells were added to a cell concentration of 15000 cells/mL, and dispensed by 1 mL to a 24-well plate (manufactured by Corning Incorporated). This plate was suspension-cultured by being stood still at 37° C. for 7 days, and formation of sphere was confirmed with a microscope. Furthermore, the sphere cells were sedimented by a centrifugation treatment (400G, for 5 min), and washed once with PBS (5 mL). A 100 µL trypsin-EDTA (ethylenediaminetetraacetic acid) solution (manufactured by WAKO) was added, and the mixture was incubated at 37° C. for 5 min. Here, to the obtained cell suspension (100 µL) was added DMEM medium (100 µL) containing 10% (v/v) fetal bovine serum, to a subset of the cell suspension was added Trypan Blue staining solution (manufactured by Invitrogen Corporation) at same amount, and the number of viable cells was measured by a hemocytometer (manufactured by ERMA INC.). As a result, it was confirmed that HepG2 cells formed a sphere in the medium composition and increased to 80800 cells/mL. The sphere of HepG2 cells formed in the medium composition is shown in FIG. 8.

Reference Experimental Example 23: Cell Suspension Test Using Cell Line-Derived Sphere Diutan gum (KELKO-CRETE DG, manufactured by SANSHO Co., Ltd.) was suspended in ultrapure water (Milli-Q water) to a concentration of 0.3% (w/v), and dissolved by stirring with heating at 90° C. Using this aqueous solution, DMEM/F-12 medium compositions having a final diutan gum concentration of 0.1% (w/v) were prepared. In addition, an aqueous solution containing 0.5% (w/v) native-type gellan gum (KELCO gel HT, manufactured by San-Ei Gen F.F.I., Inc.) was prepared by heating at 90° C. Using the aqueous solution, DMEM/F-12 medium (manufactured by Sigma Ltd.) compositions containing 0.05 or 0.1% (w/v) native-type gellan gum was prepared.

In the same manner as in Reference Experimental Example 2, spheres of HeLa cells were produced, and several tens of spheres were added to each medium (1 mL) prepared above, the mixture was stood still at 37° C. for 1 hr, and the suspended state of the sphere cells was visually observed. As a result, it was confirmed that the spheres of HeLa cells maintained the suspended state in any of the above-mentioned medium compositions. Furthermore, it was confirmed that centrifugation (200G, for 5 min) of the cell suspension containing 0.1% (w/v) diutan gum result in sedimentation and recovery of the spheres of HeLa cells.

Reference Experimental Example 24: Cell Suspension Test Using Magnetic Beads Having Cell Adhesion Ability-1

A suspension of GEM (registered trade mark, Global Eukaryotic Microcarrier, manufactured by GL Sciences Inc.) coated with laminin or fibronectin was dispensed by 500 µL to a 1.5 mL volume micro test tube (manufactured by Eppendorf), GEM was accumulated from the above-mentioned GEM suspension by using a magnet stand (TA4899N12, manufactured by TAMAGAWA SEIKI CO., LTD.) and the solvent was removed. Furthermore, GEM was washed twice with DMEM medium (manufactured by WAKO, 500 µL) containing 10% (v/v) fetal bovine serum, and suspended in the same medium (500 µL). This suspension was dispensed to a Sumilon cell tight plate 24F (manufactured by SUMITOMO BAKELITE), which is a cell low adhesion plate, at 50 µL per 1 well. Successively, HepG2 cells prepared separately were added at 250000 cells/mL, and the final volume was adjusted with the same medium to 500 μL/well. This cell suspension was manually stirred, and the plate was stood overnight in a $CO_2$ incubator (5% $CO_2$). After confirmation of cell adhesion on GEM with a microscope, the cell suspension was transferred to a 1.5 mL micro test tube (manufactured by Eppendorf), cell-attached GEM was accumulated the above-mentioned magnet stand and the supernatant was removed.

By a method similar to that in Reference Experimental Example 2, a DMEM medium (manufactured by WAKO) composition containing 0.015% of deacylated gellan gum (KELCOGEL CG-LA, manufactured by SANSHO Co., Ltd.) and 10% (v/v) fetal bovine serum was prepared. This medium composition or the above medium free of deacylated gellan gum was each added by 1 mL to the HepG2 cell-attached GEM (laminin or fibronectin-coated) prepared above, suspended, and transferred to Sumilon cell tight plate 24F. Successively, this plate was stood for 6 days in a $CO_2$ incubator (5% $CO_2$), and the cell culture medium was transferred to a 1.5 mL micro test tube (manufactured by Eppendorf), the cell-attached GEM was accumulated while gently pipetting on the above-mentioned magnet stand, and the supernatant was removed. GEM was washed once with PBS (1 mL), 200 μL of trypsin-EDTA (ethylenediaminetetraacetic acid) solution (manufactured by WAKO) was added, and the mixture was incubated at 37° C. for 10 min. To 200 μL of the cell suspension obtained here was added 800 μL of DMEM medium containing 10% (v/v) fetal bovine serum, the same amount of Trypan Blue staining solution (manufactured by Invitrogen Corporation) was added to a part of the cell suspension, and the number of viable cells was measured by a hemocytometer (manufactured by ERMA INC.).

As a result, it was confirmed that, using the medium composition, GEM adhered with HepG2 cells can be cultivated in a suspended state, and efficiently proliferates in the medium composition. Furthermore, it was confirmed that the medium composition shows a cell proliferation promoting effect superior to that of the existing media free of deacylated gellan gum. In addition, it was confirmed that, using magnetic force, HepG2 cell-attached GEM can be collected from the medium composition, and further, HepG2 cells can be recovered from this GEM.

Figure 9:
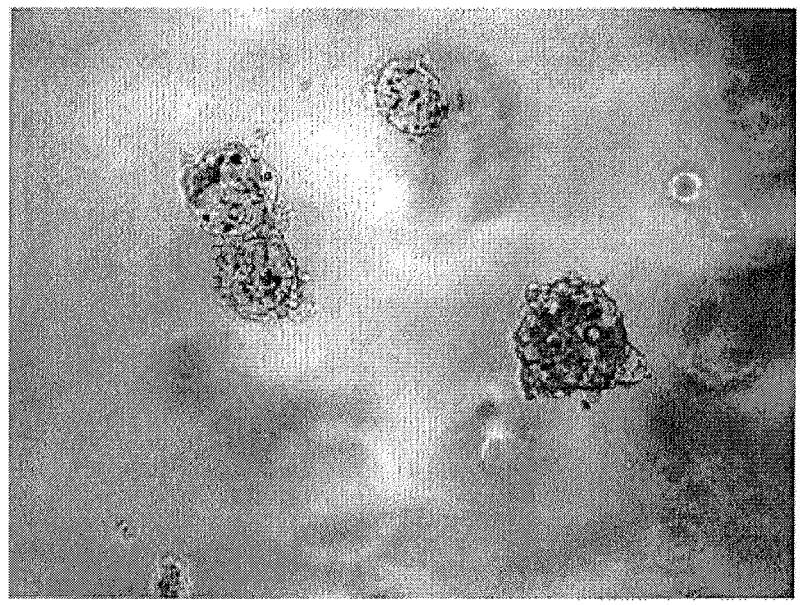
FIG. 9 is a Figure showing the suspended state of laminin-coated GEM attached with HepG2 cells, when it was cultured in the medium composition.

The cell number of HepG2 cells when cultured for 6 days on GEM in a deacylated gellan gum-containing or -free medium is shown in Table 30. In addition, the suspended state of HepG2 cell-attached laminin-coated GEM when cultured in the medium composition is shown in FIG. 9.

TABLE 30

| deacylated gellan gum | HepG2 cell number (×10000/mL) | |
| --- | --- | --- |
| | laminin coated GEM | fibronectin coated GEM |
| absent | 50.0 | 54.7 |
| present | 112.3 | 94.0 |

Reference Experimental Example 25: Cell Suspension Test Using Magnetic Beads Having Cell Adhesion Ability-2

In the same manner as in Reference Experimental Example 24, fibronectin-coated GEM (registered trade mark, Global Eukaryotic Microcarrier, manufactured by GL Sciences Inc.) was suspended in MF-Medium (registered trade mark) mesenchymal stem cell proliferation medium (manufactured by TOYOBO CO., LTD.). This suspension was dispensed to a Sumilon cell tight plate 24F (manufactured by SUMITOMO BAKELITE), which is a cell low adhesion plate, at 50 μL per 1 well. Successively, separately prepared human bone marrow-derived mesenchymal stem cell (manufactured by Cell Applications) was added at 250000 cells/mL and, in the same manner as in Reference Experimental Example 24, this plate was stood overnight in a $CO_2$ incubator (5% $CO_2$) to prepare GEM adhered with mesenchymal stem cells.

By a method similar to that in Reference Experimental Example 2, an MF-Medium (registered trade mark) mesenchymal stem cell proliferation medium (manufactured by TOYOBO CO., LTD.) composition containing 0.015% of deacylated gellan gum (KELCOGEL CG-LA, manufactured by SANSHO Co., Ltd.) was prepared. This medium composition or the above medium free of deacylated gellan gum was each added by 1 mL to the mesenchymal stem cell-attached GEM (fibronectin-coated) prepared above, suspended, and transferred to Sumilon cell tight plate 24F. Successively, this plate was stood for 4 days in a $CO_2$ incubator (5% $CO_2$), and the cell culture medium was transferred to a 1.5 mL micro test tube (manufactured by Eppendorf), the cell-attached GEM was accumulated while gently pipetting on the above-mentioned magnet stand, and the supernatant was removed. GEM was washed once with PBS (1 mL), 200 μL of trypsin-EDTA (ethylenediaminetetraacetic acid) solution (manufactured by WAKO) was added, and the mixture was incubated at 37° C. for 10 min. To 200 μL of the cell suspension obtained here was added 800 μL of DMEM medium containing 10% (v/v) fetal bovine serum, the same amount of Trypan Blue staining solution (manufactured by Invitrogen Corporation) was added to a part of the cell suspension, and the number of viable cells was measured by a hemocytometer (manufactured by ERMA INC.).

As a result, it was confirmed that, using the medium composition, GEM adhered with mesenchymal stem cells can be cultivated in a suspended state, and efficiently proliferates in the medium composition. Furthermore, it was confirmed that the medium composition shows a cell proliferation promoting effect superior to that of the existing media without deacylated gellan gum. In addition, it was confirmed that, using magnetic force, mesenchymal stem cell-attached GEM can be collected from the medium composition, and further the mesenchymal stem cells can be recovered from this GEM.

The cell number of mesenchymal stem cells when cultured for 4 days on GEM in a deacylated gellan gum-containing or -free medium is shown in Table 31.

TABLE 31

| deacylated gellan gum | mesenchymal stem cell number (×10000/mL) |
| --- | --- |
| absent | 11.3 |
| present | 20.9 |

Reference Experimental Example 26: Cell Suspension Test Using Alginic Acid Bead

The following test was performed according to the method of an alginic acid three-dimensional culture kit manufactured by PG Research. Separately prepared HepG2 cells were added to a sodium alginate solution (manufactured by PG research, 2.5 mL) at 400000 cells/mL, and human recombinant laminin 511 (manufactured by Veritas Ltd.) was further added at 5 μg/mL to prepare a cell suspension. The cell suspension was recovered with a 5 mL syringe (manufactured by TERUMO CORPORATION) having a gavage needle, and a 22G injection needle (manufactured by TERUMO CORPORATION) was set to this syringe. Successively, the cell suspension was added by 10 drops to each well of a 24 well flat bottom microplate (manufactured by PG research) added with 2 mL each of an aqueous calcium chloride solution (manufactured by PG research). The mixture was stood for 10 min at room temperature, formation of alginic acid bead was confirmed, the calcium chloride solution was removed, PBS (2 mL) was added, and the mixture was stood at room temperature for 15 min. Furthermore, PBS was removed, DMEM medium (manufactured by WAKO, 2 mL) containing 10% (v/v) fetal bovine serum was added and the mixture was stood at room temperature for 15 min. The medium was removed, DMEM medium (manufactured by WAKO) composition containing 0.03% deacylated gellan gum (KELCOGEL CG-LA, manufactured by SANSHO Co., Ltd.) and 10% (v/v) fetal bovine serum, which was prepared by a method similar to that in Reference Experimental Example 2, or the above medium free of deacylated gellan gum was added by 1 mL to each well, and the mixture was subjected to static culture for 8 days in a $CO_2$ incubator (5% $CO_2$). The medium was exchanged on day 4 of culture.

The cultured alginic acid beads were transferred to a 1.5 mL micro test tube (manufactured by Eppendorf) using a 1 mL tip, a sodium citrate solution (1 mL, manufactured by PG research) was added to each tube, and the mixture was stirred at room temperature for 15 min to dissolve the alginic acid beads. Successively, cells were sedimented by centrifugation at 300G for 3 min and the supernatant was removed. To the cells was added 200 μL of trypsin-EDTA (ethylenediaminetetraacetic acid) solution (manufactured by WAKO), and the mixture was incubated at 37° C. for 5 min. To the obtained cell suspension (200 μL) was added 800 μL of DMEM medium containing 10% (v/v) fetal bovine serum, and to a part of the cell suspension was added the same amount of Trypan Blue staining solution (manufactured by Invitrogen Corporation), and the number of the viable cells was measured by a hemocytometer (manufactured by ERMA INC.).

As a result, it was confirmed that, using the medium composition, alginic acid bead-embedded HepG2 cells can be cultivated in a suspended state, and efficiently proliferates in the medium composition. Furthermore, it was confirmed that the medium composition shows a cell proliferation promoting effect superior to that of the existing media without deacylated gellan gum.

Figure 10:
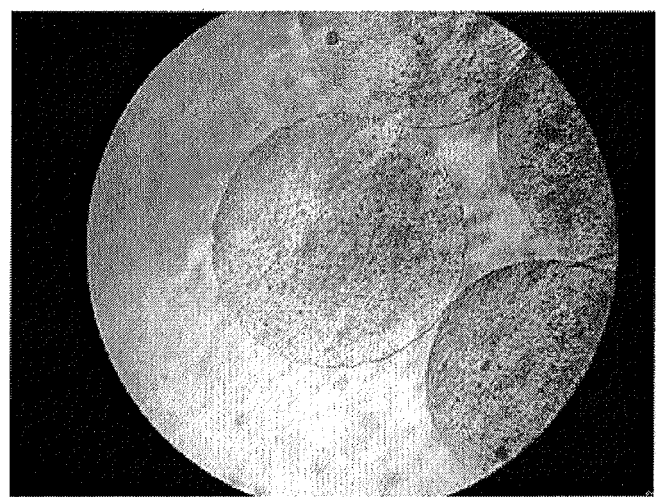
FIG. 10 is a Figure showing the suspended state of alginic acid beads in which HepG2 cells were embedded, when they were cultured in the medium composition.

The cell number of HepG2 cells when cultured in alginic acid beads in a deacylated gellan gum-containing or -free medium for 8 days is shown in Table 32. In addition, the suspended state when the HepG2 cell-embedded alginic acid beads so were cultured in the medium composition is shown in FIG. 10.

TABLE 32

| deacylated gellan gum | HepG2 cell number (×10000/mL) |
|---|---|
| absent | 34.9 |
| present | 51.8 |

Reference Experimental Example 27: Cell Suspension Test Using Collagen Gel Capsule A: tissue culture collagen Cell matrix (registered trade mark) Type I-A (cell matrix, manufactured by Nitta Gelatin Inc.), B: 10-fold concentration of DMEM/F-12 medium (manufactured by Aldrich), C: reconstitution buffer (obtained by adding sodium hydrogen carbonate (2.2 g), HEPES (4-(2-hydroxyethyl)-1-piperazineethanesulfonic acid)) (4.77 g) to 0.05N sodium hydroxide solution (100 mL) and subjecting the mixture to filtration sterilization) were mixed at A:B:C=8:1:1 while cooling in ice. Furthermore, human recombinant laminin 511 (manufactured by Veritas Ltd.) was added at 5 μg/mL to prepare a collagen mixed solution (500 μL). To the mixed solution was added separately-prepared HepG2 cells at 200000 cell/mL, and the total amount was recovered using a 1.5 mL syringe (manufactured by TERUMO CORPORATION) with a 25G injection needle (manufactured by TERUMO CORPORATION). Successively, the cell suspension was added dropwise by one drop to a flat bottom tube (manufactured by BM Equipment Co., Ltd.) containing DMEM medium (manufactured by WAKO) (10 mL) containing 10% (v/v) fetal bovine serum and incubated in advance at 37° C. using the above-mentioned syringe. The mixture was incubated in a water bath at 37° C. for 10 min and formation of an indeterminate collagen gel capsule with a diameter of about 2 mm was confirmed, deacylated gellan gum (KELCOGEL CG-LA, manufactured by SANSHO Co., Ltd.) was added at a final concentration of 0.04% by a method similar to that in Reference Experimental Example 2, and the above-mentioned capsule was suspended by gently stirring. Successively, the tube was subjected to static culture in a $CO_2$ incubator (5% $CO_2$) for 5 days.

PBS (25 mL) was added to a culture medium containing a collagen gel capsule, and the collagen gel capsule was sedimented by centrifugation at 400G for 5 min and the supernatant was removed. Again, PBS (25 mL) was added, the mixture was centrifuged, and the supernatant was removed to make the amount of the rest 5 mL. To this solution was added 1% (W/V) collagenase L (manufactured by Nitta Gelatin Inc., 20 μL), and the mixture was shaken at 37° C. for 2 hr. After confirming dissolution of the collagen gel, PBS (10 mL) was added, and the cells were sedimented by centrifugation at 400G for 5 min and the supernatant was removed. To the cells was added 1 mL of trypsin-EDTA (ethylenediaminetetraacetic acid) solution (manufactured by WAKO), and the mixture was incubated at 37° C. for 5 min. To the obtained cell suspension was added 4 mM of DMEM medium containing 10% (v/v) fetal bovine serum, and the cells were sedimented by centrifugation at 400G for 5 min and the supernatant was removed. The obtained cells were suspended in 2 mL of the same medium above, and to a part thereof was added the same amount of Trypan Blue staining solution (manufactured by Invitrogen Corporation), and the number of the viable cells was measured by a hemocytometer (manufactured by ERMA INC.).

As a result, it was confirmed that, using the medium composition, collagen gel capsule embedded with HepG2 cells can be cultivated in a suspended state, and the cells efficiently proliferate in the medium composition. Furthermore, the medium composition was confirmed to show a cell proliferation promoting effect superior to that of the existing media without deacylated gellan gum.

Figure 11:
FIG. 11 is a Figure showing the suspended state of a collagen gel capsule in which HepG2 cells were embedded, when they were cultured in the medium composition.

The cell number of HepG2 cells when cultured in collagen gel capsule in a deacylated gellan gum-containing or -free medium for 5 days is shown in Table 33. In addition, the suspended state when the HepG2 cell-embedded collagen gel capsule was cultured in the medium composition is shown in FIG. 11.

TABLE 33

| deacylated gellan gum | HepG2 cell number (×10000/mL) |
| --- | --- |
| absent | 62.4 |
| present | 106.0 |

Reference Experimental Example 28: Sphere Recovery Test Using Filter

A DMEM medium (manufactured by WAKO) composition containing 0.015% deacylated gellan gum (KELCOGEL CG-LA, manufactured by SANSHO Co., Ltd.) and 10% (v/v) fetal bovine serum was prepared by a method similar to that in Reference Experimental Example 2. In addition, as a control, the same medium free of deacylated gellan gum was prepared. HepG2 cell spheres were formed by a method similar to that in Reference Experimental Example 2, and added to the medium (1 mL) prepared above by 86000 cells, the mixture was stood at 37° C. for 1 hr, and the sphere cell suspension was visually observed. Furthermore, the cell suspension was added onto Cell Strainers (manufactured by Becton, Dickinson and Company) having a mesh size of 40 μm to trap the spheres on the filter. Successively, PBS (10 mL) was flowed from the backside of the filter to recover the spheres in a 15 mL tube, the spheres were sedimented by centrifugation at 300G for 5 min. The supernatant was removed, 500 μm, of trypsin-EDTA (ethylenediaminetetraacetic acid) solution (manufactured by WAKO) was added to the spheres, and the mixture was incubated at 37° C. for 5 min. To the obtained cell suspension was added a DMEM medium (1 mL) containing 10% (v/v) fetal bovine serum, to a part thereof was added the same amount of Trypan Blue staining solution (manufactured by Invitrogen Corporation), and the number of viable cells was measured by a hemocytometer (manufactured by ERMA INC.). As a result, the sphere of HepG2 cells was confirmed to maintain a suspended state in the above-mentioned medium composition. Furthermore, it was confirmed that the cells of HepG2 cell sphere can be recovered at a recovery rate equivalent to that of a medium free of deacylated gellan gum by a filter treatment of a sphere suspension containing 0.015% deacylated gellan gum. The relative number recovered from the medium containing deacylated gellan gum is shown in Table 34, wherein the number of the HepG2 cells recovered with a filter and using a medium free of deacylated gellan gum is 1.

TABLE 34

| deacylated gellan gum | relative HepG2 cell number |
| --- | --- |
| absent | 1.0 |
| present | 1.1 |

Reference Experimental Example 29: Cell Suspension Test of Sphere Using Combination Agent of Various Polysaccharides A DMEM/F-12 medium composition containing a combination of xanthan gum (KELTROL CG, manufactured by SANSHO Co., Ltd.), sodium alginate (Duck alginic acid NSPM, manufactured by FOOD CHEMIFA Co., Ltd.), locust bean gum (GENUGUM RL-200-J, manufactured by SANSHO Co., Ltd.), methylcellulose (cP400, manufactured by WAKO), K-carageenan (GENUGEL WR-80-J, manufactured by SANSHO Co., Ltd.), pectin (GENU pectin LM-102AS, manufactured by SANSHO Co., Ltd.) or diutan gum (KELCO CRETE DG-F, manufactured by SANSHO Co., Ltd.), and deacylated gellan gum (KELCOGEL CG-LA, manufactured by SANSHO Co., Ltd.) was prepared by a method similar to that in Reference Experimental Example 9. In the same manner as in Reference Experimental Example 2, spheres of HepG2 cells were produced, and several tens of spheres were added to each medium (1 mL) prepared above, the mixture was stood still at 37° C. for 1 hr or one night, and the suspended state of the sphere cells was visually observed. As a result, it was confirmed that the spheres of HepG2 cells maintained the suspended state in any of the above-mentioned medium compositions. Furthermore, it was confirmed in all medium compositions that addition of a 2-fold amount of the medium and centrifugation (500G, for 5 min) of the cell suspension result in sedimentation and recovery of the spheres of HepG2 cells. The dispersion state of the sphere after one night was confirmed by visual observation, wherein a suspended and dispersed state is ○, partial sedimentation/dispersed state is Δ, and sedimented state is x. The evaluation results are shown in Table 35 and Table 36. In the Table, - shows not performed.

TABLE 35

| deacylated gellan gum concentration (%) | saccharides addition concentration (%) | methylcellulose | diutan gum |
| --- | --- | --- | --- |
| 0.005 | 0.05 | — | Δ |
|  | 0.2 | Δ | — |

TABLE 36

| deacylated gellan gum concentration (%) | saccharides addition concentration (%) | xanthan gum | sodium alginate | locust bean gum | methyl-cellulose | κ-cara-geenan | pectin | diutan gum |
| --- | --- | --- | --- | --- | --- | --- | --- | --- |
| 0.01 | 0.05 | — | — | — | — | ○ | — | ○ |
|  | 0.1 | ○ | ○ | ○ | — | — | Δ | — |
|  | 0.2 | — | — | — | ○ | — | — | — |

Comparison of Dispersibility of Beads and Cells-1

The dispersion state of dextran bead Cytodex (registered trade mark) 1 (manufactured by GE Healthcare Life Sciences) and HeLa cell sphere was compared between deacylated gellan gum containing medium prepared above (Comparative Example) and a methylcellulose-containing medium. The results are shown in Tables (Tables 37 and 38). Since the dispersion states of Cytodex1 and HeLa cell sphere correlate well, Cytodex1 can be used as a cell sphere model.

TABLE 37

| deacylgellan gum concentration % (w/v) | Cytodex1 suspension/ sedimentation | HeLa cell suspension/ sedimentation |
|---|---|---|
| 0.01 | suspension/partial sedimentation | suspension |
| 0.02 | suspension | suspension |
| 0.03 | suspension | suspension |
| 0.05 | suspension | suspension |

TABLE 38

| Methylcellulose % (w/v) | Cytodex1 suspension/ sedimentation | HeLa cell suspension/ sedimentation |
|---|---|---|
| 0.1 | sedimentation | sedimentation |
| 0.3 | sedimentation | sedimentation |
| 0.6 | sedimentation | sedimentation |
| 1.0 | sedimentation | sedimentation |

Comparison of Dispersibility of Beads and Cells-2

The dispersion state of polystyrene bead (Size 500-600 μm, manufactured by Polysciences Inc.) and HepG2 cell sphere was compared between the polysaccharide prepared in Reference Experimental Example 9 and deacylated gellan gum-containing medium. A suspended and dispersed state is ○, partial sedimentation/dispersed state is Δ, and sedimented state is x in the evaluation. The results are shown in Table (Table 39). Since the dispersion states of polystyrene bead and HepG2 cell sphere correlate well, polystyrene bead can be used as a cell sphere model.

TABLE 39

| | | xanthan gum | | alginic acid Na | | locust bean gum | | diutan gum | |
|---|---|---|---|---|---|---|---|---|---|
| | polysaccharide concentration | PS bead | HepG2 mass | PS bead | HepG2 mass | PS bead | HepG2 mass | PS bead | HepG2 mass |
| deacylated gellan gum concentration 0.01%(w/v) | 0.05% | | | | | | | ○ | ○ |
| | 0.1% | ○ | ○ | ○ | ○ | ○ | ○ | ○ | |
| | 0.2% | ○ | | ○ | | ○ | | | |

Reference Experimental Example 30: Suspension Culture Test of Rice-Derived Plant Callus Fifty seeds of a fully ripe seed of rice *Nipponbare* selected with a salt solution (purchased from Koto agricultural cooperatives) were transferred to a 50 mL polystyrene tube (manufactured by BD Falcon), washed with sterilized water (50 mL), and stirred in 70% ethanol water (30 mL) for 1 min. Ethanol water was removed, Kitchen Haiter (manufactured by Kao Corporation, 30 mL) was added, and the mixture was stirred for 1 hr. Kitchen Haiter was removed, and washed 4 times with sterilized water (50 mL). The sterilized seeds were cultured on Murashige Skoog basal medium (M9274, manufactured by Sigma Aldrich) containing 2 μg/mL 2,4-dichlorophenoxyacetic acid (manufactured by Sigma Aldrich) and agar at 1.5 mL/well (24 well flat bottom microplate (manufactured by Corning Incorporated)). They were cultured under the conditions of 30° C., for 16 hr dark place/for 8 hr dark place for 3 weeks, and cream-colored calluses (1-2 mm) grown on the seed blastocyst were harvested.

Figure 12:
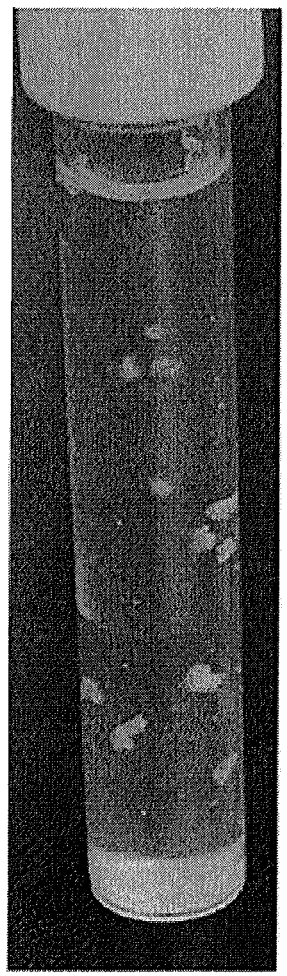
FIG. 12 is a Figure showing the suspended state of rice-derived callus when cultured in the medium composition.

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, a medium composition was prepared by adding deacylated gellan gum at a final concentration of 0.03% (w/v) to Murashige Skoog basal medium (M9274, manufactured by Sigma Aldrich) containing 2 μg/mL dichlorophenoxyacetic acid (manufactured by Sigma Aldrich). 15 calluses prepared above were added to this medium composition in a 10 mL/flat bottom tube (manufactured by BM Equipment Co., Ltd.), and cultured with shaking at 25° C. for 7 days. As a result, it was confirmed that, using the medium composition, rice-derived callus can be cultivated in a suspended state, and the calluses are maintained in the medium composition. The suspended state is shown in FIG. 12 when the rice-derived callus was cultured in the medium composition.

Production Example 1: Production of Cellulose Nanofiber Derived from Crystalline Cellulose Commercially available crystalline cellulose (PH-101 manufactured by Asahi Kasei Chemicals Corporation) (4 parts by mass) was dispersed in pure water (396 parts by mass), and a pulverization treatment was performed 100 times at 220 MPa by using a high-pressure pulverization device manufactured by Sugino Machine Limited (Star Burstsystem) to give a water dispersion of cellulose nanofiber derived from crystalline cellulose (MNC). The obtained dispersion was measured off in a petri dish, and dried at 110° C. for 1 hr to remove water. The amount of the residue was measured and the concentration was measured. As a result, the concentration of cellulose in water (solid content concentration) was 1.0 mass %. This water dispersion was sterilized by treating in an autoclave at 121° C. for 20 min.

Production Example 2: Production of Cellulose Nanofiber Derived from Pulp

Commercially available kraft pulp (LBKP manufactured by Oji F-Tex Co., Ltd., solid content 89 mass %) (5 parts by mass) was dispersed in pure water (145 parts by mass), and a pulverization treatment was performed 9 times at 1500 rpm by using a stone mill-grinder (Masscolloider) manufactured by MASUKO SANGYO CO., LTD. to give a pulp slurry. The aforementioned pulp slurry was treated 300 times at 220 MPa by using a high-pressure pulverization device (Star Burstsystem) manufactured by Sugino Machine Limited to give a water dispersion of nanocellulose (PNC). The obtained dispersion was measured off in a petri dish, and dried at 110° C. for 1 hr to remove water. The amount of the residue was measured and the concentration was measured. As a result, the concentration of cellulose (solid content concentration) in water was 1.6 mass %. This water dispersion was sterilized by treating in an autoclave at 121° C. for 20 min.

Production Example 3: Production of Chitin Nanofiber

Commercially available chitin powder (manufactured by KOYO CHEMICAL CO., LTD.) (20 parts by mass) was dispersed in pure water (980 parts by mass), and a pulverization treatment was performed 200 times at 245 MPa by using a high-pressure pulverization device (Star Burstsystem) manufactured by Sugino Machine Limited to give a water dispersion of chitin nanofiber (CT). The obtained dispersion was measured off in a petri dish, and dried at 110° C. for 1 hr to remove water. The amount of the residue was measured and the concentration was measured. As a result, the concentration of chitin (solid content concentration) in water was 2.0 mass %. This water dispersion was sterilized by treating in an autoclave at 121° C. for 20 min.

Experimental Example 1: Measurement of Average Fiber Diameter D and Average Fiber Length L The average fiber diameter (D) of nanofiber was determined as follows. A collodion support film manufactured by Okenshoji Co., Ltd. was subjected to a hydrophilizing treatment for 3 min by an ion creaner (JIC-410) manufactured by JEOL Ltd. Several drops of the nanofiber dispersion (diluted with ultrapure water) produced in Production Examples 1-3 were added dropwise, and dried at room temperature. This was observed under a transmission electron microscope (TEM, H-8000) (10,000-fold) manufactured by Hitachi, Ltd. at an accelerating voltage 200 kV. Using the obtained image, the fiber diameter of each one of the nanofibers (specimen number: 200-250) was measured, and the mean thereof was taken as the average fiber diameter (D).

As for the average fiber length (L), a nanofiber dispersion produced in the Production Example was diluted to 100 ppm with pure water, and nanofibers were uniformly dispersed using an ultrasonic cleaner. The nanofiber dispersion was cast on a silicon wafer subjected in advance to a hydrophilizing treatment of the surface with concentrated sulfuric acid, dried at 110° C. for 1 hr and used as a sample. Using an image obtained by observing the obtained sample under a scanning electron microscope (SEM, JSM-7400F) (2,000-fold), the fiber length of each one of the nanofibers (specimen number: 150-250) was measured, and the mean thereof was taken as the average fiber length (L).

The average fiber diameter D and average fiber length L of the nanofibers obtained in Production Examples 1 to Production Example 3 were determined, and the aspect ratio L/D was determined from these values. The obtained results are shown in Table 40.

TABLE 40

| | average fiber diameter D [nm] | average fiber length L [nm] | aspect ratio L/D |
|---|---|---|---|
| Production Example 1 (MNC) | 15 | 181 | 12 |
| Production Example 2 (PNC) | 13 | 2810 | 222 |
| Production Example 3 (CT) | 12 | 352 | 29 |

Examples 1 to Example 4

Using the nanofiber dispersions prepared in the aforementioned Production Examples 1 to Production Example 3 and aqueous deacylated gellan gum solutions, the medium compositions described in the following Table 41 were prepared.

To cellulose nanofiber MNC, PNC and chitin nanofiber prepared in Production Examples 1 to Production Example 3 was added sterile water to dilute each into 1% (w/v) water dispersion. On the other hand, to deacylated gellan gum (KELCOGEL CG-LA, manufactured by SANSHO Co., Ltd.: DAG) (1 part by mass) was added 99 parts by volume of sterile water, and the mixture was dissolved and sterilized by an autoclave treatment at 121° C. for 20 min to give 1% (w/v) aqueous deacylated gellan gum solution.

The aforementioned 1% (w/v) dispersion or aqueous solution (1 part by volume) was taken in a 50 mL conical tube, 49 parts by volume of sterile water was added, and the mixture was pipetted until it became uniform. Thereto was added 50 parts by volume of a 2-fold concentration of DMEM (high glucose, manufactured by Aldrich, containing given amount of sodium hydrogen carbonate) after sterilized by filtration with 0.22 μm filter, and mixed by pipetting to prepare a medium composition with a nanofiber concentration of 0.01% (w/v).

Similarly, medium compositions added with a nanofiber dispersion or aqueous deacylated gellan gum solution to a final desired concentration of 0.01-0.1% (w/v) were prepared.

Example 5 and Comparative Example 2 to Comparative Example 5

To κ-carageenan (GENUGEL WR-80-J, manufactured by SANSHO Co., Ltd.: Car) (Example 5), locust bean gum (GENUGUM RL-200-J, manufactured by SANSHO Co., Ltd.: LBG) (Comparative Example 2), xanthan gum (KELTROL CG, manufactured by SANSHO Co., Ltd.: Xan) (Comparative Example 3), diutan gum (KELCO CRETE DG-F, manufactured by SANSHO Co., Ltd.: DU) (Comparative Example 4), alginic acid Na (Duc alginic acid NSPM, manufactured by Food Chemifa Co., Ltd.: Alg) (Comparative Example 5) (1 part by mass) was added 99 parts by mass of sterile water, and dissolved and sterilized by an autoclave treatment at 121° C. for 20 min.

The polysaccharide solutions prepared as mentioned above were subjected to an operation similar to that in Examples 1 to 4 to prepare medium compositions added with a polysaccharide solution at a final concentration of 0.03, 0.05, 0.07, 0.1% (w/v).

Experimental Example 2: Evaluation of Suspending Action-1

To the medium compositions of Examples 1-5 and Comparative Examples 2-5 were added polystyrene beads (manufactured by Polysciences Inc., 200-300 μm) and, after confirmation of uniform dispersion of the beads in the medium composition by vortex stirring, the compositions were stood at room temperature (25° C.) for one day, and the dispersion state of the beads was confirmed by visual observation. They were evaluated with uniformly suspended state of beads in the medium composition as ⊙, partial development of supernatant as ○, and sedimentation state as x. The results are shown in Table 41.

As a result, the medium compositions of Example 1 to Example 4 showed a bead-suspending action. While Example 5 showed a bead-suspending action at room temperature, the beads were sedimented by heating to 37° C., and a suspending action was not obtained under cell culture conditions. In Comparative Example 2 to Comparative Example 5, the beads were completely sedimented on the bottom surface.

TABLE 41

| | | | concentration %(w/v) | | | | |
|---|---|---|---|---|---|---|---|
| | | | 0.01 | 0.03 | 0.05 | 0.07 | 0.1 |
| Example | 1 | MNC | X | X | ○ | ○ | ○ |
| | 2 | PNC | ○ | ⊙ | ⊙ | ⊙ | ⊙ |
| | 3 | CT | X | ○ | ○ | ○ | ○ |
| | 4 | DAG | ⊙ | ⊙ | ⊙ | ⊙ | ⊙ |
| | 5 | Car | X | ○* | ○* | ○* | ○* |
| Comparative Example | 2 | LBG | X | X | X | X | X |
| | 3 | Xan | X | X | X | X | X |
| | 4 | DU | X | X | X | X | X |
| | 5 | Alg | X | X | X | X | X |

*While κ-carageenan (Car) of Example 5 showed a suspending action at 25° C., the suspending action was instantaneously lost at 37° C. equivalent to cell culture conditions and the beads were sedimented. The same results were obtained in other media at 37° C. and 25° C.

Experimental Example 3: Evaluation of Suspending Action-2

In the same manner as in Experimental Example 2, the medium compositions of Examples 2, 4 and 5 and Comparative Example 2 were detailedly evaluated for suspending action in a low concentration region (0.01-0.04% (w/v)). Polystyrene beads were added and the compositions were stood for 2 days, and the dispersion state of the beads was confirmed by visual observation. They were evaluated with suspended and dispersed state as ⊙ and sedimentation state as x. As for partial sedimentation/dispersion state, the bead suspension rate was calculated based on the height of the suspension region in a 10 mL conical tube. The results are shown in Table 42.

TABLE 42

| | | | concentration %(w/v) | | | | | |
|---|---|---|---|---|---|---|---|---|
| | | polymer | 0.015 | 0.02 | 0.025 | 0.03 | 0.035 | 0.04 |
| Example | 2 | PNC | 50* | 65* | 85* | 90* | ○ | ○ |
| | 4 | DAG | ○ | ○ | ○ | ○ | ○ | ○ |
| | 5 | Car | X | X* | X* | X* | X* | X* |
| Comparative Example | 2 | LBG | X | X | X | X | X | X |

*shows a bead suspension rate. PNC showed a suspending action at a concentration of not less than 0.015% (w/v), and the medium composition of Example 4 showed a suspending action at not less than 0.015% (w/v). The medium composition of Example 2 showed a suspending action that was improved in stages along with increasing concentrations. While the medium composition of Example 5 showed a suspending action at 25° C. at not less than 0.02%, the suspending action was instantaneously lost at 37° C. and the beads were sedimented(*). The same results were obtained in other media at 37° C. and 25° C.

Experimental Example 4: Viscosity of Medium Composition

The viscosity of the medium compositions of Examples 1-5 and Comparative Examples 2-5 was evaluated under 25° C. condition and using a tuning fork vibration type viscometer (SV-1A, A&D Company Ltd.). The results are shown in FIG. 13. The obtained results indicate that the medium composition of the present invention having an extremely small content of nanofiber or polysaccharide thickener does not show a remarkable increase in the viscosity as compared to the viscosity of general medium. A comparison with the results of Experimental Example 2 showed no correlation between viscosity and the suspending action.

Experimental Example 5: Scanning Electron Microscopic Observation of Medium Composition The medium compositions prepared in Examples 1 to 5, Comparative Examples 3 to 4 were cast on a silicon wafer subjected in advance to a hydrophilizing treatment of the surface with concentrated sulfuric acid, dried at 110° C. (room temperature in Comparative Example 1 alone) for 1 hr. Pure water was poured thereon to remove extra salt content and the like, and the compositions were dried again at 110° C. for 1 hr and used as a sample. The aforementioned samples were observed under a scanning electron microscope manufactured by JEOL Ltd. (SEM, JSM-7400F) (10, 000-fold). The observation results of the medium compositions of Examples 1 to 4 and Comparative Examples 3 and 4 are shown in FIGS. 14 to 21.

As a result of the observation, Examples 1 to 4 and Example 5 dried at room temperature showed many fibers, whereas Example 5 dried at 110° C. and Comparative Example 3 to 4 did not show any fiber. Many spherical matters observed in the observation images are precipitated salt components in the medium. The results suggest that a fiber structure contained in the medium composition may contribute to the suspending action.

Experimental Example 7: Sphere-Suspending Action

Human liver cancer cell line HepG2 (manufactured by DS PHARMA BIOMEDICAL CO., LTD.) was suspended in DMEM medium containing 10% (v/v) fetal bovine serum (manufactured by WAKO) at 50000 cells/mL, and the aforementioned suspension (10 mL) was plated on EZ SPHERE (manufactured by ASAHI GLASS CO., LTD.) and cultured for 2 days in a $CO_2$ incubator (5% $CO_2$). A suspension (80 mL) of the sphere obtained here was subjected to a centrifugation treatment (800 rpm, 5 min.) to sediment spheres, and the supernatant was removed to give a sphere suspension (4.5 mL). Successively, the medium compositions of Examples 1 to 4 and Comparative Example 1, Comparative Examples 3 to 5 were placed in a 15 mL conical tube by 10 mL each, and a sphere suspension (100 μL) of HepG2 cells was further added. The spheres were dispersed by pipetting, incubated at 37° C. for 5 days, and the dispersion state of the spheres in the medium compositions was visually observed. They were evaluated with uniformly suspended state of sphere in the medium composition as ⊙, development of supernatant as ○, and sedimentation state as x. The observation results of the medium compositions of Examples 1 to 5, Comparative Examples 3 to 5 are shown in Table 43 and FIGS. 22 to 29.

As a result, a suspended state was found in the medium compositions of Example 1 to Example 4 even after 6 days of culture. On the other hand, all spheres were sedimented and the spheres were aggregated with each other in the medium compositions of Example 5 and Comparative Example 3 to Comparative Example 5.

TABLE 43

| | | polymer | concentration %(w/v) | | | | |
|---|---|---|---|---|---|---|---|
| | | | 0.01 | 0.03 | 0.05 | 0.07 | 0.1 |
| Example | 1 | MNC | X | ○ | ○ | ○ | ○ |
| | 2 | PNC | ○ | ○ | ○ | ○ | ○ |
| | 3 | CT | X | ○ | ○ | ○ | ○ |
| | 4 | DAG | ○ | ⊙ | ⊙ | ⊙ | ⊙ |
| | 5 | Car | X | X | X | X | X |
| Comparative Example | 3 | Xan | X | X | X | X | X |
| | 4 | DU | X | X | X | X | X |
| | 5 | Alg | X | X | X | X | X |

Example 1' to Example 4'

Sterile water was added to the cellulose nanofibers MNC, PNC and chitin nanofiber prepared in Production Examples 1 to Production Example 3 to prepare each 1% (w/v) water dispersion. On the other hand, to deacylated gellan gum (KELCOGEL CG-LA, manufactured by SANSHO Co., Ltd.: DAG) (1 part by mass) was added 99 parts by volume of sterile water, and the mixture was dissolved and sterilized by an autoclave treatment at 121° C. for 20 min to give 1% (w/v) aqueous solution. The 1% (w/v) fiber dispersion or aqueous deacylated gellan gum solution prepared above was added to DMEM medium containing 10% (v/v) fetal bovine serum (manufactured by NISSUI PHARMACEUTICAL CO., LTD., high-glucose) to a final concentration of 0.01%, 0.03%, 0.06% and 0.1% (w/v) to give medium compositions.

Example 5', and Comparative Example 3' to Comparative Example 5'

To κ-carageenan (GENUGEL WR-80-J, manufactured by SANSHO Co., Ltd.: Car), xanthan gum (KELTROL CG, manufactured by SANSHO Co., Ltd.: Xan), diutan gum (KELCO CRETE DG-F, manufactured by SANSHO Co., Ltd.: DU), alginic acid Na (Duc alginic acid NSPM, manufactured by Food Chemifa Co., Ltd.: Alg) (1 part by mass) was added 99 parts by mass of sterile water, and the mixtures were dissolved and sterilized by an autoclave treatment at 121° C. for 20 min to give each 1% (w/v) aqueous polysaccharide solution. The respective aqueous polysaccharide solutions prepared as mentioned above were subjected to an operation similar to that in Examples 5 to 8 to prepare medium compositions by adding an aqueous polysaccharide solution at a final concentration of 0.01%, 0.03%, 0.06% and 0.1% (w/v) to DMEM medium containing 10% (v/v) fetal bovine serum (manufactured by NISSUI PHARMACEUTICAL CO., LTD.).

Experimental Example 8: Cell Proliferation Test

Human breast cancer cell line MCF-7 (manufactured by DS PHARMA BIOMEDICAL CO., LTD.) and human melanoma cell line A375 (manufactured by ATCC) were seeded in the medium compositions prepared in Example 1' to Example 5' and Comparative Example 3' to Comparative Example 5' at 33333 cells/mL and dispensed to the wells of a 96 well flat bottom Ultra-Low Attachment Surface microplate (manufactured by Corning Incorporated, #3474) at 150 µL per well. As a negative control, MCF7 cells or A375 cells were suspended in the above media free of nanofiber or polysaccharide and the suspension was dispensed. Successively, the plate was cultured by being stood still in a $CO_2$ incubator (37° C., 5% $CO_2$) for 6 days at maximum. ATP reagent 150 (CellTiter-Glo™ Luminescent Cell Viability Assay, manufactured by Promega) was added and suspended in the culture medium after culture for 2 days and 6 days, and the medium was stood for about 10 min at room temperature. The luminescence intensity (RLU value) was measured by FlexStation3 (manufactured by Molecular Devices), and the luminescence of the medium alone was subtracted, whereby the viable cell number was measured.

As a result, it was confirmed that cells could be cultured in a uniformly dispersed state in the medium compositions containing PNC, MNC, or nanochitin, without developing an excessive size of cell aggregation mass, and efficient proliferation could be achieved. On the other hand, the medium composition containing sodium alginate did not show promotion of proliferation. The RLU values (ATP measurement, luminescence intensity) after standing culture of MCF7 cells for 2 days and 6 days are shown in Table 44 to Table 47, RLU values after 6 days are shown in FIG. 30 to FIG. 33, the results of A375 cells are shown in Table 48 to Table 51, and RLU values after 6 days are shown in FIG. 34 to FIG. 37. As for microscopic observation of aggregation mass after 2 days of culture, the results of MCF7 cells are shown in FIG. 38, and the results of A375 cells are shown in FIG. 39.

TABLE 44

| MCF7 | days of culture | polymer concentration %(w/v) | | | | |
|---|---|---|---|---|---|---|
| | | 0 | 0.01 | 0.03 | 0.06 | 0.1 |
| Example 1' | 2 | 9192 | 14688 | 15735 | 17096 | 17114 |
| | 6 | 7134 | 18829 | 21113 | 22987 | 22863 |
| Comparative Example 5' | 2 | 9192 | 10795 | 11016 | 11027 | 11947 |
| | 6 | 7134 | 9052 | 8727 | 7751 | 10444 |

TABLE 45

| MCF7 | days of culture | polymer concentration %(w/v) | | | | |
|---|---|---|---|---|---|---|
| | | 0 | 0.01 | 0.03 | 0.06 | 0.1 |
| Example 2' | 2 | 8324 | 14836 | 16139 | 15188 | 15292 |
| | 6 | 7213 | 21391 | 20795 | 19498 | 19912 |
| Example 3' | 2 | 8324 | 13563 | 14601 | 14760 | 15125 |
| | 6 | 7213 | 19340 | 19997 | 20439 | 21883 |

TABLE 46

| MCF7 | days of culture | polymer concentration %(w/v) | | | | |
|---|---|---|---|---|---|---|
| | | 0 | 0.01 | 0.03 | 0.06 | 0.1 |
| Example 4' | 2 | 10137 | 12454 | 13639 | 13424 | 9490 |
| | 6 | 9221 | 16246 | 18949 | 20341 | 15391 |
| Example 5' | 2 | 10137 | 10018 | 10714 | 11446 | 11888 |
| | 6 | 9221 | 5175 | 9414 | 9271 | 9191 |

TABLE 47

| MCF7 | days of culture | polymer concentration %(w/v) | | | | |
|---|---|---|---|---|---|---|
| | | 0 | 0.01 | 0.03 | 0.06 | 0.1 |
| Comparative Example 3' | 2 | 9915 | 11163 | 12016 | 11867 | 11501 |
| | 6 | 9201 | 10180 | 11686 | 12727 | 13678 |
| Comparative Example 4' | 2 | 9915 | 13354 | 13490 | 15527 | 15857 |
| | 6 | 9201 | 19364 | 19965 | 20615 | 21895 |

TABLE 48

| A375 | days of culture | polymer concentration %(w/v) | | | | |
|---|---|---|---|---|---|---|
| | | 0 | 0.01 | 0.03 | 0.06 | 0.1 |
| Example 1' | 2 | 31487 | 38387 | 39421 | 39260 | 39514 |
| | 6 | 49234 | 110943 | 113026 | 119850 | 125918 |
| Comparative Example 5' | 2 | 31487 | 30733 | 29778 | 29299 | 32224 |
| | 6 | 49234 | 46701 | 42424 | 43863 | 52514 |

TABLE 49

| A375 | days of culture | polymer concentration %(w/v) | | | | |
|---|---|---|---|---|---|---|
| | | 0 | 0.01 | 0.03 | 0.06 | 0.1 |
| Example 2' | 2 | 30087 | 35275 | 35385 | 35648 | 35637 |
| | 6 | 50280 | 111250 | 130356 | 146403 | 153298 |
| Example 3' | 2 | 30087 | 36297 | 38784 | 37907 | 37408 |
| | 6 | 50280 | 112508 | 111581 | 123872 | 132729 |

TABLE 50

| A375 | days of culture | polymer concentration %(w/v) | | | | |
|---|---|---|---|---|---|---|
| | | 0 | 0.01 | 0.03 | 0.06 | 0.1 |
| Example 4' | 2 | 32553 | 41656 | 41349 | 43184 | 41347 |
| | 6 | 43620 | 81160 | 80734 | 103404 | 122478 |
| Example 5' | 2 | 32553 | 28039 | 29995 | 31168 | 30212 |
| | 6 | 43620 | 33578 | 31297 | 40548 | 36972 |

TABLE 51

| A375 | days of culture | polymer concentration %(w/v) | | | | |
|---|---|---|---|---|---|---|
| | | 0 | 0.01 | 0.03 | 0.06 | 0.1 |
| Comparative Example 3' | 2 | 29361 | 30417 | 28822 | 25348 | 23952 |
| | 6 | 38820 | 37202 | 38083 | 38340 | 38566 |
| Comparative Example 4' | 2 | 29361 | 34219 | 29473 | 34592 | 35261 |
| | 6 | 38820 | 54749 | 57507 | 68100 | 82009 |

Experimental Example 9: Preservation Test Using 3T3-L1 Cells

Mouse preadipocyte strain 313-L1 (manufactured by ATCC) was seeded in a 10% FBS-containing DMEM medium on a 10 cm polystyrene petri dish and cultured in an incubator set to 5% $CO_2$, 37° C. When 313-L1 cells became confluent, the medium was aspirated, FBS was removed by D-PBS (manufactured by Wako Pure Chemical Industries, Ltd.), and a solution (1 ml) containing 0.25% Trypsin and 1 m MEDIA (manufactured by Wako Pure Chemical Industries, Ltd.) was added to the above-mentioned polystyrene petri dish. After confirmation of cell detachment, 10% by volume FBS-containing DMEM medium was added and the cells were recovered from the petri dish and placed in a centrifugation tube. The cells were centrifuged at 300×g, and the supernatant was removed. A cell suspension of about $100×10^4$ cells/mL was prepared, 100 μL of the cell suspension was added into a 1.5 mL microtube, the medium compositions of Example 1 and Example 2, Example 4 and Example 5, Comparative Example 3 and Comparative Example 5 prepared in advance to contain 10% (v/v) FBS were added by 100 μL each and the mixture was pipetted to give cell suspensions.

The cell suspensions were preserved in a standing state in a tightly closed state at room temperature for 10 days and, after progress of 3 days or 10 days, a part thereof was 1/10 diluted with 10% FBS-containing DMEM medium. ATP reagent (100 μL)(Cellliter-Glo™ Luminescent Cell Viability Assay, manufactured by Promega) was added to the diluted cell suspension (100 μL) and suspended therein, and the medium was stood for 15 min at room temperature. The luminescence intensity (RLU value) was measured by Flex-Station3 (manufactured by Molecular Devices), and the luminescence of the medium alone was subtracted, whereby the viable cell number was measured. The negative control was a sample containing medium alone without polysaccharide.

As a result, as for each cell survival rate of the negative control or the medium compositions of Comparative Example 3 and Comparative Example 5, the ATP value remarkably decreased by preservation at room temperature for 3 to 10 days, and a decrease in the ATP value was suppressed in the medium compositions of Example 1 to Example 2 and Example 4, thus showing a cell protection effect. The results of viable cell number are shown in Table 52.

TABLE 52

| | polysaccharides | concentration | RLU value (viable cell number) | | |
|---|---|---|---|---|---|
| | | | day 0 | 3 days later | 10 days later |
| negative target | — | 0% | 106016 | 34965 | 13069 |
| Example 1 | MNC | 0.03% | — | 62627 | 36046 |
| Example 2 | PNC | 0.03% | — | 59723 | 32436 |
| Example 4 | DAG | 0.015% | — | 75493 | 49952 |
| Comparative Example 3 | Xan | 0.03% | — | 40667 | 13441 |
| Comparative Example 5 | Alg | 0.03% | — | 47068 | 8834 |

Experimental Example 10: Preservation Test Using CHO-K1 Cells

Chinese hamster ovary strain CHO-K1-hIFNβ cells (provided by Dr. Kawahara of Kitakyushu National College of Technology) were seeded in a 10% FBS-containing F12 medium on a 10 cm polystyrene petri dish and cultured in an incubator set to 5% $CO_2$, 37° C. When CHO-K1-hIFNβ cells became confluent, the medium was aspirated, FBS was removed by D-PBS (manufactured by Wako Pure Chemical Industries, Ltd.), and a solution (1 ml) containing 0.25% Trypsin and 1 m MEDTA (manufactured by Wako Pure Chemical Industries, Ltd.) was added to the above-mentioned polystyrene petri dish. After confirmation of cell detachment, 10% FBS-containing F12 medium was added and the cells were recovered from the petri dish and placed in a centrifugation tube. The cells were centrifuged at 300×g, and the supernatant was removed. A cell suspension of about $5×10^6$ cells/mL was prepared, 25 μL of the cell suspension was added into a 1.5 mL microtube, the medium compositions of Example 2 and Example 4 prepared in advance to contain 10% (v/v) FBS were added by 25 μL each and the mixture was pipetted to give cell suspensions.

The cell suspensions were preserved in a tightly closed state at room temperature for one day and a part thereof was 1/10 diluted with 10% FBS-containing F12 medium. ATP reagent (100 μL) (CellTiter-Glo™ Luminescent Cell Viability Assay, manufactured by Promega) was added to the diluted cell suspension (100 μL) and suspended therein, and the suspension was stood for about 10 min at room temperature, and the luminescence intensity (RLU value) was measured by FlexStation3 (manufactured by Molecular Devices), and the number of viable cells was measured by subtracting the luminescence value of the medium alone. The negative control was a sample containing medium alone without polysaccharide.

As a result, as for each cell survival rate in the negative control, the ATP value decreased by preservation at room temperature for one day; however, the medium compositions of Example 2 and Example 4 showed an ATP value of the level on seeding, thus showing a cell protection effect. The results of viable cell number are shown in Table 53.

TABLE 53

| | polysaccharides | concentration | day 0 | 1 day later |
|---|---|---|---|---|
| | | | RLU value (viable cell number) | |
| negative control | — | 0% | 109376 | 87031 |
| Example 2 | PNC | 0.1% | — | 108666 |
| Example 4 | DAG | 0.03% | — | 95028 |
| | | 0.1% | — | 111383 |

Experimental Example 11: Preservation Test Using 3T3-L1 Cells, Change of Polysaccharide Concentration Mouse preadipocyte strain 3T3-L1 (manufactured by ATCC) was seeded in a 10% FBS-containing DMEM medium on a 10 cm polystyrene petri dish and cultured in an incubator set to 5% $CO_2$, 37° C. When 3T3-L1 cells became 40% confluent, the medium was aspirated, FBS was removed by D-PBS (manufactured by Wako Pure Chemical Industries, Ltd.), and a solution (1 ml) containing 0.25% Trypsin and 1 mM EDTA (manufactured by Wako Pure Chemical Industries, Ltd.) was added to the above-mentioned polystyrene petri dish. After confirmation of cell detachment, 10% by volume FBS-containing DMEM medium was added and the cells were recovered from the petri dish and placed in a centrifugation tube. The cells were centrifuged at 300×g, and the supernatant was removed. A cell suspension of about $100 \times 10^4$ cells/mL was prepared, 100 μL, of the cell suspension was added into a 1.5 mL microtube, the medium compositions of Example 2 and Example 4, and Comparative Example 5 with different concentrations of polysaccharides and prepared in advance to contain 10% (v/v) FBS were added by 100 μL each and the mixture was pipetted to give cell suspensions.

The cell suspensions were preserved in a standing state in a tightly closed state at room temperature for 8 days and, after progress of 0 day, 5 days or 8 days, a part thereof was 1/3 diluted with 10% FBS-containing DMEM medium. ATP reagent (100 μL) (CellTiter-Glo™ Luminescent Cell Viability Assay, manufactured by Promega) was added to the diluted cell suspension (100 μL) and suspended therein, and the medium was stood for 15 min at room temperature. The luminescence intensity (RLU value) was measured by FlexStation3 (manufactured by Molecular Devices), and the luminescence of the medium alone was subtracted, whereby the viable cell number was measured. The negative control was a sample containing medium alone without polysaccharide.

As a result, as for each cell survival rate of the negative control or the medium composition of Comparative Example 3, the ATP value remarkably decreased by preservation at room temperature for 5 to 8 days, and a decrease in the ATP value was suppressed in the medium compositions of Example 2 and Example 4, thus showing a cell protection effect. The results of viable cell number are shown in Table 54.

TABLE 54

| | polysaccharides | | concentration % | day 0 | 5 days later | 8 days later |
|---|---|---|---|---|---|---|
| | | | | | RLU value (viable cell number) | |
| negative target | — | | 0 | 99550 | 38344 | 34158 |
| Example | 2 | PNC | 0.015 | — | 55431 | 57008 |
| | | | 0.03 | — | 76226 | 72182 |
| | | | 0.05 | — | 70520 | 47521 |
| | 4 | DAG | 0.015 | — | 67938 | 61719 |
| | | | 0.03 | — | 61126 | — |
| | | | 0.05 | — | 65334 | 55547 |
| Comparative Example | 5 | Alg | 0.015 | — | 35927 | 26641 |
| | | | 0.03 | — | 43659 | 40677 |
| | | | 0.05 | — | 49629 | 44898 |

Experimental Example 12: Effect on Cell Survival Action on MDCK Cells

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, medium compositions composed of EMEM medium containing 10% (v/v) fetal bovine serum (manufactured by Wako Pure Chemical Industries, Ltd.) added with deacylated gellan gum at a final concentration of 0.005% (w/v) or 0.015%, and a medium composition composed of EMEM medium containing 10% (v/v) fetal bovine serum free of deacylated gellan gum, were prepared. Successively, canine kidney renal tubule epithelial cell line MDCK (manufactured by DS PHARMA BIOMEDICAL CO., LTD.) cultured in a serum-free medium for one day (starvation treatment) was inoculated to the above-mentioned medium compositions added with deacylated gellan gum at 100000 cells/mL, and dispensed to the wells of a 96-well flat bottom ultra low adhesion surface microplate (manufactured by Corning Incorporated, #3474) at 100 μL/well. Each plate was cultured by being stood still in a $CO_2$ incubator (37° C., 5% $CO_2$) for 15 days. To the culture media after culturing for 2, 6, 9, 12 and 15 days was added an ATP reagent (100 μL) (CellTiter-Glo™ Luminescent Cell Viability Assay, manufactured by Promega) to give a suspension, which was stood for about 10 min at room temperature, and the luminescence intensity (RLU value) was measured by FlexStation3 (manufactured by Molecular Devices), and the number of viable cells was measured by subtracting the luminescence value of the medium alone.

As a result, it was clarified that a decrease in the viable cell number can be suppressed by culturing MDCK cells in the medium composition of the present invention on a low adhesion plate. The RLU value in each culture (ATP measurement, luminescence intensity) is shown in Table 55.

TABLE 55

| culture period (days) | no addition | deacylated gellan gum (0.005%) | deacylated gellan gum (0.015%) |
|---|---|---|---|
| 2 | 23453 | 25309 | 26069 |
| 6 | 15839 | 17643 | 26602 |
| 9 | 9939 | 14552 | 26668 |
| 12 | 9833 | 12409 | 26210 |
| 15 | 10374 | 13152 | 29512 |

Experimental Example 13: Effect on Cell Survival Action on Vero Cells

Deacylated gellan gum (KELCOGEL CG-LA, manufactured by SANSHO Co., Ltd.) was suspended in ultrapure water (Milli-Q water) to 0.3% (w/v), and dissolved by stirring with heating at 90° C. This aqueous solution was sterilized at 121° C. for 20 min in an autoclave. Using this solution, medium compositions composed of Emedium199 medium containing 5% (v/v) fetal bovine serum (manufactured by Sigma Ltd.) added with deacylated gellan gum at a final concentration of 0.005% (w/v) or 0.015%, and a no-addition medium composition free of deacylated gellan gum, were prepared. Successively, monkey kidney epithelial cell line Vero (manufactured by DS PHARMA BIOMEDICAL CO., LTD.) cultured in a serum-free medium for one day (starvation treatment) was inoculated to the above-mentioned medium composition added with deacylated gellan gum at 100000 cells/mL, and dispensed to the wells of a 96-well flat bottom ultra low adhesion surface microplate (manufactured by Corning Incorporated, #3474) at 100 μL/well. Each plate was cultured by being stood still in a $CO_2$ incubator (37° C., 5% $CO_2$) for 15 days. To the culture media after culturing for 2, 6, 9, 12 and 15 days was added an ATP reagent (100 μL) (CellTiter-Glo™ Luminescent Cell Viability Assay, manufactured by Promega) to give a suspension, which was stood for about for 10 min at room temperature, and the luminescence intensity (RLU value) was measured by FlexStation3 (manufactured by Molecular Devices), and the number of viable cells was measured by subtracting the luminescence value of the medium alone.

As a result, it was clarified that a decrease in the viable cell number can be suppressed by culturing Vero cells in the medium composition of the present invention on a low adhesion plate. The RLU value in each culture (ATP measurement, luminescence intensity) is shown in Table 56.

TABLE 56

| culture period (days) | no addition | deacylated gellan gum (0.005%) | deacylated gellan gum (0.015%) |
|---|---|---|---|
| 2 | 17518 | 17870 | 16940 |
| 6 | 12970 | 13298 | 13472 |
| 9 | 9500 | 12560 | 13097 |
| 12 | 8702 | 10039 | 14053 |
| 15 | 6934 | 9207 | 14910 |

Experimental Example 14: Effect of Each Substrate on MDCK Cell Proliferation Action Cellulose nanofiber (PNC) prepared in Production Example 2, chitin nanofiber (biomass nanofiber BiNFi-S 2 mass %, Sugino Machine Limited) and deacylated gellan gum (KELCOGEL CG-LA, manufactured by SANSHO Co., Ltd.) were suspended in ultrapure water (Milli-Q water) to 1% (w/v), and dissolved by stirring with heating at 90° C. This aqueous solution was sterilized at 121° C. for 20 min in an autoclave. A medium composition which is serum-free KBM220 medium (manufactured by KOHJIN BIO) added with cellulose nanofiber at a final concentration of 0.01% (w/v), 0.03%, or 0.1%, a medium composition which is serum-free KBM220 medium added with chitin nanofiber at a final concentration of 0.01% (w/v), 0.03%, or 0.1%, a medium composition which is serum-free KBM220 medium (manufactured by KOHJIN BIO) added with deacylated gellan gum at a final concentration of 0.005% (w/v), 0.015%, 0.03%, 0.06%, or 0.1%, and the above-mentioned no-addition medium composition free of any substrates were prepared. Successively, canine kidney renal tubule epithelial cell line MDCK (manufactured by DS PHARMA BIOMEDICAL CO., LTD.) cultured in a serum-free medium for one day (starvation treatment) was inoculated to the above-mentioned medium composition added with each substrate at 100000 cells/mL, and dispensed to the wells of a 96-well flat bottom ultra low adhesion surface microplate (manufactured by Corning Incorporated, #3474) at 100 μL/well. Each plate was cultured by being stood still in a $CO_2$ incubator (37° C., 5% $CO_2$) for 14 days. To the culture media after culturing for 3, 7, 10 and 14 days was added an ATP reagent (100 μL) (CellTiter-Glo™ Luminescent Cell Viability Assay, manufactured by Promega) to give a suspension, which was stood for about for 10 min at room temperature, and the luminescence intensity (RLU value) was measured by FlexStation3 (manufactured by Molecular Devices), and the number of viable cells was measured by subtracting the luminescence value of the medium alone.

As a result, when MDCK cells were cultured using deacylated gellan gum, nanocellulose fiber PNC, or chitin nanofiber, which is the medium composition of the present invention, on a low adhesion plate, a proliferation promoting action on MDCK cells was observed in all of the compositions with addition of each of the substrates. Of those, chitin nanofiber showed the strongest effect. The RLU value in each culture (ATP measurement, luminescence intensity) is shown in Table 57.

TABLE 57

|  | day 3 | day 7 | day 10 | day 14 |
|---|---|---|---|---|
| no addition | 6945 | 7388 | 7611 | 10225 |
| deacylated gellan gum 0.005% | 7389 | 9039 | 10981 | 16549 |
| deacylated gellan gum 0.015% | 7735 | 10467 | 14369 | 21255 |
| deacylated gellan gum 0.03% | 7943 | 21459 | 30706 | 38572 |
| deacylated gellan gum 0.06% | 7538 | 17257 | 31697 | 44346 |
| deacylated gellan gum 0.1% | 6696 | 15065 | 27092 | 35897 |

TABLE 57-continued

|  | day 3 | day 7 | day 10 | day 14 |
|---|---|---|---|---|
| nanocellulose PNC 0.01% | 7622 | 14815 | 22065 | 34661 |
| nanocellulose PNC 0.03% | 7795 | 17250 | 29732 | 44805 |
| nanocellulose PNC 0.1% | 7406 | 15408 | 27157 | 41852 |
| chitin nanofiber 0.01% | 8777 | 21536 | 42566 | 54671 |
| chitin nanofiber 0.03% | 8886 | 28311 | 44933 | 58338 |
| chitin nanofiber 0.1% | 8621 | 29025 | 45074 | 59755 |

Experimental Example 15: Effect of Chitin Nanofiber on MDCK Proliferation Action Cellulose nanofiber (PNC) prepared in Production Example 1, chitin nanofiber (biomass nanofiber BiNFi-S 2 mass %, Sugino Machine Limited) and deacylated gellan gum (KELCOGEL CG-LA, manufactured by SANSHO Co., Ltd.) were suspended in ultrapure water (Milli-Q water) to 1% (w/v), and dissolved by stirring with heating at 90° C. This aqueous solution was sterilized at 121° C. for 20 min in an autoclave. A medium composition which is serum-free KBM220 medium (manufactured by KOHJIN BIO) added with chitin nanofiber at a final concentration of 0.0001% (w/v), 0.0003%, 0.001%, 0.003%, 0.01%, 0.02%, or 0.03%, a medium composition which is serum-free KBM220 medium added with deacylated gellan gum at a final concentration of 0.005% (w/v), 0.015%, or 0.03%, and the above-mentioned no-addition medium composition free of a substrate were prepared. Successively, canine kidney renal tubule epithelial cell line MDCK (manufactured by DS PHARMA BIOMEDICAL CO., LTD.) cultured in a serum-free medium for one day (starvation treatment) was inoculated to the above-mentioned medium composition added with deacylated gellan gum or chitin nanofiber at 100000 cells/mL, and dispensed to the wells of a 96-well flat bottom ultra low adhesion surface microplate (manufactured by Corning Incorporated, #3474) at 100 μL/well. Each plate was cultured by being stood still in a $CO_2$ incubator (37° C., 5% $CO_2$) for 14 days. To the culture media after culturing for 5, 9, 12 and 15 days was added an ATP reagent (100 μL) (CellTiter-Glo™ Luminescent Cell Viability Assay, manufactured by Promega) to give a suspension, which was stood for about for 10 min at room temperature, and the luminescence intensity (RLU value) was measured by FlexStation3 (manufactured by Molecular Devices), and the number of viable cells was measured by subtracting the luminescence value of the medium alone and as a mean of 3 points.

As a result, when MDCK cells were cultured using deacylated gellan gum and chitin nanofiber, which are the medium compositions of the present invention, on a low adhesion plate, a proliferation promoting action on MDCK cells was observed in both of the compositions with each of substrates. Of those, chitin nanofiber showed a proliferation-promoting effect at a concentration of not less than 0.0001%, particularly not less than 0.001%. The RLU value in each culture (ATP measurement, luminescence intensity) is shown in Table 58.

TABLE 58

|  | day 5 | day 9 | day 12 | day 15 |
|---|---|---|---|---|
| no addition | 30616 | 22182 | 32644 | 27527 |
| deacylated gellan gum 0.005% | 36600 | 32749 | 49935 | 54224 |
| deacylated gellan gum 0.015% | 44682 | 54161 | 71837 | 85747 |
| deacylated gellan gum 0.03% | 35918 | 43907 | 55424 | 64556 |
| chitin nanofiber 0.0001% | 44955 | 42380 | 55915 | 55612 |
| chitin nanofiber 0.0003% | 61972 | 66269 | 75845 | 81075 |
| chitin nanofiber 0.001% | 72036 | 93296 | 114045 | 122244 |
| chitin nanofiber 0.003% | 78232 | 108468 | 140210 | 146761 |
| chitin nanofiber 0.01% | 74018 | 104834 | 148507 | 156114 |
| chitin nanofiber 0.02% | 84482 | 113526 | 160236 | 168680 |
| chitin nanofiber 0.03% | 84062 | 127656 | 174498 | 173008 |

Experimental Example 16: Effect of Chitin Nanofiber on MDCK Cell Proliferation Action Primary culture;
Cellulose nanofiber (PNC) prepared in Production Example 2, or chitin nanofiber (biomass nanofiber BiNFi-S 2 mass %, Sugino Machine Limited) was suspended in ultrapure water (Milli-Q water) to 1% (w/v), and dissolved by stirring with heating at 90° C. This aqueous solution was sterilized at 121° C. for 20 min in an autoclave. A medium composition which is serum-free KBM220 medium added with chitin nanofiber at a final concentration of 0.01% (w/v), and a no-addition medium composition which is serum-free KBM220 medium (manufactured by KOHJIN BIO) free of chitin nanofiber were prepared. Successively, canine kidney renal tubule epithelial cell line MDCK (manufactured by DS PHARMA BIOMEDICAL CO., LTD.) cultured in a serum-free medium for one day (starvation treatment) was inoculated to the above-mentioned medium composition added with the above-mentioned chitin nanofiber at 75000 cells/mL, and dispensed to a 125 ml Erlenmeyer flask (manufactured by Corning Incorporated, #431405) at 30 mL per flask. The flask was cultured by being stood still in a $CO_2$ incubator (37° C., 5% $CO_2$) for 6 days. The culture medium on day 0 and day 6 was suspended with a pipette, 100 μL was dispensed at 3 points and an ATP reagent (100 μL) (CellTiter-Glo™ Luminescent Cell Viability Assay, manufactured by Promega) was added to give a suspension, which was stood for about for 10 min at room temperature, and the luminescence intensity (RLU value) was measured by FlexStation3 (manufactured by Molecular Devices), and the number of viable cells was measured by subtracting the luminescence value of the medium alone.

Passage Culture;
To confirm the effect on passage culture, a cell suspension obtained by culturing MDCK cells in a medium containing 0.01% chitin nanofiber for 6 days was studied. A cell suspension obtained by mixing the cell suspension (3 ml) and a no-addition medium composition (27 ml) to a chitin nanofiber concentration of 0.001%, and a cell suspension having a chitin nanofiber concentration of 0.01% which was obtained by mixing the cell suspension (3 ml) and a medium composition (27 ml) added with chitin nanofiber at a final concentration of 0.01% (w/v) were each dispensed to a 125 ml Erlenmeyer flask (manufactured by Corning Incorporated, #431405) at 30 mL per flask. The flask was cultured by being stood still in a $CO_2$ incubator (37° C., 5% $CO_2$) for 14 days. The culture medium on day 0, day 7 and day 14 was suspended with a pipette, 100 μL was dispensed at 3 points each and an ATP reagent (100 μL) (CellTiter-Glo™ Luminescent Cell Viability Assay, manufactured by Promega) was added to give a suspension, which was stood for about for 10 min at room temperature, and the luminescence intensity (RLU value) was measured by FlexStation3 (manufactured by Molecular Devices), and the number of viable cells was measured by subtracting the luminescence value of the medium alone and as a mean of 3 points.

As a result, a MDCK cell proliferation-promoting action was observed by culturing MDCK cells in an Erlenmeyer flask by using chitin nanofiber which is the medium composition of the present invention. When a medium containing chitin nanofiber was added, the proliferation of MDCK cells was observed, and it was clarified that passage culture can be conveniently performed without a treatment with trypsin and the like. The RLU value (ATP measurement, luminescence intensity) in the primary culture is shown in Table 59, and the RLU value (ATP measurement, luminescence intensity) in the passage culture is shown in Table 60.

TABLE 59

|  | day 0 | day 6 |
| --- | --- | --- |
| chitin nanofiber 0.01% | 12853 | 28826 |

TABLE 60

|  | day 0 | day 7 | day 14 |
| --- | --- | --- | --- |
| chitin nanofiber 0.001% | 2428 | 11461 | 18641 |
| chitin nanofiber 0.01% | 2553 | 13981 | 34397 |

Experimental Example 17: Comparison of MDCK Cell Proliferation-Promoting Action of Chitin Nanofiber in Each Medium Cellulose nanofiber (PNC) prepared in Production Example 1, chitin nanofiber (biomass nanofiber BiNFi-S 2 mass %, Sugino Machine Limited) and deacylated gellan gum (KELCOGEL CG-LA, manufactured by SANSHO Co., Ltd.) were suspended in ultrapure water (Milli-Q water) to 1% (w/v), and dissolved by stirring with heating at 90° C. This aqueous solution was sterilized at 121° C. for 20 min in an autoclave. A medium composition which is serum-free KBM220 medium (manufactured by KOHJIN BIO) or Cosmedium 012 medium (manufactured by COSMO BIO co., Ltd.) added with chitin nanofiber at a final concentration of 0.001% (w/v), or 0.01%, a medium composition which is serum-free KBM220 medium or Cosmedium 012 medium added with deacylated gellan gum at a final concentration of 0.03%, and a no-addition medium composition free of the above-mentioned substrates were prepared. Successively, canine kidney renal tubule epithelial cell line MDCK (manufactured by DS PHARMA BIOMEDICAL CO., LTD.) cultured in a serum-free medium for one day (starvation treatment) was inoculated to the above-mentioned medium composition added with deacylated gellan gum or chitin nanofiber at 100000 cells/mL, and dispensed to the wells of a 96-well flat bottom ultra low adhesion surface microplate (manufactured by Corning Incorporated, #3474) at 100 μL/well. Each plate was cultured by being stood still in a $CO_2$ incubator (37° C., 5% $CO_2$) for 12 days. To the culture medium on day 4, day 8 and day 12 was added an ATP reagent (100 μL) (CellTiter-Glo™ Luminescent Cell Viability Assay, manufactured by Promega) to give a suspension, which was stood for about for 10 min at room temperature, and the luminescence intensity (RLU value) was measured by FlexStation3 (manufactured by Molecular Devices), and the number of viable cells was measured by subtracting the luminescence value of the medium alone and as a mean of 3 points.

As a result, a MDCK cell proliferation-promoting action by the addition of the both substrates of deacylated gellan gum and chitin nanofiber was observed by culturing MDCK cells on a low adhesion plate by using the deacylated gellan gum and chitin nanofiber which are the medium compositions of the present invention. Of these, chitin nanofiber showed high proliferative capacity even at a concentration of not less than 0.001% and using Cosmedium012 medium. The cell state on day 4 was observed under a microscope. As a result, cell aggregate mass (sphere) was merely dispersed in a medium condition using deacylated gellan gum, whereas spheres and cells were proliferated in cluster of grapes in a medium condition using chitin nanofiber. The RLU value (ATP measurement, luminescence intensity) in the culture using KBM220 medium is shown in Table 61, and the RLU value (ATP measurement, luminescence intensity) in the culture using Cosmedium012 medium is shown in Table 62. The results of microscopic observation of 4 days of culture are shown in FIG. 40.

TABLE 61

|  | day 4 | day 8 | day 12 |
| --- | --- | --- | --- |
| no addition | 23542 | 23441 | 30472 |
| deacylated gellan gum 0.015% | 28314 | 35649 | 57595 |
| deacylated gellan gum 0.03% | 27360 | 33025 | 53464 |
| chitin nanofiber 0.001% | 49998 | 63869 | 120492 |
| chitin nanofiber 0.01% | 55646 | 70073 | 131614 |

TABLE 62

|  | day 4 | day 8 | day 12 |
| --- | --- | --- | --- |
| no addition | 23373 | 23709 | 27167 |
| deacylated gellan gum 0.015% | 27412 | 29959 | 51690 |
| deacylated gellan gum 0.03% | 25382 | 27227 | 44496 |
| chitin nanofiber 0.001% | 45617 | 62417 | 102726 |
| chitin nanofiber 0.01% | 57318 | 69040 | 118593 |

Experimental Example 18: Comparison of MDCK Cell Proliferation Action of Chitosan Nanofiber and Chitin Nanofiber Chitosan nanofiber (biomass nanofiber BiNFi-S, 1 mass %, Sugino Machine Limited) and chitin nanofiber (biomass nanofiber BiNFi-S 2 mass %, Sugino Machine Limited) and an aqueous solution prepared in the same manner as in Reference Example 1 by suspending deacylated gellan gum (KELCOGEL CG-LA, manufactured by SANSHO Co., Ltd.) in ultrapure water (Milli-Q water) to 1% (w/v) and stirring same at 90° C. were each sterilized at 121° C. for 20 min in an autoclave. A medium composition which is serum-free KBM220 medium (manufactured by KOHJIN BIO) added with chitosan nanofiber or chitin nanofiber at a final concentration of 0.001% (w/v), 0.003%, 0.01%, or 0.03%, a medium composition which is serum-free KBM220 medium added with deacylated gellan gum at a final concentration of 0.03%, and a no-addition medium composition free of the above-mentioned substrates were prepared. Successively, canine kidney renal tubule epithelial cell line MDCK (manufactured by DS PHARMA BIO-MEDICAL CO., LTD.) cultured in a serum-free medium for one day (starvation treatment) was inoculated to the above-mentioned medium composition added with deacylated gellan gum, chitosan nanofiber or chitin nanofiber at 100000 cells/mL, and dispensed to the wells of a 96-well flat bottom ultra low adhesion surface microplate (manufactured by Corning Incorporated, #3474) at 100 µL/well. Each plate was cultured by being stood still in a $CO_2$ incubator (37° C., 5% $CO_2$) for 12 days. To the culture medium on day 7 and day 11 was added an ATP reagent (100 µL) (CellTiter-Glo™ Luminescent Cell Viability Assay, manufactured by Promega) to give a suspension, which was stood for about for 10 min at room temperature, and the luminescence intensity (RLU value) was measured by FlexStation3 (manufactured by Molecular Devices), and the number of viable cells was measured by subtracting the luminescence value of the medium alone and as a mean of 3 points.

As a result, a proliferation promoting action higher than that of deacylated gellan gum was observed by culturing MDCK cells on a low adhesion plate by using chitosan nanofiber and chitin nanofiber which are the medium compositions of the present invention. In addition, chitin nanofiber showed high proliferative capacity even at 0.001% concentration, and chitosan nanofiber showed high proliferative capacity from 0.01% concentration. The RLU value (ATP measurement, luminescence intensity) is shown in Table 63.

TABLE 63

|  | day 7 | day 11 |
| --- | --- | --- |
| no addition | 30653 | 27078 |
| deacylated gellan gum 0.015% | 51436 | 63794 |
| deacylated gellan gum 0.03% | 41146 | 51356 |
| chitin nanofiber 0.001% | 83013 | 93642 |
| chitin nanofiber 0.003% | 92611 | 102669 |
| chitin nanofiber 0.01% | 91771 | 106490 |
| chitin nanofiber 0.03% | 115710 | 126305 |
| chitosan nanofiber 0.001% | 46009 | 50525 |
| chitosan nanofiber 0.003% | 46103 | 48083 |
| chitosan nanofiber 0.01% | 85922 | 93831 |
| chitosan nanofiber 0.03% | 119566 | 126395 |

Experimental Example 19: Fresh *Macaca fascicularis* Primary Hepatocytes Preservation Test Cellulose nanofiber (PNC) prepared in Production Example 2 and 1 mass % (w/v) aqueous solution of K-carageenan (GENUGEL WR-80-J, manufactured by SANSHO Co., Ltd.: Car) produced in the same manner as in Example 5 were used. A medium composition which is 10% FBS-containing Williams' Emedium (manufactured by Life Technologies, Inc.) added with PNC or carageenan at a final concentration of 0.03% (w/v), 0.1%, and a no-addition medium composition free of the above-mentioned substrates were prepared. Successively, fresh *Macaca fascicularis* primary hepatocytes (manufactured by Ina Research Inc.) was mixed with the above-mentioned medium compositions added with PNC or carageenan at 2,500,000 cells/mL, and dispensed in a Cryogenic cell freezing vial (manufactured by Thermo SCIENTIFIC). The above-mentioned medium free of the substrates and suspending *Macaca fascicularis* primary hepatocytes was dispensed. The above-mentioned operation was performed with 2 lots. Successively, this tube was transported while being stood still for 2 days in cold storage (about 4° C.) Trypan Blue reagent (manufactured by Life Technologies, Inc.) was used for the cell suspension transported for 2 days in cold storage conditions, and the survival rate of the cells in the suspension was measured.

As a result, a higher survival rate was obtained than that in non-addition conditions by transporting fresh monkey primary hepatocytes in cold storage by using PNC which is the medium composition of the present invention. In contrast, carageenan did not show such action. The survival rate is shown in Table 10.

TABLE 64

|  | lot 1 survival rate (%) | lot 2 survival rate (%) |
| --- | --- | --- |
| no addition | 48 | 41 |
| PNC 0.03% | 62 | 48 |
| PNC 0.1% | 62 | 56 |
| carageenan 0.03% | 37 | 35 |
| carageenan 0.1% | 42 | 23 |

Experimental Example 20: Evaluation of Proliferation Potency after Re-Seeding

Mouse preadipocyte strain 3T3-L1 (manufactured by ATCC) was seeded in a 10% FBS-containing DMEM medium on a 10 cm polystyrene petri dish and cultured in an incubator set to 5% $CO_2$, 37° C. When 313-L1 cells became confluent, the medium was aspirated, FBS was removed by D-PBS (manufactured by Wako Pure Chemical Industries, Ltd.), and a solution (1 ml) containing 0.25% Trypsin and 1 mM EDTA (manufactured by Wako Pure Chemical Industries, Ltd.) was added to the above-mentioned polystyrene petri dish. After confirmation of cell detachment, 10% by volume FBS-containing DMEM medium was added and the cells were recovered from the petri dish and placed in a centrifugation tube. The cells were centrifuged at 300×g, and the supernatant was removed. A cell suspension of about 200×$10^4$ cells/mL was prepared, 150 µL of the cell suspension was added into a 1.5 mL microtube, the medium compositions of Example 2 (PNC concentration 0.06%) to Example 4 (DAG concentration 0.03%), Comparative Example 5 (Alg concentration 0.03%) prepared in advance to contain 10% (v/v) FBS, and DMEM medium containing 10% by volume of FBS as a negative control were added by 150 each and the mixtures were pipetted to give cell suspensions (about $100 \times 10^4$ cells/mL).

The cell suspensions were preserved in a standing state in a tightly closed state at room temperature for 7 days and a part thereof was diluted with 10% FBS-containing DMEM medium. A cell suspension of about $10 \times 10^4$ cells/mL was prepared with the seeding concentration before 7 day preservation as the standard. The cell suspension was seeded in 96 well Multiplate (manufactured by Corning Incorporated) by 100 μL, and ATP reagent (100 μL) (CellTiter-Glo™ Luminescent Cell Viability Assay, manufactured by Promega) was added thereto on the day of seeding, one day later and two days later, and the mixture was stood for 15 min at room temperature. The luminescence intensity (RLU value) was measured by FlexStation3 (manufactured by Molecular Devices), and the luminescence of the medium alone was subtracted, whereby the viable cell number was measured.

As a result, the viable cell number (RLU value) of the negative control and the medium composition of Comparative Example 5 on the day of re-seeding after 7 day preservation was markedly lower than that of the medium compositions of Example 2 to Example 4. The viable cell number (RLU value) of Example 2 and Example 4 one day after the re-seeding increased as compared to that on the day of the re-seeding, and the cells after preservation maintained proliferation potency. The results of viable cell number are shown in Table 65.

TABLE 65

|  |  | polysaccharides | concentration | RLU value (viable cell number) | |
|---|---|---|---|---|---|
|  |  |  |  | day of re-seeding | one day later |
| negative target |  | — | 0% | 1749 | 6845 |
| Example | 2 | PNC | 0.03% | 13717 | 20282 |
|  | 4 | DAG | 0.015% | 14770 | 22588 |

TABLE 65-continued

|  |  | polysaccharides | concentration | RLU value (viable cell number) | |
|---|---|---|---|---|---|
|  |  |  |  | day of re-seeding | one day later |
| Comparative Example | 5 | Alg | 0.03% | 7466 | 14407 |

INDUSTRIAL APPLICABILITY

The medium composition of the present invention shows a superior effect of suspending cells and/or tissues, and is extremely useful for large-scale cultivation of cells and/or tissues derived from animals and plants while maintaining the function thereof. In addition, the cells and/or tissues cultured by the method of the present invention are extremely useful for efficacy and toxicity evaluation of chemical substances, pharmaceutical products and the like, large-scale production of useful substances such as enzymes, cell growth factors, antibodies and the like, and in the field of regenerative medicine for supplementing organ, tissue and cell that were lost by disease and deficiency, and the like.

The contents disclosed in any publication cited herein, including patents and patent applications, are hereby incorporated in their entireties by reference, to the extent that they have been disclosed herein.

This application is based on a patent application Nos. 2014-010842 (filing date: Jan. 23, 2014), 2014-123772 (filing date: Jun. 16, 2014), 2014-174574 (filing date: Aug. 28, 2014), and 2014-217761 (filing date: Oct. 24, 2014) filed in Japan, the contents of which are incorporated in full herein.

The invention claimed is:

1. A method of proliferating an adherent cell, comprising suspension culturing the adherent cell in a medium composition comprising a chitin nanofiber attached to the adherent cell, wherein the medium composition has a chitin nanofiber content of 0.001% (weight/volume) to 0.1% (weight/volume).

* * * * *